(12) United States Patent
Biggs et al.

(10) Patent No.: US 8,728,528 B2
(45) Date of Patent: May 20, 2014

(54) PROCESS FOR PREPARING MICROPARTICLES HAVING A LOW RESIDUAL SOLVENT VOLUME

(75) Inventors: Danielle Biggs, Hoover, AL (US); Heather Nettles, Bessemer, AL (US)

(73) Assignee: Evonik Corporation, Parsippany, NJ (US)

( * ) Notice: Subject to any disclaimer, the term of this patent is extended or adjusted under 35 U.S.C. 154(b) by 932 days.

(21) Appl. No.: 12/338,488

(22) Filed: Dec. 18, 2008

(65) Prior Publication Data

US 2009/0162407 A1 Jun. 25, 2009

Related U.S. Application Data

(60) Provisional application No. 61/015,321, filed on Dec. 20, 2007.

(51) Int. Cl.
*A61K 9/14* (2006.01)
*A61K 9/16* (2006.01)
*A61K 8/90* (2006.01)

(52) U.S. Cl.
CPC ............. *A61K 9/1694* (2013.01); *A61K 9/1641* (2013.01); *A61K 8/90* (2013.01)
USPC .......................................... 424/489; 424/501

(58) Field of Classification Search
None
See application file for complete search history.

(56) References Cited

U.S. PATENT DOCUMENTS

| | | | |
|---|---|---|---|
| 2,648,609 A | 8/1953 | Wurster et al. | 427/213 |
| 3,089,824 A | 5/1963 | Wurster et al. | 424/489 |
| 3,117,027 A | 1/1964 | Lindlof et al. | 118/303 |
| 3,196,827 A | 7/1965 | Wurster et al. | 118/24 |
| 3,241,520 A | 3/1966 | Wurster et al. | 118/62 |
| 3,253,944 A | 5/1966 | Wurster et al. | 427/213 |
| 3,773,919 A | 11/1973 | Boswell et al. | 424/19 |
| 3,978,203 A | 8/1976 | Wise | 424/22 |
| 4,069,307 A | 1/1978 | Higuchi et al. | 424/22 |
| 4,093,709 A | 6/1978 | Choi et al. | 424/19 |
| 4,134,742 A | 1/1979 | Schell | 95/53 |
| 4,186,189 A | 1/1980 | Shalaby | 424/78 |
| 4,249,531 A | 2/1981 | Heller et al. | 128/260 |
| 4,344,431 A | 8/1982 | Yolles | 128/260 |
| 4,346,709 A | 8/1982 | Schmitt | 128/260 |
| 4,351,337 A | 9/1982 | Sidman | 128/260 |
| 4,419,340 A | 12/1983 | Yolles | 424/19 |
| 4,450,150 A | 5/1984 | Sidman | 424/424 |

(Continued)

FOREIGN PATENT DOCUMENTS

| | | |
|---|---|---|
| EP | 1140028 | 10/2001 |
| EP | 1374860 | 1/2004 |

(Continued)

OTHER PUBLICATIONS

Resomer RGP® from Boehringer Ingelheim (product sheet, 2003, p. 1).*

(Continued)

*Primary Examiner* — Bethany Barham
(74) *Attorney, Agent, or Firm* — Linda S. Li; Jason S. Ngui

(57) ABSTRACT

The disclosed processes for forming microparticles utilize low volumes of processing water while still providing microparticles having low residual solvent levels. The processes are adaptable to both continuous and batch processes using oil/water or water/oil or water/oil/water or oil/water/oil emulsions.

49 Claims, 2 Drawing Sheets

(56) References Cited

U.S. PATENT DOCUMENTS

| | | | |
|---|---|---|---|
| 4,530,840 A | 7/1985 | Tice et al. | 514/179 |
| 4,568,559 A | 2/1986 | Nuwayser et al. | 427/3 |
| 4,612,009 A | 9/1986 | Drobnik et al. | 424/426 |
| 4,623,588 A | 11/1986 | Nuwayser et al. | 428/402.24 |
| 4,650,665 A | 3/1987 | Kronenthal et al. | 424/435 |
| 4,657,543 A | 4/1987 | Langer et al. | 604/891 |
| 4,720,384 A | 1/1988 | Di Luccio et al. | 424/78 |
| 4,794,001 A | 12/1988 | Mehta et al. | 424/458 |
| 4,795,643 A | 1/1989 | Seth | 424/456 |
| 4,824,937 A | 4/1989 | Deghenghi et al. | 530/326 |
| 4,828,563 A | 5/1989 | Müller-Lierheim | 623/16 |
| 4,832,686 A | 5/1989 | Anderson | 604/49 |
| 4,835,139 A | 5/1989 | Tice et al. | 514/15 |
| 4,839,130 A | 6/1989 | Kaplan et al. | 264/235 |
| 4,853,225 A | 8/1989 | Wahlig et al. | 424/423 |
| 4,863,735 A | 9/1989 | Kohn et al. | 424/622 |
| 4,883,666 A | 11/1989 | Sabel et al. | 424/422 |
| 4,894,231 A | 1/1990 | Moreau et al. | 424/426 |
| 4,897,268 A | 1/1990 | Tice et al. | 424/422 |
| 4,898,734 A | 2/1990 | Mathiowitz et al. | 424/426 |
| 4,902,515 A | 2/1990 | Loomis et al. | 424/486 |
| 4,952,403 A | 8/1990 | Vallee et al. | 424/422 |
| 4,957,119 A | 9/1990 | De Nijs | 128/832 |
| 4,975,280 A | 12/1990 | Schacht et al. | 424/428 |
| 4,976,949 A | 12/1990 | Meyer et al. | 424/1.1 |
| 4,981,696 A | 1/1991 | Loomis et al. | 424/486 |
| 5,013,553 A | 5/1991 | Southard et al. | 424/426 |
| 5,019,400 A | 5/1991 | Gombotz et al. | 424/497 |
| 5,035,891 A | 7/1991 | Runkel et al. | 424/423 |
| 5,110,595 A | 5/1992 | Wang | 424/422 |
| 5,114,719 A | 5/1992 | Sabel et al. | 424/422 |
| 5,134,122 A | 7/1992 | Orsolini | 514/15 |
| 5,141,748 A | 8/1992 | Rizzo | 424/425 |
| 5,150,718 A | 9/1992 | De Nijs | 128/832 |
| 5,152,781 A | 10/1992 | Tang et al. | 606/230 |
| 5,153,002 A | 10/1992 | McMullen | 424/473 |
| 5,164,190 A | 11/1992 | Patel et al. | 424/448 |
| 5,178,874 A | 1/1993 | Kwan et al. | 424/438 |
| 5,187,150 A | 2/1993 | Speiser et al. | 514/2 |
| 5,192,741 A | 3/1993 | Orsolini et al. | 514/4 |
| 5,225,205 A | 7/1993 | Orsolini | 424/489 |
| 5,232,707 A | 8/1993 | Lokensgard | 424/490 |
| 5,234,693 A | 8/1993 | Magruder et al. | 424/473 |
| 5,273,752 A | 12/1993 | Ayer et al. | 424/438 |
| 5,310,559 A | 5/1994 | Shah et al. | 424/448 |
| 5,340,586 A | 8/1994 | Pike et al. | 424/426 |
| 5,342,627 A | 8/1994 | Chopra et al. | 424/473 |
| 5,356,635 A | 10/1994 | Raman et al. | 424/484 |
| 5,382,435 A | 1/1995 | Geary et al. | 424/489 |
| 5,395,618 A | 3/1995 | Darougar et al. | 424/427 |
| 5,397,572 A | 3/1995 | Coombes et al. | 424/426 |
| 5,403,595 A | 4/1995 | Kitchell et al. | 424/501 |
| 5,407,609 A | 4/1995 | Tice et al. | 264/46 |
| 5,429,634 A | 7/1995 | Narciso | 604/890.1 |
| 5,429,822 A | 7/1995 | Gresser et al. | 424/426 |
| 5,439,688 A | 8/1995 | Orsolini et al. | 424/489 |
| 5,445,832 A | 8/1995 | Orsolini et al. | 424/491 |
| 5,456,679 A | 10/1995 | Balaban et al. | 604/892.1 |
| 5,456,917 A | 10/1995 | Wise et al. | 424/426 |
| 5,461,140 A | 10/1995 | Heller et al. | 528/425 |
| 5,478,355 A | 12/1995 | Muth et al. | 606/230 |
| 5,486,362 A | 1/1996 | Kitchell et al. | 424/426 |
| 5,518,730 A | 5/1996 | Fuisz | 424/426 |
| 5,531,998 A | 7/1996 | Mares et al. | 424/426 |
| 5,541,172 A | 7/1996 | Labrie et al. | 514/169 |
| 5,543,156 A | 8/1996 | Roorda et al. | 424/484 |
| 5,565,215 A | 10/1996 | Gref et al. | 424/501 |
| 5,565,443 A | 10/1996 | Lanquetin et al. | 514/169 |
| 5,571,525 A | 11/1996 | Roorda et al. | 424/426 |
| 5,607,417 A | 3/1997 | Batich et al. | 604/890.1 |
| 5,620,697 A | 4/1997 | Tormala et al. | 424/426 |
| 5,626,862 A | 5/1997 | Brem et al. | 424/426 |
| 5,628,993 A | 5/1997 | Yamagata et al. | 424/85.7 |
| 5,630,808 A | 5/1997 | Magruder et al. | 604/892.1 |
| 5,633,000 A | 5/1997 | Grossman et al. | 424/422 |
| 5,633,002 A | 5/1997 | Stricker et al. | 424/426 |
| 5,635,379 A | 6/1997 | Deghenghi | 435/106 |
| 5,637,568 A | 6/1997 | Orsolini et al. | 514/15 |
| 5,646,301 A | 7/1997 | Deghenghi | 548/496 |
| 5,650,173 A | 7/1997 | Ramstack et al. | 424/489 |
| 5,651,986 A | 7/1997 | Brem et al. | 424/484 |
| 5,654,008 A | 8/1997 | Herbert et al. | 424/489 |
| 5,654,010 A | 8/1997 | Johnson et al. | 424/502 |
| 5,656,297 A | 8/1997 | Bernstein et al. | 424/484 |
| 5,668,254 A | 9/1997 | Deghenghi | 530/328 |
| 5,681,568 A | 10/1997 | Goldin et al. | 424/184.1 |
| 5,681,873 A | 10/1997 | Norton et al. | 523/115 |
| 5,700,477 A | 12/1997 | Rosenthal et al. | 424/426 |
| 5,702,716 A | 12/1997 | Dunn et al. | 424/422 |
| 5,705,191 A | 1/1998 | Price et al. | 424/473 |
| 5,711,960 A | 1/1998 | Shikinami | 424/426 |
| 5,711,968 A | 1/1998 | Tracy et al. | 424/487 |
| 5,716,644 A | 2/1998 | Zale et al. | 424/497 |
| 5,747,060 A | 5/1998 | Sackler et al. | 424/426 |
| 5,750,100 A | 5/1998 | Yamagata et al. | 424/85.2 |
| 5,750,143 A | 5/1998 | Rashid et al. | 424/451 |
| 5,756,117 A | 5/1998 | D'Angelo et al. | 424/449 |
| 5,766,242 A | 6/1998 | Wong et al. | 623/4 |
| 5,776,885 A | 7/1998 | Orsolini et al. | 514/2 |
| 5,780,044 A | 7/1998 | Yewey et al. | 424/426 |
| 5,792,477 A | 8/1998 | Rickey et al. | 424/501 |
| 5,795,957 A | 8/1998 | Deghenghi | 530/329 |
| 5,798,113 A | 8/1998 | Dionne et al. | 424/422 |
| 5,800,828 A | 9/1998 | Dionne et al. | 424/422 |
| 5,800,829 A | 9/1998 | Dionne et al. | 424/422 |
| 5,807,985 A | 9/1998 | Deghenghi | 530/331 |
| 5,814,342 A | 9/1998 | Okada et al. | 424/493 |
| 5,817,327 A | 10/1998 | Ducheyne et al. | 424/425 |
| 5,817,343 A | 10/1998 | Burke | 424/489 |
| 5,834,001 A | 11/1998 | Dionne et al. | 424/422 |
| 5,837,228 A | 11/1998 | Shih et al. | 424/78.37 |
| 5,846,565 A | 12/1998 | Brem et al. | 424/486 |
| 5,851,547 A | 12/1998 | Fujioka et al. | 424/426 |
| 5,869,077 A | 2/1999 | Dionne et al. | 424/422 |
| 5,869,103 A | 2/1999 | Yeh et al. | 424/501 |
| 5,871,767 A | 2/1999 | Dionne et al. | 424/422 |
| 5,872,100 A | 2/1999 | Deghenghi | 514/15 |
| 5,874,098 A | 2/1999 | Stevens et al. | 424/408 |
| 5,874,099 A | 2/1999 | Dionne et al. | 424/422 |
| 5,876,452 A | 3/1999 | Athanasiou et al. | 623/16 |
| 5,900,425 A | 5/1999 | Kanikanti et al. | 514/356 |
| 5,906,817 A | 5/1999 | Moullier et al. | 424/93.21 |
| 5,912,015 A | 6/1999 | Bernstein et al. | 424/484 |
| 5,916,584 A | 6/1999 | O'Donoghue et al. | 424/426 |
| 5,916,597 A | 6/1999 | Lee et al. | 424/501 |
| 5,922,253 A | 7/1999 | Herbert et al. | 264/5 |
| 5,922,340 A | 7/1999 | Berde et al. | 424/426 |
| 5,922,357 A | 7/1999 | Coombes et al. | 424/491 |
| 5,942,241 A | 8/1999 | Chasin et al. | 424/426 |
| 5,945,115 A | 8/1999 | Dunn et al. | 424/422 |
| 5,945,128 A | 8/1999 | Deghenghi | 424/501 |
| 5,945,284 A | 8/1999 | Livak et al. | 435/6 |
| 5,958,458 A | 9/1999 | Norling et al. | 424/490 |
| 5,965,125 A | 10/1999 | Mineau-Hanschke | 424/93.21 |
| 5,980,927 A | 11/1999 | Nelson et al. | 424/425 |
| 5,985,305 A | 11/1999 | Peery et al. | 424/422 |
| 5,989,463 A | 11/1999 | Tracy et al. | 264/4.1 |
| 6,013,853 A | 1/2000 | Athanasiou et al. | 623/11 |
| 6,045,830 A | 4/2000 | Igari et al. | 424/501 |
| 6,063,395 A | 5/2000 | Markkula et al. | 424/422 |
| 6,066,325 A | 5/2000 | Wallace et al. | 424/400 |
| 6,077,523 A | 6/2000 | Deghenghi et al. | 424/426 |
| 6,083,523 A | 7/2000 | Dionne et al. | 424/424 |
| 6,086,908 A | 7/2000 | Gopferich | 424/424 |
| 6,090,925 A | 7/2000 | Woiszwillo et al. | 530/410 |
| 6,096,331 A | 8/2000 | Desai et al. | 424/422 |
| 6,117,441 A | 9/2000 | Moo-Young et al. | 424/422 |
| 6,117,442 A | 9/2000 | Markkula et al. | 424/422 |
| 6,143,314 A | 11/2000 | Chandrashekar et al. | 424/426 |
| 6,153,211 A | 11/2000 | Hubbell et al. | 424/426 |
| 6,156,331 A | 12/2000 | Peery et al. | 424/422 |
| 6,159,490 A | 12/2000 | Deghenghi | 424/426 |
| 6,165,486 A | 12/2000 | Marra et al. | 424/423 |
| 6,183,781 B1 | 2/2001 | Burke | 424/486 |

(56) References Cited

U.S. PATENT DOCUMENTS

| | | | |
|---|---|---|---|
| 6,187,329 B1 | 2/2001 | Agrawal et al. | 424/426 |
| 6,194,000 B1 | 2/2001 | Smith et al. | 424/458 |
| 6,203,813 B1 | 3/2001 | Gooberman | 424/422 |
| 6,214,370 B1 | 4/2001 | Nelson et al. | 424/425 |
| 6,228,111 B1 | 5/2001 | Tormala et al. | 623/1.38 |
| 6,245,346 B1 | 6/2001 | Rothen-Weinhold et al. | 424/426 |
| 6,245,347 B1 | 6/2001 | Zhang et al. | 424/449 |
| 6,248,363 B1 | 6/2001 | Patel et al. | 424/497 |
| 6,261,584 B1 | 7/2001 | Peery et al. | 424/422 |
| 6,262,127 B1 | 7/2001 | Acemoglu et al. | 514/772.7 |
| 6,268,053 B1 | 7/2001 | Woiszwillo et al. | 428/402 |
| RE37,410 E | 10/2001 | Brem et al. | 424/484 |
| 6,296,842 B1 | 10/2001 | Jaworowicz et al. | 424/78.02 |
| 6,303,137 B1 | 10/2001 | Dittgen et al. | 424/426 |
| 6,306,423 B1 | 10/2001 | Donovan et al. | 424/423 |
| 6,309,660 B1 | 10/2001 | Hsu et al. | 424/425 |
| 6,312,708 B1 | 11/2001 | Donovan et al. | 424/423 |
| 6,319,512 B1 | 11/2001 | Rothen-Weinhold et al. | 424/425 |
| 6,331,313 B1 | 12/2001 | Wong et al. | 424/427 |
| 6,365,172 B1 | 4/2002 | Barrows | 424/423 |
| 6,368,630 B1 | 4/2002 | Bernstein et al. | 424/486 |
| 6,375,972 B1 | 4/2002 | Guo et al. | 424/423 |
| 6,379,962 B1 | 4/2002 | Holy et al. | 435/395 |
| 6,383,509 B1 | 5/2002 | Donovan et al. | 424/423 |
| 6,395,292 B2 | 5/2002 | Peery et al. | 424/422 |
| 6,406,719 B1 | 6/2002 | Farrar et al. | 424/489 |
| 6,410,056 B1 | 6/2002 | Setterstrom et al. | 424/501 |
| 6,419,655 B1 | 7/2002 | Nett et al. | 604/57 |
| 6,419,920 B1 | 7/2002 | Mineau-Hanschke | 424/93.21 |
| 6,419,954 B1 | 7/2002 | Chu et al. | 424/465 |
| 6,440,493 B1 | 8/2002 | Gibson et al. | 427/213.3 |
| 6,447,542 B1 | 9/2002 | Weadock | 623/11.11 |
| 6,447,796 B1 | 9/2002 | Vook et al. | 424/422 |
| 6,455,526 B1 | 9/2002 | Kohn et al. | 514/248 |
| 6,472,210 B1 | 10/2002 | Holy et al. | 435/395 |
| 6,475,779 B2 | 11/2002 | Mathiowitz et al. | 435/320.1 |
| 6,479,065 B2 | 11/2002 | Jaworowicz et al. | 424/423 |
| 6,506,399 B2 | 1/2003 | Donovan | 424/423 |
| 6,506,410 B1 | 1/2003 | Park et al. | 424/489 |
| 6,514,516 B1 | 2/2003 | Chasin et al. | 424/426 |
| 6,514,533 B1 | 2/2003 | Burke et al. | 424/486 |
| 6,521,259 B1 | 2/2003 | Chasin et al. | 424/489 |
| 6,524,607 B1 | 2/2003 | Goldenheim et al. | 424/426 |
| 6,528,080 B2 | 3/2003 | Dunn et al. | 424/426 |
| 6,528,097 B1 | 3/2003 | Vaughn et al. | 424/501 |
| 6,537,586 B2 | 3/2003 | Lyons et al. | 424/501 |
| 6,540,393 B1 | 4/2003 | Lyons et al. | 366/181.5 |
| 6,545,097 B2 | 4/2003 | Pinchuk et al. | 525/240 |
| 6,555,525 B2 | 4/2003 | Burke | 514/44 |
| 6,565,777 B2 | 5/2003 | Farrar et al. | 264/4.1 |
| 6,569,463 B2 | 5/2003 | Patel et al. | 424/497 |
| 6,576,258 B1 | 6/2003 | Kofler et al. | 424/458 |
| 6,576,263 B2 | 6/2003 | Truong et al. | 424/489 |
| 6,579,533 B1 | 6/2003 | Tormala et al. | 424/426 |
| 6,585,993 B2 | 7/2003 | Donovan | 424/423 |
| 6,596,308 B2 | 7/2003 | Gutierrez-Rocca et al. | 424/451 |
| 6,599,529 B1 | 7/2003 | Skinhøj et al. | 424/458 |
| 6,620,422 B1 | 9/2003 | Maquin et al. | 424/422 |
| 6,623,749 B2 | 9/2003 | Williams et al. | 424/423 |
| 6,627,600 B2 | 9/2003 | Boutignon | 514/2 |
| 6,632,446 B1 | 10/2003 | Hubbell et al. | 424/423 |
| 6,641,831 B1 | 11/2003 | Schierholz | 424/422 |
| 6,648,849 B2 | 11/2003 | Tenhuisen et al. | 604/60 |
| 6,669,955 B2 | 12/2003 | Chungi et al. | 424/464 |
| 6,669,959 B1 | 12/2003 | Adjei et al. | 424/489 |
| 6,669,961 B2 | 12/2003 | Kim et al. | 424/489 |
| 6,680,065 B1 | 1/2004 | Podszun | 424/426 |
| 6,689,390 B2 | 2/2004 | Bernstein et al. | 424/501 |
| 6,696,073 B2 | 2/2004 | Boyce et al. | 424/422 |
| 6,702,803 B2 | 3/2004 | Kupperblatt et al. | 604/890.1 |
| 6,719,935 B2 | 4/2004 | Tunc | 264/40.7 |
| 6,719,989 B1 | 4/2004 | Matsushima et al. | 424/422 |
| 6,730,322 B1 | 5/2004 | Bernstein et al. | 424/486 |
| 6,746,661 B2 | 6/2004 | Kaplan | 424/1.29 |
| 6,747,121 B2 | 6/2004 | Gogolewski | 528/354 |
| 6,749,866 B2 | 6/2004 | Bernstein et al. | 424/484 |
| 6,756,049 B2 | 6/2004 | Brubaker et al. | 424/428 |
| 6,756,058 B2 | 6/2004 | Brubaker et al. | 424/473 |
| 6,767,550 B1 | 7/2004 | Genin et al. | 424/426 |
| 6,774,155 B2 | 8/2004 | Martakos et al. | 522/157 |
| 6,777,002 B1 | 8/2004 | Vuaridel et al. | 424/489 |
| 6,793,938 B2 | 9/2004 | Sankaram | 424/489 |
| 6,828,357 B1 | 12/2004 | Martin et al. | 523/124 |
| 6,835,194 B2 | 12/2004 | Johnson et al. | 604/890.1 |
| 6,844,010 B1 | 1/2005 | Setterstrom et al. | 424/501 |
| 6,855,331 B2 | 2/2005 | Vook et al. | 424/422 |
| 6,855,770 B2 | 2/2005 | Pinchuk et al. | 525/240 |
| 6,858,222 B2 | 2/2005 | Nelson et al. | 424/426 |
| 6,869,588 B2 | 3/2005 | Weller et al. | 424/1.29 |
| 6,887,270 B2 | 5/2005 | Miller et al. | 623/23.7 |
| 6,899,898 B2 | 5/2005 | Albayrak | 424/489 |
| 6,902,743 B1 | 6/2005 | Setterstrom et al. | 424/489 |
| 6,913,760 B2 | 7/2005 | Carr et al. | 424/484 |
| 6,913,762 B2 | 7/2005 | Caplice et al. | 424/423 |
| 6,913,764 B2 | 7/2005 | Vogt et al. | 424/423 |
| 6,913,767 B1 | 7/2005 | Cleland et al. | 424/468 |
| 6,916,483 B2 | 7/2005 | Ralph et al. | 424/422 |
| 6,921,541 B2 | 7/2005 | Chasin et al. | 424/426 |
| 6,923,988 B2 | 8/2005 | Patel et al. | 424/497 |
| 6,926,903 B2 | 8/2005 | Pirhonen et al. | 424/426 |
| 6,939,375 B2 | 9/2005 | Sirhan et al. | 623/1.42 |
| 6,945,949 B2 | 9/2005 | Wilk | 604/8 |
| 6,960,351 B2 | 11/2005 | Dionne et al. | 424/422 |
| 6,962,716 B1 | 11/2005 | King et al. | 424/489 |
| 6,991,802 B1 | 1/2006 | Ahola et al. | 424/423 |
| 7,034,050 B2 | 4/2006 | Deghenghi et al. | 514/419 |
| 7,048,946 B1 | 5/2006 | Wong et al. | 424/486 |
| 7,049,348 B2 | 5/2006 | Evans et al. | 521/82 |
| 7,052,719 B2 | 5/2006 | Bernstein et al. | 424/501 |
| 7,074,426 B2 | 7/2006 | Kochinke | 424/423 |
| 7,097,850 B2 | 8/2006 | Chappa et al. | 424/423 |
| 7,101,394 B2 | 9/2006 | Hamm et al. | 623/1.42 |
| 7,101,567 B1 | 9/2006 | Sano et al. | 424/472 |
| 7,153,519 B2 | 12/2006 | Hubbell et al. | 435/6 |
| 7,163,691 B2 | 1/2007 | Knaack et al. | 424/422 |
| 7,169,405 B2 | 1/2007 | Trieu | 424/426 |
| 7,192,604 B2 | 3/2007 | Brown et al. | 424/422 |
| 7,226,612 B2 | 6/2007 | Sohier et al. | 424/426 |
| 7,279,175 B2 | 10/2007 | Chen et al. | 424/423 |
| 7,303,758 B2 | 12/2007 | Falotico et al. | 424/424 |
| 2001/0009769 A1 | 7/2001 | Williams et al. | 435/135 |
| 2001/0026804 A1 | 10/2001 | Boutignon | 424/422 |
| 2002/0028244 A1 | 3/2002 | Donovan et al. | 424/486 |
| 2002/0037309 A1 | 3/2002 | Jaworowicz et al. | 424/423 |
| 2002/0054900 A1 | 5/2002 | Kamath et al. | 424/425 |
| 2002/0064547 A1 | 5/2002 | Chern et al. | 424/426 |
| 2002/0090398 A1 | 7/2002 | Dunn et al. | 424/486 |
| 2002/0098237 A1 | 7/2002 | Donovan et al. | 424/484 |
| 2002/0107330 A1 | 8/2002 | Pinchuk et al. | 525/242 |
| 2002/0119179 A1 | 8/2002 | Rezania et al. | 424/426 |
| 2002/0131953 A1 | 9/2002 | Takashima et al. | 424/85.1 |
| 2002/0131988 A1 | 9/2002 | Foster et al. | 424/422 |
| 2002/0150603 A1 | 10/2002 | Dionne et al. | 424/424 |
| 2002/0160033 A1 | 10/2002 | Caplice et al. | 424/423 |
| 2002/0168393 A1 | 11/2002 | Sugimoto | 424/423 |
| 2003/0004491 A1 | 1/2003 | Tenhuisen et al. | 604/502 |
| 2003/0007992 A1 | 1/2003 | Gibson et al. | 424/426 |
| 2003/0031700 A1 | 2/2003 | Hammang et al. | 424/424 |
| 2003/0039676 A1 | 2/2003 | Boyce et al. | 424/423 |
| 2003/0049263 A1 | 3/2003 | Bhagwatwar et al. | 424/486 |
| 2003/0060871 A1 | 3/2003 | Hill et al. | 623/1.15 |
| 2003/0068381 A1 | 4/2003 | Albayrak | 424/497 |
| 2003/0093157 A1 | 5/2003 | Casares et al. | 623/23.73 |
| 2003/0095995 A1 | 5/2003 | Wong et al. | 424/426 |
| 2003/0104029 A1 | 6/2003 | Pirhonen et al. | 424/426 |
| 2003/0108588 A1 | 6/2003 | Chen et al. | 424/423 |
| 2003/0133964 A1 | 7/2003 | Dunn et al. | 424/428 |
| 2003/0143258 A1 | 7/2003 | Knaack et al. | 424/426 |
| 2003/0152634 A1 | 8/2003 | Bodmeier | 424/489 |
| 2003/0153983 A1 | 8/2003 | Miller et al. | 623/23.7 |
| 2003/0158598 A1 | 8/2003 | Ashton et al. | 623/1.42 |
| 2003/0161881 A1 | 8/2003 | Hansen et al. | 424/468 |

(56) References Cited

U.S. PATENT DOCUMENTS

| | | | |
|---|---|---|---|
| 2003/0165555 A1 | 9/2003 | Ding et al. | 424/422 |
| 2003/0170288 A1 | 9/2003 | Carr et al. | 424/426 |
| 2003/0185872 A1 | 10/2003 | Kochine | 424/426 |
| 2003/0224033 A1 | 12/2003 | Li et al. | 424/423 |
| 2003/0229390 A1 | 12/2003 | Ashton et al. | 623/1.15 |
| 2003/0232122 A1 | 12/2003 | Chappa et al. | 427/2.1 |
| 2003/0235602 A1 | 12/2003 | Schwarz | 424/424 |
| 2004/0006146 A1 | 1/2004 | Evans et al. | 521/50 |
| 2004/0009228 A1 | 1/2004 | Tormala et al. | 424/486 |
| 2004/0010048 A1 | 1/2004 | Evans et al. | 521/50 |
| 2004/0013703 A1 | 1/2004 | Ralph et al. | 424/426 |
| 2004/0033250 A1 | 2/2004 | Patel | 424/423 |
| 2004/0034337 A1 | 2/2004 | Boulais et al. | 604/890.1 |
| 2004/0086569 A1 | 5/2004 | Sparer et al. | 424/486 |
| 2004/0115236 A1 | 6/2004 | Chan et al. | 424/423 |
| 2004/0115241 A1 | 6/2004 | Calhoun et al. | 424/426 |
| 2004/0126404 A1 | 7/2004 | Campbell et al. | 424/422 |
| 2004/0137065 A1 | 7/2004 | Vogt et al. | 424/486 |
| 2004/0142011 A1 | 7/2004 | Nilsson et al. | 424/422 |
| 2004/0143221 A1 | 7/2004 | Shadduck | 604/175 |
| 2004/0151753 A1 | 8/2004 | Chen et al. | 424/426 |
| 2004/0166141 A1 | 8/2004 | Cerami et al. | 424/426 |
| 2004/0175406 A1 | 9/2004 | Schwarz | 424/423 |
| 2004/0175410 A1 | 9/2004 | Ashton et al. | 424/427 |
| 2004/0202691 A1 | 10/2004 | Richard | 424/423 |
| 2004/0208910 A1 | 10/2004 | Ashton et al. | 424/427 |
| 2004/0208985 A1 | 10/2004 | Rowan et al. | 427/2.25 |
| 2004/0219180 A1 | 11/2004 | Gambale et al. | 424/423 |
| 2004/0224000 A1 | 11/2004 | Deghenghi et al. | 424/423 |
| 2004/0234572 A1 | 11/2004 | Martinod et al. | 424/423 |
| 2004/0234576 A1 | 11/2004 | Martin et al. | 424/426 |
| 2004/0241204 A1 | 12/2004 | Martinod et al. | 424/426 |
| 2004/0243097 A1 | 12/2004 | Falotico et al. | 604/500 |
| 2004/0247643 A1 | 12/2004 | Martinod et al. | 424/426 |
| 2004/0259768 A1 | 12/2004 | Lauermann | 514/2 |
| 2004/0260268 A1 | 12/2004 | Falotico et al. | 604/500 |
| 2004/0265383 A1 | 12/2004 | Cui et al. | 424/469 |
| 2004/0265475 A1 | 12/2004 | Hossainy et al. | 427/2.1 |
| 2005/0002895 A1 | 1/2005 | Corcoran | 424/78.17 |
| 2005/0002986 A1 | 1/2005 | Falotico et al. | 424/426 |
| 2005/0013840 A1 | 1/2005 | Potter et al. | 424/422 |
| 2005/0019367 A1 | 1/2005 | Booth et al. | 424/426 |
| 2005/0025801 A1 | 2/2005 | Richard et al. | 424/423 |
| 2005/0025802 A1 | 2/2005 | Richard et al. | 424/423 |
| 2005/0025803 A1 | 2/2005 | Richard et al. | 424/423 |
| 2005/0025806 A1 | 2/2005 | Brandon et al. | 424/423 |
| 2005/0027283 A1 | 2/2005 | Richard et al. | 604/890.1 |
| 2005/0031667 A1 | 2/2005 | Patel et al. | 424/426 |
| 2005/0031668 A1 | 2/2005 | Patel et al. | 424/426 |
| 2005/0031669 A1 | 2/2005 | Shafiee et al. | 424/426 |
| 2005/0037047 A1 | 2/2005 | Song | 424/423 |
| 2005/0042253 A1 | 2/2005 | Farrar et al. | 424/426 |
| 2005/0060019 A1 | 3/2005 | Gambale et al. | 623/1.11 |
| 2005/0065214 A1 | 3/2005 | Kronenthal | 514/557 |
| 2005/0070989 A1 | 3/2005 | Lye et al. | 623/1.4 |
| 2005/0079138 A1 | 4/2005 | Chickering et al. | 424/46 |
| 2005/0079199 A1 | 4/2005 | Heruth et al. | 424/423 |
| 2005/0079200 A1 | 4/2005 | Rathenow et al. | 424/423 |
| 2005/0079216 A1 | 4/2005 | Petereit et al. | 424/464 |
| 2005/0100582 A1 | 5/2005 | Stenzel | 424/426 |
| 2005/0118229 A1 | 6/2005 | Boiarski | 424/424 |
| 2005/0129728 A1 | 6/2005 | Martinod et al. | 424/423 |
| 2005/0147673 A1 | 7/2005 | Staniforth et al. | 424/464 |
| 2005/0158360 A1 | 7/2005 | Falotico et al. | 424/424 |
| 2005/0181015 A1 | 8/2005 | Zhong | 424/426 |
| 2005/0181048 A1 | 8/2005 | Romero | 424/469 |
| 2005/0182485 A1 | 8/2005 | Falotico et al. | 623/1.42 |
| 2005/0186239 A1 | 8/2005 | Hunter et al. | 424/423 |
| 2005/0186251 A1 | 8/2005 | Pirhonen et al. | 424/426 |
| 2005/0191333 A1 | 9/2005 | Hsu | 424/424 |
| 2005/0191334 A1 | 9/2005 | Wong et al. | 424/426 |
| 2005/0202059 A1 | 9/2005 | Falotico et al. | 424/423 |
| 2005/0208092 A1 | 9/2005 | Falotico et al. | 424/423 |
| 2005/0208095 A1 | 9/2005 | Hunter et al. | 424/423 |
| 2005/0208098 A1 | 9/2005 | Castro et al. | 424/423 |
| 2005/0244447 A1 | 11/2005 | Heath | 424/422 |
| 2005/0244461 A1 | 11/2005 | Nivaggioli et al. | 424/427 |
| 2005/0244465 A1 | 11/2005 | Nivaggioli et al. | 424/427 |
| 2005/0244467 A1 | 11/2005 | Nivaggioli et al. | 424/427 |
| 2005/0244468 A1 | 11/2005 | Huang et al. | 424/427 |
| 2005/0244469 A1 | 11/2005 | Whitcup et al. | 424/427 |
| 2005/0244506 A1 | 11/2005 | Burke et al. | 424/489 |
| 2005/0249775 A1 | 11/2005 | Falotico et al. | 424/423 |
| 2005/0249776 A1 | 11/2005 | Chen et al. | 424/423 |
| 2005/0271698 A1 | 12/2005 | Bucay-Couto et al. | 424/423 |
| 2005/0271706 A1 | 12/2005 | Anderson et al. | 424/427 |
| 2006/0002977 A1 | 1/2006 | Dugan | 424/426 |
| 2006/0002979 A1 | 1/2006 | Ashammakhi et al. | 424/426 |
| 2006/0003008 A1 | 1/2006 | Gibson et al. | 424/486 |
| 2006/0008503 A1 | 1/2006 | Shanley et al. | 424/425 |
| 2006/0013835 A1 | 1/2006 | Anderson et al. | 424/400 |
| 2006/0013849 A1 | 1/2006 | Strickler et al. | 424/422 |
| 2006/0013854 A1 | 1/2006 | Strickler et al. | 424/423 |
| 2006/0018948 A1 | 1/2006 | Guire et al. | 424/426 |
| 2006/0029637 A1 | 2/2006 | Tice et al. | 424/423 |
| 2006/0029678 A1 | 2/2006 | Deghenghi et al. | 424/489 |
| 2006/0039946 A1 | 2/2006 | Heruth et al. | 424/422 |
| 2006/0051390 A1 | 3/2006 | Schwarz | 424/422 |
| 2006/0073182 A1 | 4/2006 | Wong et al. | 424/426 |
| 2006/0083767 A1 | 4/2006 | Deusch et al. | 424/422 |
| 2006/0093557 A1 | 5/2006 | Dickinson et al. | 424/46 |
| 2006/0105018 A1 | 5/2006 | Epstein et al. | 424/426 |
| 2006/0115515 A1 | 6/2006 | Pirhonen et al. | 424/426 |
| 2006/0122290 A1 | 6/2006 | Hubbell et al. | 523/113 |
| 2006/0134168 A1 | 6/2006 | Chappa et al. | 424/422 |
| 2006/0140999 A1 | 6/2006 | Lendlein et al. | 424/422 |
| 2006/0147491 A1 | 7/2006 | DeWitt et al. | 424/426 |
| 2006/0159721 A1 | 7/2006 | Siegel et al. | 424/426 |
| 2006/0165754 A1 | 7/2006 | Ranade | 424/423 |
| 2006/0171980 A1 | 8/2006 | Helm et al. | 424/422 |
| 2006/0171981 A1 | 8/2006 | Richard et al. | 424/422 |
| 2006/0171987 A1 | 8/2006 | Mauriac et al. | 424/426 |
| 2006/0177480 A1 | 8/2006 | Sung et al. | 424/426 |
| 2006/0193888 A1 | 8/2006 | Lye et al. | 424/423 |
| 2006/0195176 A1 | 8/2006 | Bates et al. | 623/1.15 |
| 2006/0198868 A1 | 9/2006 | DeWitt et al. | 424/426 |
| 2006/0204533 A1 | 9/2006 | Hsu et al. | 424/422 |
| 2006/0204548 A1 | 9/2006 | Nivaggioli et al. | 424/427 |
| 2006/0210594 A1 | 9/2006 | Trieu | 424/422 |
| 2006/0210598 A1 | 9/2006 | Evans et al. | 424/422 |
| 2006/0210604 A1 | 9/2006 | Dadey et al. | 424/427 |
| 2006/0216323 A1 | 9/2006 | Knaack et al. | 424/422 |
| 2006/0222681 A1 | 10/2006 | Richard | 424/426 |
| 2006/0240071 A1 | 10/2006 | Lerner et al. | 424/426 |
| 2006/0246110 A1 | 11/2006 | Brandon et al. | 424/426 |
| 2006/0246112 A1 | 11/2006 | Snyder et al. | 424/427 |
| 2006/0257448 A1 | 11/2006 | Weber | 424/426 |
| 2006/0257451 A1 | 11/2006 | Varner et al. | 424/427 |
| 2007/0009564 A1 | 1/2007 | McClain et al. | 424/423 |
| 2007/0016163 A1 | 1/2007 | Santini | 604/500 |
| 2007/0020307 A1 | 1/2007 | Zhong | 424/423 |
| 2007/0048350 A1 | 3/2007 | Falotico et al. | 424/423 |
| 2007/0053952 A1 | 3/2007 | Chen et al. | 424/423 |
| 2007/0059336 A1 | 3/2007 | Hughes et al. | 424/426 |
| 2007/0059369 A1 | 3/2007 | Mauvernay | 424/486 |
| 2007/0077272 A1 | 4/2007 | Li et al. | 424/423 |
| 2007/0098753 A1 | 5/2007 | Falotico et al. | 424/423 |
| 2007/0116736 A1 | 5/2007 | Argentieri et al. | 424/424 |
| 2007/0116737 A1 | 5/2007 | Favis et al. | 424/426 |
| 2007/0116738 A1 | 5/2007 | Mauriac et al. | 424/426 |
| 2007/0154524 A1 | 7/2007 | Kauper et al. | 424/427 |
| 2007/0196423 A1 | 8/2007 | Ruane et al. | 424/423 |
| 2007/0196499 A1 | 8/2007 | Rickey et al. | 424/489 |
| 2007/0202147 A1 | 8/2007 | Kleiner et al. | 424/423 |
| 2007/0212388 A1 | 9/2007 | Patravale et al. | 424/422 |
| 2007/0224239 A1 | 9/2007 | Behan et al. | 424/423 |
| 2007/0243230 A1 | 10/2007 | De Juan et al. | 424/427 |
| 2007/0248637 A1 | 10/2007 | Chappa et al. | 424/422 |
| 2007/0254103 A1 | 11/2007 | Sohier et al. | 427/299 |
| 2007/0298073 A1 | 12/2007 | Whitcup et al. | 424/427 |
| 2007/0298074 A1 | 12/2007 | Robinson et al. | 424/427 |
| 2008/0003256 A1 | 1/2008 | Martens et al. | 424/425 |
| 2008/0014241 A1 | 1/2008 | DesNoyer et al. | 424/423 |
| 2008/0020012 A1 | 1/2008 | Ju et al. | 424/423 |

(56) References Cited

U.S. PATENT DOCUMENTS

| | | | |
|---|---|---|---|
| 2008/0026031 A1 | 1/2008 | Patel et al. | 424/423 |
| 2008/0026034 A1 | 1/2008 | Cook et al. | 424/426 |
| 2008/0031922 A1 | 2/2008 | Riihimaki | 424/424 |
| 2008/0038354 A1 | 2/2008 | Slager et al. | 424/487 |
| 2008/0051866 A1 | 2/2008 | Chen et al. | 623/1.11 |
| 2008/0057101 A1 | 3/2008 | Roorda | 424/425 |
| 2008/0057102 A1 | 3/2008 | Roorda | 424/425 |
| 2008/0057103 A1 | 3/2008 | Roorda | 424/425 |
| 2008/0058733 A1 | 3/2008 | Vogt et al. | 604/265 |
| 2008/0075753 A1 | 3/2008 | Chappa | 424/426 |
| 2008/0091222 A1 | 4/2008 | Deusch et al. | 606/151 |
| 2008/0166391 A1 | 7/2008 | Gibson et al. | 424/424 |
| 2010/0323014 A1* | 12/2010 | Bloom et al. | 424/486 |

FOREIGN PATENT DOCUMENTS

| | | |
|---|---|---|
| EP | 1601343 | 12/2005 |
| GB | 2103927 | 3/1983 |
| GB | 2249724 | 5/1992 |
| WO | WO 89/03678 | 5/1989 |
| WO | WO 93/17662 | 9/1993 |
| WO | WO 98/09613 | 3/1998 |
| WO | WO 98/17710 | 4/1998 |
| WO | WO 01/60339 | 8/2001 |
| WO | WO 2004/078160 | 9/2004 |
| WO | WO 2004/110603 | 12/2004 |
| WO | WO 2005/016396 | 2/2005 |
| WO | WO 2006/012667 | 2/2006 |
| ZA | 9803205 | 10/1998 |

OTHER PUBLICATIONS

Bhardwaj et al., "In vitro evaluation of Poly(d,l-lactide-co-glycolide) polymer-based implants containing the alpha-melanocyte stimulating hormone analog, Melanotan-I," *Journal of Controlled Release*, 45:49-55 (1997).

Freitas, "Liquid extraction as means of solvent removal," *JCR* 102(2):313 (2005).

International Search Report and Written Opinion for PCT/US08/087428 mailed Mar. 10, 2009.

Mallapragada et al., "Crystal Dissolution-Controlled Release Systems. II. Metronidazole Release From Semicrystalline Poly(vinyl alcohol) systems," *J Biomed Mater Res.*, 36(1):125-30 (1997).

Ruchatz et al., "Residual solvents in biodegradable microparticles: Determination by a dynamic headspace gas chromatographic method," *International J Pharm* 142:67-73 (1996).

Ruchatz et al,. "Residual solvents in biodegradable microparticles. Influence of process parameters on the residual solvent in microparticles produced by the aerosol extraction system (ASES) process," *J Pharm Sci* 86(1):101-105 (1997).

Sato et al,. "Processing difference yield porosity differences," *Pharm Res* 5(1):21-30 (1998).

Steendam, "SynBiosys™ Biodegradable Polymeric Drug Delivery System," *Business Briefing: Pharma Outsourcing*, p. 1-5 (2005).

Varner et al., "Coatings: Sustained-Release Drug Delivery for Retinal Disease," *Medical Device & Diagnostic Industry Magazine*, published Jul. 2005.

Yamakawa et al., "Sustained Release of Insulin by Double-Layered Implant Using Poly(D,L-Lactic Acid)," *J Pharm Sci*, 79(6): 505-509 (1990).

Zheng, "Effects of additives and processing on initial burst of proteins," *J Pharm Sci Technol* 60(1):54 (2006).

International Preliminary Report on Patentability issued by The International Bureau of WIPO on Jun. 22, 2010, for Intl. App. No. PCT/US2008/087428, filed Dec. 18, 2008 (Inventor—Biggs et al.; Applicant—Surmodics Pharmaceuticals, Inc.; pp. 1-10).

Preliminary Amendment filed by Applicant on Aug. 19, 2010 for EP Pat. App. No. 08866517.9, which is national phase of Intl. App. No. PCT/US2008/087428, filed Dec. 18, 2008 (Inventor—Biggs et al.; Applicant—Surmodics Pharmaceuticals, Inc.; pp. 1-6).

* cited by examiner

PROCESS FOR PREPARING MICROPARTICLES HAVING A LOW RESIDUAL SOLVENT VOLUME

CROSS REFERENCE TO RELATED APPLICATION

This application claims the benefit of priority to U.S. Provisional Application No. 61/015,321, filed Dec. 20, 2007, which is incorporated by reference herein in its entirety.

FIELD

The disclosed processes for forming microparticles utilize low volumes of processing water while still providing microparticles having low residual solvent levels. The processes are adaptable to both continuous and batch processes using oil/water or water/oil or water/oil/water or oil/water/oil emulsions.

BACKGROUND

Microparticles have found wide use in delivering active ingredients, not only for use ex vivo, but, for delivering therapeutic agents or vaccines in vivo. Depending upon the size and chemical structure of the microparticle, pharmaceutical agents can now be specifically targeted such that the active ingredient is absorbed or otherwise taken up by the body in a manner that increases the effectiveness of drug or vaccine therapy.

As with all synthetic agents delivered to the body, microparticles themselves have undergone chemical processing or synthesis. A goal of the microparticle formulator is to prepare a biodegradable, biocompatible vehicle for delivery of active agents. Therefore, it is often desired that the microparticle only comprise those ingredients the formulator intends to deliver. Indeed, great care is taken to remove any unwanted substances that are present due to the processing conditions use to encapsulate the pharmaceutical agent.

One key impurity is the solvent that is used in microparticle formulation. The balance between efficiency of residual solvent removal and the cost of manufacturing a microparticle is significant to the industry. Typically large amounts of water are necessary during the extraction step in microparticle formation when the organic/water or water/organic/water emulsion is charged to an aqueous sink. The cost of water treatment, as well as the cost of water itself, becomes a cost factor for manufacturing microparticles on a production level.

There exists a need for a process for preparing microparticles resulting in low residual solvent levels while lowering the amount of water necessary to complete the process steps, and, therefore, the cost of manufacturing.

SUMMARY

The present disclosure relates to emulsion-based (oil/water or water/oil or water/oil/water or oil/water/oil) processes for forming microparticles that utilize reduced water volumes. In addition, the disclosed processes provide microparticles having a reduced residual solvent level.

The present disclosure relates, in one aspect, to a method for determining the lower amount of extraction phase solution or solvent necessary for forming microparticles when the process involves at least one solvent-extraction process step. The methods of the present disclosure result in microparticles having a residual solvent level less than or equal to about 3% by weight. In another embodiment the residual solvent level is less than or equal to about 2% by weight. The use of the Extraction Ratio allows the formulator to predetermine the amount of extraction phase solution or solvent needed to produce the low residual solvent level microparticles.

The present disclosure further relates to a process for forming microparticles utilizing matrix-forming polymers that, when used in the dispersed phase, allow for the preparation of low residual solvent level microparticles. These matrix forming polymers include:
a) copolymers comprising a hydrophilic block and a hydrophobic block;
b) admixtures of:
  i) copolymers comprising a hydrophilic block and a hydrophobic block; and
  ii) biocompatible and/or biodegradable polymers; and
c) admixtures of:
  i) hydrophilic polymers; and
  ii) biocompatible and/or biodegradable polymers.

Additional advantages of the disclosure will be set forth in part in the description that follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DESCRIPTION OF THE FIGURES

The accompanying figures, which are incorporated in and constitute a part of this specification, illustrate several aspects described below.

DETAILED DISCLOSURE

Figure 1:
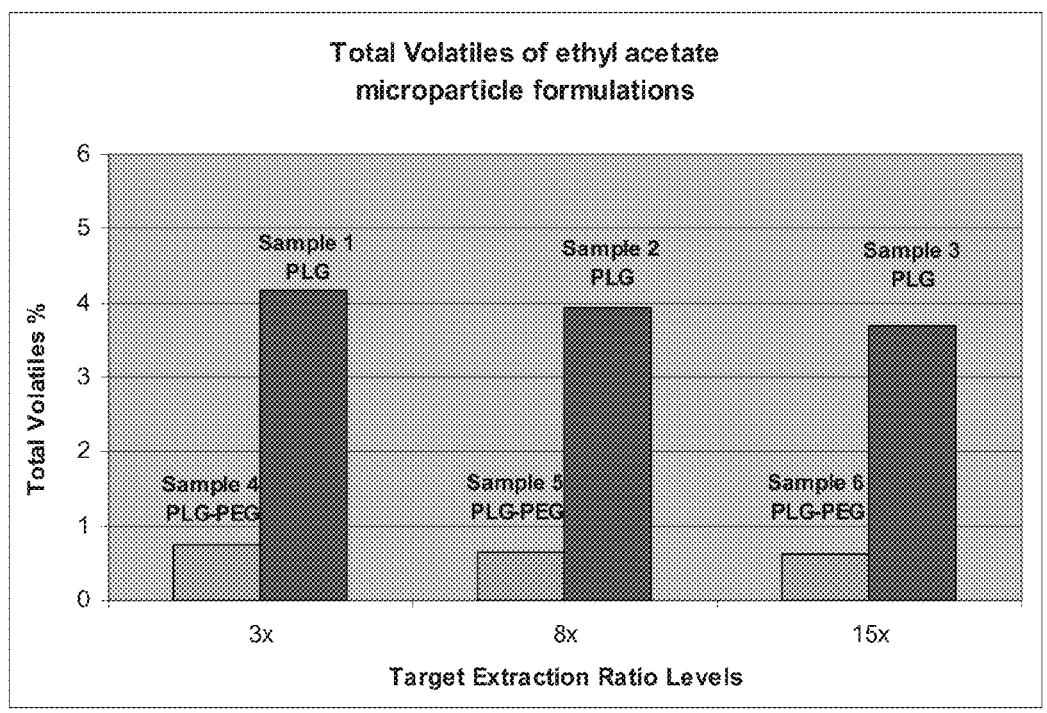
FIG. 1 depicts the results provided in Table 3 wherein ethyl acetate is used as the solvent for the dispersed phase.

Before the present copolymers, polymer admixtures, compounds, compositions, and/or methods are disclosed and described, it is to be understood that the aspects described herein are not limited to specific compounds, synthetic methods, or uses as such can, of course, vary. It is also to be understood that the terminology used herein is for the purpose of describing particular aspects only and, unless specifically defined herein, is not intended to be limiting.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

By "contacting" is meant the physical contact of at least one substance to another substance.

By "sufficient amount" and "sufficient time" means an amount and time needed to achieve the desired result or results, e.g., dissolve a portion of the polymer.

"Biocompatible" as used herein means the biological response to the material or device is appropriate for the device's intended application in vivo. Any metabolites of these materials should also be biocompatible.

"Biodegradable" generally refers to a biocompatible material that will degrade or erode under physiologic conditions to smaller units or chemical species that are, themselves, biocompatible or non-toxic to the subject and capable of being metabolized, eliminated, or excreted by the subject.

"Polymer excipient" as used herein refers to homopolymer or copolymer or blends comprising homopolymers or copolymers and combination thereof that are used as the microparticle wall forming or matrix materials. This term should be distinguished from the term "excipient" as defined herein below.

"Polymer" as used herein refers to any type of polymer including, for example, a homopolymer, a copolymer, a block copolymer, a random copolymer, and the like.

"Absorbable" as used herein means the complete degradation of a material in vivo and elimination of its metabolites from an animal or human subject.

"Molecular weight" as used herein, unless otherwise specified, refers generally to the relative average molecular weight of the bulk polymer. In practice, molecular weight can be estimated or characterized in various ways including gel permeation chromatography (GPC) or capillary viscometry. GPC molecular weights are reported as the weight-average molecular weight (Mw) or as the number-average molecular weight (Mn). Capillary viscometry provides estimates of molecular weight as the Inherent Viscosity (IV) determined from a dilute polymer solution using a particular set of concentration, temperature, and solvent conditions. Unless otherwise specified, IV measurements are made at 30° C. on solutions prepared in chloroform at a polymer concentration of 0.5 g/dL.

"Controlled release" as used herein means the use of a material to regulate the release of another substance.

"Bioactive agent" is used herein to include a compound of interest contained in or on the microparticle such as therapeutic or biologically active compounds that may be used internally or externally as a medicine for the treatment, diagnosis, cure, or prevention of a disease or disorder. Examples can include, but are not limited to, drugs, small-molecule drugs, peptides, proteins, oligonucleotides. "Bioactive agent" includes a single such agent and is also intended to include a plurality of bioactive agents including, for example, combinations of 2 or more bioactive agents.

"Excipient" is used herein to include any other compound or additive that can be contained in or on the microparticle that is not a therapeutically or biologically active compound. As such, an excipient should be pharmaceutically or biologically acceptable or relevant (for example, an excipient should generally be non-toxic to the subject). "Excipient" includes a single such compound and is also intended to include a plurality of excipients. This term should be distinguished from the term "polymer excipients" as defined above.

"Agent" is used herein to refer generally to compounds that are contained in or on a microparticle composition. Agent can include a bioactive agent or an excipient. "Agent" includes a single such compound and is also intended to include a plurality of such compounds.

The term "microparticle" is used herein to include nanoparticles, microspheres, nanospheres, microcapsules, nanocapsules, and particles, in general. As such, the term microparticle refers to particles having a variety of internal structure and organizations including homogeneous matrices such as microspheres (and nanospheres) or heterogeneous core-shell matrices (such as microcapsules and nanocapsules), porous particles, multi-layer particles, among others. The term "microparticle" refers generally to particles that have sizes in the range of about 10 nanometers (nm) to about 2 mm (millimeters).

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixtures.

Enantiomeric species may exist in different isomeric or enantiomeric forms. Unless otherwise specified, enantiomeric species discussed herein without reference to their isomeric form shall include all various isomeric forms as well as racemic mixtures of isomeric forms. For example, reference to lactic acid shall herein include L-lactic acid, D-lactic acid, and racemic mixtures of the L- and D-isomers of lactic acid; reference to lactide shall herein include L-lactide, D-lactide, and DL-lactide (where DL-lactide refers to racemic mixtures of the L- and D-isomers of lactide); similarly, reference to poly(lactide) shall herein include poly(L-lactide), poly(D-lactide) and poly(DL-lactide); similarly, reference to poly(lactide-co-glycolide) will herein include poly(L-lactide-co-glycolide), poly(D-lactide-co-glycolide), and poly (DL-lactide-co-glycolide); and so on.

The present disclosure relates to processes that utilize a reduced amount of water for forming microparticles having a residual solvent level of less than or equal to about 3% by weight. The disclosed process is adaptable to any emulsion-based process, for example, oil/water, water/oil, water/oil/water, or oil/water/oil processes. The disclosed process utilizes homopolymers, copolymers, and polymer admixtures that result in microparticles having a residual solvent level less than or equal to about 3% by weight, while utilizing a reduced amount of water during the process.

Emulsion-based processes are well known and involve the preparation, by one means or another, of a liquid-liquid dispersion. These dispersions comprise a first phase and a second phase. The first phase, known as the "dispersed phase" (dispersed phase) or "dispersed phase solution," is discontinuous in the second phase, known as the "continuous phase" or "continuous phase solution." Once formed, this emulsion is then further diluted with an additional solvent or solution, known as the "extraction phase" (EP) or "extraction solution." The solvent used for the dispersed phase is soluble in the extraction phase, however, some solvents are more soluble in the extraction phase or extraction solution than others.

The dispersed phase of the disclosed process comprises a matrix-forming polymer as further described herein. The matrix-forming polymer is dissolved or dispersed in a solvent to form a dispersed phase or a dispersed solution. When the dispersed phase/continuous phase emulsion is combined with the extraction phase, the resulting loss of solvent from the dispersed phase into the extraction phase causes discontinuous droplets of the dispersed phase to harden into polymer-rich microparticles.

The state of the art processes extract the solvent, typically an organic solvent, from the dispersed phase of an oil-in-water emulsion into a large volume of an extraction phase that in most instances is water, thereby forming droplets that form microparticles. This aqueous "sink" contains volumes far in excess of the amount we have now found to be necessary to fully dissolve or to fully saturate the extraction phase with the solvent from the dispersed phase. This large excess quantity of water can pose a challenge as the size of production is scaled-up since it will require large scales of operation and processing equipment, generate large volumes of processing effluent, result in long processing times, require large quantities of processing raw materials (such as water), and, correspondingly, will generate large quantities of waste. Therefore, the disclosed processes that provide for low residual solvent levels in the resulting microparticle product, while utilizing lower quantities of extraction solution during the solvent-extraction step, are advantageous to the formulator.

Non-water miscible solvents are not all soluble in water to the same extent. For example, ethyl acetate is more soluble in water than methylene chloride; therefore, a larger volume of water is needed to extract a like amount of methylene chloride than ethyl acetate. The disclosed processes, regardless of which solvent comprises the dispersed phase, result in lower water usage.

For the purposes of the present disclosure, the amount of water (or solvent/water admixture) that is necessary in order to provide the microparticle forming polymer or polymers can be estimated for each solvent by the Extraction Ratio. The Extraction Ration (ER) is defined herein as the number of excess volumes of extraction phase necessary to fully dissolve (at saturation) the quantity of solvent that comprises the dispersed phase. The Extraction Ratio, ER, can be expressed by the formula (1):

$$ER = \frac{W_{EP\,solvent,total}}{W_{DP\,solvent,total}/S} \quad (1)$$

wherein $W_{DP\,solvent,\,total}$ is the total combined weight of the solvent or solvents used in the process. As will be disclosed further, this solvent or solvents is not limited to the solvent used solely in forming the dispersed phase. $W_{EP\,solvent,\,total}$ is the total combined weight of the solvent, typically aqueous-based, that is used to extract the solvent from the dispersed phase thus forming the microparticles. S is the saturation solubility of the dispersed phase solvent in the extraction phase solvent system expressed in grams of dispersed phase solvent per grams of extraction phase solvent.

As discussed herein above, a typical process involves forming an oil-in-water emulsion to prepare microparticles. In this embodiment, the dispersed phase solvent is typically an organic solvent (the oil phase) and the extraction phase solvent is water or a mixture of water and a fully water-miscible solvent. In this case, the Extraction Ratio can be expressed by equation (2):

$$ER = \frac{W_{water,total}}{W_{organic\,solvent,total}/S} \quad (2)$$

wherein:
$W_{organic\,solvent,\,total}$ is the total weight of the dispersed phase organic solvent;
$W_{water,\,total}$ is the combined weight in the solvent-extraction system of the aqueous extraction phase; and
S is the saturation solubility (in g/g) of the organic dispersed phase solvent in the aqueous extraction phase solvent.

The Extraction Ratio can be utilized by the artisan for determining the excess amount of dispersed phase solution that is necessary to determine the volume of the extraction phase. The ER value provides the minimal amount of water necessary for extracting a given amount of solvent. For example, a process operating at an ER value of 20 contains 20-times more extraction solvent than is theoretically needed to fully dissolve, at saturation, the amount of a particular dispersed phase solvent present in the system.

State of the art processes utilize extraction solution volumes wherein the Extraction Ratios are at or above 10. Under these conditions the $W_{water,\,total}$, can be expressed as follows:

$$W_{water,total} = ER\left[\frac{W_{organic\,solvent,total}}{S}\right] \geq 10\left[\frac{W_{organic\,solvent,total}}{S}\right] \quad (3)$$

The disclosed process provides methods for forming microcapsules wherein the Extraction Ratios are less than about 10. This is achieved by selecting as the polymer excipient one of the following systems as described further herein below:
a) copolymers comprising a hydrophilic block (or blocks) and a hydrophobic block (or blocks);
b) polymer excipient comprising:
   i) copolymers comprising a hydrophilic block and a hydrophobic block; and
   ii) biocompatible and/or biodegradable polymers; and
c) polymer excipient comprising:
   i) hydrophilic polymers; and
   ii) biocompatible and/or biodegradable polymers.

A first embodiment of the disclosed process comprises:
a) determining the weight, $W_{water,\,total}$, of water for use as the extraction phase solvent by utilizing an Extraction Ratio, ER, of less than or equal to about 10, wherein $W_{water,\,total}$ is defined by Equation (4):

$$W_{water,total} \leq ER\left[\frac{W_{organic\,solvent,total}}{S}\right] \quad (4)$$

wherein $W_{organic\,solvent,\,total}$ is the total combined weight of solvent or solvents used to form the dispersed phase; S is the solubility of the dispersed phase organic solvent in the extraction phase solution used in the solvent-extraction step of the process used in forming the microparticles; and
b) forming microparticles using a weight of water, $W_{water,\,total}$, in an oil/water or water/oil/water emulsion extraction process;

wherein the microparticles have less than or equal to about 3 wt % residual solvent. In one aspect of this embodiment, the level of residual solvent is less than or equal to about 2 wt % of the microparticle. And in yet a further aspect, the residual solvent level of the microparticle is less than or equal to about 1.5 wt %.

Another embodiment of the disclosed process comprises:
(a) providing a dispersed phase comprising a composition containing a polymer excipient of the present invention in a weight amount of a dispersed phase solvent, $W_{DP\ solvent}$;
(b) combining the dispersed phase with a continuous phase processing medium to form an emulsion wherein the dispersed phase is a discontinuous phase in the continuous phase;
(c) combining the emulsion formed in (b) with a weight amount of an extraction phase solvent, $W_{EP\ solvent}$, thereby forming microparticles; and
(d) isolating the microparticles;

wherein the amount of residual dispersed phase solvent present in the isolated microparticles is less than or equal to about 3 wt %.

In the above embodiment, step (c) serves as a solvent-extraction step. The total combined weight of extraction phase solvent present in the process during the solvent-extraction step is the combined total amount of the extraction phase solvent used in all steps of the process, for example, steps (a), (b), and (c). Total amount of extraction phase solvent is $W_{EP\ solvent,\ total}$ defined by the formula:

$$W_{EP solvent, total} \leq 10\left[\frac{W_{DP solvent, total}}{S}\right]$$

wherein $W_{DP\ solvent,\ total}$ is the combined total amount of a particular dispersed phase solvent present during the solvent-extraction step, for example, steps (a), (b), and (c), and S is the solubility (in g/g) of the dispersed phase solvent in the final composition of the extraction phase solution used during the solvent-extraction step.

A further embodiment of the disclosed processes comprises:
(a) providing a dispersed phase comprising a composition containing a polymer excipient of the present invention in a weight amount of a dispersed phase solvent, $W_{DP\ solvent}$;
(b) combining the dispersed phase formed in (a) with an aqueous continuous phase processing medium comprising a weight amount of water, $W_{CP\ solvent}$, to form an emulsion, the emulsion having a discontinuous organic phase and an continuous aqueous phase;
(c) combining the emulsion formed in (b) with an additional weight amount of an aqueous extraction phase comprising a weight amount of water, $W_{EP\ solvent}$, thereby forming microparticles; and
(d) isolating the microparticles.

One aspect of this embodiment comprises:
(a) providing a dispersed phase comprising a composition containing a polymer excipient of the present invention in a weight amount of an organic solvent, $W_{DP\ organic\ solvent}$;
(b) combining the dispersed phase formed in (a) with an aqueous continuous phase processing medium comprising a weight amount of water, $W_{CP\ solvent}$, to form an emulsion, the emulsion having a discontinuous organic phase and an continuous aqueous phase;
(c) combining the emulsion formed in (b) with an additional weight amount of an aqueous extraction phase comprising a weight amount of water, $W_{EP\ solvent}$, wherein the dispersed phase is in the form of droplets and wherein the solvent that comprises the droplets is extracted into the aqueous extraction phase, thereby forming microparticles; and
(d) isolating the microparticles;

wherein the amount of residual organic solvent present in the isolated microparticles is less than or equal to about 3 wt %. The total combined weight of water in the extraction phase during the solvent-extraction step is the combined total amount of the extraction phase solvent used in all steps of the process, for example, steps (a), (b), and (c). Total amount of extraction phase solvent is $W_{W,\ total}$ defined by the formula:

$$W_{W, total} \leq 10\left[\frac{W_{ORG, total}}{S}\right]$$

wherein $W_{ORG,\ total}$ is the combined total amount of a particular dispersed phase solvent present during the solvent-extraction step, for example, steps (a), (b), and (c), and S is the solubility (in g/g) of the dispersed phase solvent in the final composition of the extraction phase solution used during the solvent-extraction step.

In the above aspect, steps (c) and (d) are the solvent-extraction steps. The total combined weight of extraction phase solvent present in the process during the solvent-extraction step is the combined total amount of the extraction phase solvent used in all steps of the process, for example, steps (a), (b), and (c).

One further aspect of the disclosed processes relates to microparticles that deliver one or more bioactive agents. For example, a process comprising:
(a) providing a composition comprising a polymer excipient of the present invention and one or more bioactive agents in a weight amount, $W_{DP\ organic\ solvent}$, of an organic solvent to form a dispersed phase solution;
(b) combining the dispersed phase solution formed in (a) with a continuous phase processing medium comprising a weight amount of water, $W_{CP\ solvent}$, to form an emulsion, the emulsion having a discontinuous organic phase and an continuous aqueous phase;
(c) combining the emulsion formed in (b) with an extraction phase solution comprising a weight amount of water, $W_{EP\ solvent}$, to form microparticles; and
(d) isolating the microparticles.

wherein the amount of residual organic solvent present in the isolated microparticles is less than or equal to about 3 wt %. The total combined weight of water in the extraction phase during the solvent-extraction step is the combined total amount of the extraction phase solvent used in all steps of the process, for example, steps (a), (b), and (c). Total amount of extraction phase solvent is $W_{W,\ total}$ defined by the formula:

$$W_{W, total} \leq 10\left[\frac{W_{ORG, total}}{S}\right]$$

wherein $W_{ORG,\ total}$ is the combined total amount of a particular dispersed phase solvent present during the solvent-extraction step, for example, steps (a), (b), and (c), and S is the solubility (in g/g) of the dispersed phase solvent in the final composition of the extraction phase solution used during the solvent-extraction step. In step (b) of the above aspect, the organic dispersed phase solution is the discontinuous phase of the emulsion and the continuous processing solution is the continuous phase of the emulsion Another further aspect relates to a process comprising:
(a) providing a composition comprising a polymer excipient of the present invention and one or more bioactive agents in a weight amount, $W_{DP\ organic\ solvent}$, of an organic solvent to form a dispersed phase;
(b) combining the dispersed phase formed in (a) with a continuous phase processing medium comprising a weight amount of water, $W_{CP\ solvent}$, to form an emulsion, the emulsion having a discontinuous organic phase and an continuous aqueous phase;
(c) combining the emulsion formed in (b) with an additional weight amount of an aqueous extraction phase comprising a weight amount of water, $W_{EP\ solvent}$, wherein the dispersed phase is in the form of droplets and wherein the solvent that comprises the droplets is extracted into the aqueous extraction phase, thereby forming microparticles; and
(d) isolating the microparticles;

wherein the amount of residual organic solvent present in the isolated microparticles is less than or equal to about 3 wt %. The total combined weight of water in the extraction phase during the solvent-extraction step is the combined total amount of the extraction phase solvent used in all steps of the process, for example, steps (a), (b), and (c). Total amount of extraction phase solvent is $W_{W,\ total}$ defined by the formula:

$$W_{W,total} \leq 10\left[\frac{W_{ORG,total}}{S}\right]$$

wherein $W_{ORG,\ total}$ is the combined total amount of a particular dispersed phase solvent present during the solvent-extraction step, for example, steps (a), (b), and (c), and S is the solubility (in g/g) of the dispersed phase solvent in the final composition of the extraction phase solution used during the solvent-extraction step.

The following is another embodiment of the processes according to the present disclosure wherein one or more active ingredients are incorporated into the microparticle comprises:
(a) providing a composition comprising a polymer excipient of the present invention and ingredients chosen from bioactive agents, pharmaceutical agent, excipients, additives, or delivery agents, in a weight amount, $W_{DP\ organic\ solvent}$, of an organic solvent to form a dispersed phase;
(b) combining the dispersed phase formed (a) with a continuous phase processing medium comprising a weight amount of water, $W_{CP\ water}$, wherein the water is saturated with a weight amount, $W_{CP\ organic\ solvent}$, of the organic solvent used to prepare the dispersed phase in step (a) and optionally the continuous phase solution further comprises one or more processing aids, additives, or agents, to form an emulsion, the emulsion having a discontinuous organic phase and a continuous aqueous phase;
(c) combining the emulsion formed in (b) with an extraction phase solution comprising a weight amount of water, $W_{EP\ solvent}$, to form microparticles; and
(d) isolating the microparticles;

wherein the amount of residual organic solvent present in the isolated microparticles is less than or equal to about 3 wt %.

A further aspect relates to a process comprising:
(a) providing a composition comprising a polymer excipient of the present invention and ingredients chosen from bioactive agents, pharmaceutical agent, excipients, additives, or delivery agents, in a weight amount, $W_{DP\ organic\ solvent}$, of an organic solvent to form a dispersed phase;
(b) combining the dispersed phase formed (a) with a continuous phase processing medium comprising a weight amount of water, $W_{CP\ solvent}$, wherein the water is saturated with a weight amount, $W_{CP\ organic\ solvent}$, of the organic solvent used to prepare the dispersed phase in step (a) and optionally the continuous phase solution further comprises one or more processing aids, additives, or agents, to form an emulsion, the emulsion having a discontinuous organic phase and a continuous aqueous phase;
(c) combining the emulsion formed in (b) with an additional weight amount of an aqueous extraction phase comprising a weight amount of water, $W_{EP\ solvent}$, wherein the dispersed phase is in the form of droplets and wherein the solvent that comprises the droplets is extracted into the aqueous extraction phase, thereby forming microparticles; and
(d) isolating the microparticles;

wherein the amount of residual organic solvent present in the isolated microparticles is less than or equal to about 3 wt %. In the above aspects, additives to the continuous phase can be emulsifiers or emulsification agents.

A further embodiment of the disclosed processes that relates to water/oil/water (double-emulsion) processes comprises:
a)(i) providing a composition comprising a polymer excipients of the present invention in a weight amount, $W_{DP\ organic\ solvent}$, of an organic solvent to form an organic phase;
a)(ii) providing one or more actives dissolved or dispersed in a weight amount of water, $W_{DP\ water}$, to form an aqueous phase;
a)(iii) combining the organic phase formed in (a)(i) and the aqueous phase formed in (a)(ii) to form a water-in-oil emulsion wherein the discontinuous phase is the aqueous phase and the continuous phase is the organic phase wherein the resulting water-in-oil emulsion is a dispersed phase solution;
b) combining the dispersed phase solution formed in (a)(iii) with a continuous phase processing medium comprising a weight amount of water, $W_{CP\ solvent}$, wherein the water is saturated with a weight amount, $W_{CP\ organic\ solvent}$, of the organic solvent that comprises organic phase formed in (a)(i), and wherein the continuous phase solution further comprises one or more processing or emulsification aids, to form an emulsion whereby the organic dispersed phase solution from step (a)(iii) is discontinuous in the continuous phase solution;
c) combining the emulsion formed in step (b) with an extraction phase solution comprising a weight amount of water, $W_{EP\ solvent}$, thereby forming microparticles; and
d) isolating the microparticles;

wherein the total amount of organic solvent present in the system during solvent-extraction is the combined total amount of organic solvent added into the process from steps (a), (b), and (c) and is designated as $W_{org,\ total}$ and the total amount of water used in the process is the combined total amount added into the process from steps (a), (b), and (c) and is designated as $W_{w, total}$ and can be calculated by the formula:

$$W_{W,total} \le 10\left[\frac{W_{ORG,total}}{S}\right].$$

A further embodiment of the disclosed processes that relates to processes that use multiple organic solvents in the preparation of the dispersed phase whereby the total amount of water used in the process during the solvent-extraction step is the greater amount as determined from calculations made for each individual solvent used in the process using the following formula:

$$W_{W,total} \le 10\left[\frac{W_{ORG,total}}{S}\right]$$

whereby $W_{org, total}$ is the total amount of one individual organic solvent added into the process from steps (a), (b), and (c) $W_{w, total}$ is, then, the combined total weight amount of water added to the process during the solvent-extraction step as is introduced during steps (a), (b), and (c).

The present disclosure solves the problem of obtaining microparticles having less than or equal to about 3 wt % wherein a large volume of water is used in the process of obtaining low residual solvent volume microparticles. In a further embodiment, the microparticles comprise less than or equal to about 2 wt % of residual solvent. In a still further embodiment, the microparticles comprise less than or equal to about 1.5 wt % of residual solvent. In a yet further embodiment, the microparticles comprise less than or equal to about 1 wt % of residual solvent.

The process of the present disclosure can be used to form the herein described low residual solvent level microparticles when employing the present invention which include the following polymer excipients: non-water soluble copolymers comprising one or more hydrophobic component (blocks) and one or more hydrophilic component (blocks) wherein the copolymer is non-water soluble; polymer excipients of copolymers comprising a hydrophilic block and a hydrophobic block and biocompatible and/or biodegradable polymers; and, admixtures of hydrophilic (water soluble) polymers and biocompatible and/or biodegradable polymers.

One embodiment of the copolymers comprising the compositions that comprise step (a) of the disclosed process, comprise polymer excipient of:
i) one or more hydrophobic component (blocks) of a biocompatible polymer; and
ii) one or more hydrophilic component (blocks) of a hydrophilic (water-soluble) biocompatible polymer;
wherein the non-water soluble copolymer has a molecular weight of from about 1,000 daltons to about 2,000,000 daltons.

One embodiment of the copolymers comprising the compositions that comprise step (a) of the disclosed process, comprise polymer excipient:
i) a hydrophobic component (block) comprising biocompatible and biodegradable polymer chemistries including polyesters, polyanhydrides, polyorthoesters, polyphosphazenes, polyphosphates, polyphosphoesters, polydioxanones, polyphosphonates, polyhydroxyalkanoates, polycarbonates, polyalkylcarbonates, polyorthocarbonates, polyesteramides, polyamides, polyamines, polypeptides, polyurethanes, polyetheresters, or combinations thereof, the hydrophobic component having a molecular weight from about 500 daltons to about 2,000,000 daltons; and
ii) a hydrophilic component (block) comprising hydrophilic (water-soluble) materials including polyalkylene glycols, polyalkylene oxides, polypeptides, polysaccharides, polyvinyl pyrrolidones, proteins, modified polysaccharides (and the like) having a molecular weight of from about 100 daltons to about 100,000 daltons;
wherein the water-insoluble copolymer has a molecular weight of from about 1,000 daltons to about 2,000,000 daltons.

One embodiment of the polymer excipient comprising the compositions that comprise step (a) of the disclosed process, comprise:
i) a hydrophobic component (block) comprising lactide (which herein includes L-lactide or D-lactide or DL-lactide), glycolide, caprolactone, or hydroxybutyrate, or hydroxyvalerates (or combinations thereof), the hydrophobic component having a molecular weight from about 500 daltons to about 2,000,000 daltons; and
ii) a hydrophilic component (block) comprising a polyalkylene glycol having a molecular weight of from about 100 daltons to about 100,000 daltons;
wherein the water-insoluble copolymer has a molecular weight of from about 1,000 daltons to about 2,000,000 daltons.

One embodiment of the copolymers comprising the compositions that comprise step (a) of the disclosed process, comprise:
i) a hydrophobic component (block) comprising lactide, glycolide, caprolactone, hydroxybutyrate, or hydroxyvalerates (or combinations thereof), the hydrophobic component having a molecular weight from about 500 daltons to about 2,000,000 daltons; and
ii) a hydrophilic component (block) comprising a polyvinyl pyrrolidone having a molecular weight of from about 100 daltons to about 100,000 daltons;
wherein the water-insoluble copolymer has a molecular weight of from about 1,000 daltons to about 2,000,000 daltons.

One embodiment of the polymer excipient comprising the compositions that comprise step (a) of the disclosed processes, comprise:
i) a non-water soluble copolymer containing one or more hydrophobic blocks and one or more hydrophilic blocks having a molecular weight from about 500 daltons to about 2,000,000 daltons; and
ii) a non-water soluble biocompatible or biodegradable polymer.

One embodiment of the polymer excipient comprising the compositions that comprise step (a) of the disclosed processes, comprise:
i) a non-water soluble copolymer or homopolymer having a molecular weight from about 500 daltons to about 2,000,000 daltons; and
ii) a water-soluble copolymer or homopolymer having a molecular weight of from about 100 daltons to about 100,000 daltons.

Another embodiment of the polymer excipient comprising the compositions that comprise step (a) of the disclosed processes, comprise:
i) a non-water soluble copolymer or homopolymer comprising biocompatible and biodegradable polymer chemistries including polyesters, polyanhyrdides, polyorthoesters, polyphosphazines, polyphosphoesters, polyesteramides, polydioxanones, polycarbonates, polyamides, or polyorthocarbonates, (or combinations thereof), the hydrophobic component having a molecular weight from about 500 daltons to about 2,000,000 daltons; and ii) a water-soluble copolymer or homopolymer comprising a polyalkylene glycol having a molecular weight of from about 100 daltons to about 100,000 daltons.

Another embodiment of the polymer excipient comprising the compositions that comprise step (a) of the disclosed processes, comprise:

i) a non-water soluble copolymer or homopolymer comprising biocompatible and biodegradable polymer chemistries including polyesters, polyanhyrdides, polyorthoesters, polyphosphazines, polyphosphoesters, polyesteramides, polydioxanones, polycarbonates, polyamides, or polyorthocarbonates, (or combinations thereof), the hydrophobic component having a molecular weight from about 500 daltons to about 2,000,000 daltons; and ii) a water-soluble copolymer or homopolymer comprising a polyvinylpyrrolidone having a molecular weight of from about 100 daltons to about 100,000 daltons.

Another embodiment of the polymer excipient comprising the compositions that comprise step (a) of the disclosed processes, comprise:

i) a non-water soluble copolymer or homopolymer comprising biocompatible and biodegradable polymer chemistries including polyesters, polyanhyrdides, polyorthoesters, polyphosphazines, polyphosphoesters, polyesteramides, polydioxanones, polycarbonates, polyamides, or polyorthocarbonates, (or combinations thereof), the hydrophobic component having a molecular weight from about 500 daltons to about 2,000,000 daltons; and ii) a water-soluble copolymer or homopolymer comprising a polysaccharide or modified polysaccharide having a molecular weight of from about 100 daltons to about 100,000 daltons.

Another embodiment of the polymer excipient comprising the compositions that comprise step (a) of the disclosed processes, comprise:

i) a non-water soluble copolymer or homopolymer comprising biocompatible and biodegradable polymer chemistries including polyesters, polyanhyrdides, polyorthoesters, polyphosphazines, polyphosphoesters, polyesteramides, polydioxanones, polycarbonates, polyamides, or polyorthocarbonates (or combinations thereof), the hydrophobic component having a molecular weight from about 500 daltons to about 2,000,000 daltons; and ii) a water-soluble copolymer or homopolymer comprising a block copolymer of a polyester and a polyalkylene glycol having a molecular weight of from about 100 daltons to about 100,000 daltons.

The polymer excipients are suitable for use in forming microparticles, for forming microparticles optionally comprising one or more active agents or one or more additives or agents, or combinations thereof, or for forming placebo microparticles; or for forming microparticles comprising one or more biologically compatible ingredients aiding in the delivery or compatibility of the one or more active agents; or for forming microparticles comprising bioactive agents and/or other agents or additives that might be used for medical or clinical or diagnostic or therapeutic purposes.

The microparticles formed by the disclosed processes can comprise less than or equal to about 3 wt % residual solvent, preferably less than or equal to about 2 wt % of a residual solvent. In one embodiment, the microparticles can comprise less than or equal to about 2.75 wt % residual solvent. In one embodiment, the microparticles can comprise less than or equal to about 2.50 wt % residual solvent. In another embodiment, the microparticles can comprise less than or equal to about 2.25 wt % residual solvent. In another embodiment, the microparticles can comprise less than or equal to about 2 wt % residual solvent. In one embodiment, the microparticles can comprise less than or equal to about 1.75% of a residual solvent. In another embodiment, the microparticles can comprise less than or equal to about 1.5% of a residual solvent. In a further embodiment, the microparticles can comprise less than or equal to about 1.25% of a residual solvent. In a still further embodiment, the microparticles can comprise less than or equal to about 1% of a residual solvent.

The microparticles formed by the disclosed processes can comprise less than or equal to about 2% of residual moisture. In one embodiment, the microparticles can comprise less than or equal to about 1.75% or residual moisture. In another embodiment, the microparticles can comprise less than or equal to about 1.5% or residual moisture. In a further embodiment, the microparticles can comprise less than or equal to about 1.25% or residual moisture. In a still further embodiment, the microparticles can comprise less than or equal to about 1% or residual moisture.

Copolymers

The microparticles of the present disclosure can be prepared from non-water soluble copolymers that comprise one or more hydrophilic components (blocks) and one or more hydrophobic components (blocks). For example, a microparticle prepared by the disclosed process can be comprised entirely of a block copolymer that is essentially non-water soluble that is formed from at least one a hydrophobic component (block) and at least one hydrophilic component (block).

One aspect of the low residual solvent level microparticles relates to microparticles comprising block copolymers comprising a hydrophilic block and a hydrophobic block, for example, microparticles wherein:

a) the hydrophilic block comprises one or more of the following:
  i) polyalkylene glycols, for example, polyethylene glycol, polypropylene glycol, and the like;
  ii) polyvinyl pyrrolidone and derivatives thereof,
  iii) naturally occurring, synthetic, or modified polysaccharides;
  iv) peptides and/or proteins; and
  v) other hydrophilic units, oligomers, homopolymers, or copolymers; and b) the hydrophobic block comprises one or more of the following:
  i) lactide, glycolide, caprolactone, and mixtures thereof,
  ii) polyester, polyhydroxy acids, polyanhydrides, polyorthoesters, polyetheresters, polyesteramides, polyphosphazines, polyphosphoesters, polyphosphates, polyphosphonates, polycarbonates, polyorthocarbonates, polyamides, or copolymers thereof.

Another aspect of the low residual solvent level microparticles relates to microparticles comprising polymer excipient comprising, for example:

a) a component chosen from:
  i) poly(lactide)-co-(polyalkylene oxide);
  ii) poly(lactide-co-glycolide)-co-(polyalkylene oxide);
  iii) poly(lactide-co-caprolactone)-b-(polyalkylene oxide);
  iv) poly(lactide-co-glycolide-co-caprolactone)-b-(polyalkylene oxide);
  v) poly(lactide)-co-(polyvinyl pyrrolidone);
  vi) poly(lactide-co-glycolide)-co-(polyvinyl pyrrolidone);
  vii) poly(lactide-co-caprolactone)-b-(polyvinyl pyrrolidone); and
  viii) poly(lactide-co-glycolide-co-caprolactone)-b-(polyvinyl pyrrolidone); and
b) a component chosen from:
  i) poly(lactide);
  ii) poly(lactide-co-glycolide);
  iii) poly(lactide-co-caprolactone);
  iv) poly(lactide-co-glycolide-co-caprolactone);
  v) poly(glycolide-co-caprolactone); and
  vi) poly(caprolactone).

A further aspect of the low residual solvent level microparticles relates to microparticles comprising polymer excipient, for example:
a) a component chosen from:
  i) polyalkylene glycols;
  ii) polyvinyl pyrrolidones; and
  iii) other hydrophilic polymers or copolymers; and
b) a component chosen from biodegradable:
  i) polyesters;
  ii) polyhydroxy acids;
  iii) polyanhydrides;
  iv) polyorthoesters,
  v) polyetheresters,
  vi) polyesteramides,
  vii) polyphosphazines,
  viii) polyphosphoesters,
  ix) polyphosphates,
  x) polyphosphonates,
  xi) polycarbonates,
  xii) polyorthocarbonates,
  xiii) polyamides, or
  xiv) copolymers thereof.

The molecular weights of the hydrophobic components of the copolymers of the present disclosure are from about 500 daltons to about 2,000,000 daltons. The molecular weights of the hydrophilic components of the copolymers of the present disclosure are from about 100 daltons to about 100,000 daltons.

In one embodiment, the molecular weight of the hydrophobic component can be from about 2,000 daltons to about 200,000 daltons. In another embodiment, the molecular weight of the hydrophobic component can be from about 500 daltons to about 5,000 daltons. Wherein a further aspect of this embodiment comprises copolymers wherein the hydrophobic component has an average molecular weight of from 500 daltons to 1,500 daltons. In a yet further embodiment, the molecular weight of the hydrophobic component can be from about 1,000 daltons to about 200,000 daltons. In another further embodiment, the molecular weight of the hydrophobic component can be from about 4,000 daltons to about 150,000 daltons. And in a yet further embodiment, the molecular weight of the hydrophobic component can be from about 4,000 daltons to about 100,000 daltons. The molecular weight of the hydrophilic component of the copolymers of the present disclosure can be from about 100 daltons to about 100,000 daltons. In another embodiment, the molecular weight of the hydrophilic component can be from about 100 daltons to about 40,000 daltons. In yet another embodiment, the molecular weight of the hydrophilic component can be from about 100 daltons to about 8,000 daltons. A further embodiment comprises a hydrophilic component having a molecular weight of from about 1,000 daltons to about 8,000 daltons. A yet another further embodiment comprises a hydrophilic component having a molecular weight of from about 1,000 daltons to about 6,000 daltons. In a still yet another embodiment comprises a hydrophilic component having a molecular weight of from about 10,000 daltons to about 100,000 daltons. In a still yet further embodiment comprises a hydrophilic component having a molecular weight of from about 5,000 daltons to about 50,000 daltons. Another further embodiment comprises a hydrophilic component having a molecular weight of from about 3,000 daltons to about 12,000 daltons. A still further embodiment comprises a hydrophilic component having a molecular weight of from about 400 daltons to about 4,000 daltons.

The copolymer average molecular weights can be obtained be Gel Permeation Chromatography (GPC), for example, as described by L. H. Sperling of the Center for Polymer Science and Engineering & Polymer Interfaces Center, Materials Research Center, Department of Chemical Engineering and Materials Science and Engineering Department, Lehigh University, 5 E. Packer Ave., Bethlehem, Pa. 18015-3194, as first described in: ACS Division of Polymeric Materials: Science and Engineering (PMSE), 81, 569 (1999).

Alternatively the molecular weights can be described by their measured Inherent Viscosity (IV) as determined by capillary viscometry. Molecular weights of the polymers or copolymers described herein can be about 0.05 dL/g to about 2.0 dL/g wherein dL is deciliter. In another embodiment the inherent viscosity can be from about 0.05 dL/g to about 1.2 dL/g. In a further embodiment the inherent viscosity can be form about 0.1 dL/g to about 1.0 dL/g. A yet further embodiment of the polymers and copolymers of the present disclosure can have an inherent viscosity of from about 0.1 dL/g to about 0.8 dL/g. And yet another embodiment of the polymers and copolymers of the present disclosure can have an inherent viscosity of from about 0.05 dL/g to about 0.5 dL/g. Alternatively, the formulator can express the inherent viscosity in $cm^3/g$ if convenient.

As described herein below, when the processes comprise polymer excipient in step (a) and wherein the polymer excipient comprises one or more biodegradable polymers, inter alia, a polyester, poly(lactide-co-glycolide), polylactide, polyglycolide, polycaprolactone, polyhydroxybutyrate, the polymer can have an intrinsic viscosity of from about 0.05 dL/g to about 2.0 dL/g. In one embodiment, the intrinsic viscosity can be from about 0.05 dL/g to about 1.5 dL/g, while in a further embodiment the intrinsic viscosity can be from about 0.05 dL/g to about 1.0 dL/g, in a yet further embodiment, the intrinsic viscosity can be from about 0.05 dL/g to about 0.75 dL/g, while in a still further embodiment, the intrinsic viscosity can be from about 0.05 dL/g to about 0.5 dL/g. Non-limiting examples of useful intrinsic viscosity ranges include from about 0.05 dL/g to about 0.25 dL/g and from about 0.05 dL/g to about 0.15 dL/g. The intrinsic viscosity measurements disclosed herein are taken in chloroform at a concentration of 0.5 g/dL at 30° C.

The following are non-limiting examples of homopolymers, copolymers, and mixtures thereof that can be used to form microparticles having low residual solvent levels by the disclosed processes.

Copolymers of Hydroxy Acids and Polyalkylene Glycols

A first aspect of the copolymers that can comprise the microparticles formed by the disclosed processes, are water insoluble copolymers containing at least one hydrophobic component (block) and at least one hydrophilic component (block). The hydrophobic component can comprise one or more hydroxy acids. The hydrophobic component can be a block copolymer of two or more hydroxy acids, or a homopolymer of one hydroxy acid.

Non-limiting examples of units that can form the hydrophobic component include units that can be derived from cyclic esters, for example:

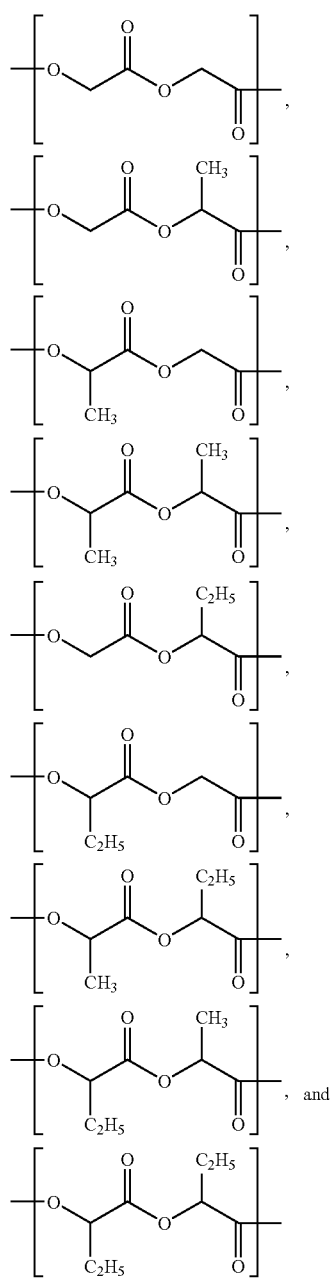

as well as units that can be derived from hydroxy acids or their corresponding lactones, for example,

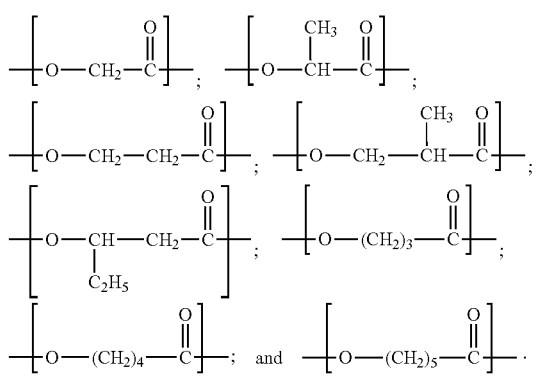

Non-limiting examples include units derived from valerolactone, caprolactone, and the like. The hydrophilic components that can comprise the copolymers of this embodiment are homopolymers, copolymers, or block copolymers of one or more polyalkylene glycols, polyvinylpyrrolidones, polysaccharides and the like.

Lactide/Glycolide/Polyalkyleneoxy Copolymers

A first embodiment of the copolymers according to the disclosed processes relates to copolymers comprising one or more poly(lactide-co-glycolide) or a poly(lactide) hydrophobic component and a polyalkyleneoxy hydrophilic component.

In one aspect the ratio of lactide to glycolide is from 50:50 to 100:0 (100:0 represents a hydrophobic component comprising only a homopolymer of lactide, i.e., poly(lactide)). In another aspect of this embodiment, the ratio of lactide to glycolide is 55:45, in a further aspect the ratio of lactide to glycolide is 75:25, in yet a further aspect the ratio of lactide to glycolide is 80:15. Other aspects include ratios of lactide to glycolide that are 60:40, 65:35, 70:30, 80:20, 90:10; and 95:05. However, the formulator can include any ratio of lactide to glycolide, for example, 62.5:37.5 lactide to glycolide. Poly-(lactide-co-glycolide) copolymers are also represented by the short hand notation PLG or in the instance wherein the ratio of lactide to glycolide is 100:0 (hydrophobic component comprises only poly(lactide) the hydrophobic component can be designated herein as PL.

The poly(lactide-co-glycolide) utilized as the hydrophobic component of this embodiment can either be prepared by the formulator using techniques well known to the artisan, for example, by the procedure disclosed in U.S. Pat. No. 6,747, 121 B2, included herein by reference in its entirety, or the formulator can purchase the hydrophobic component from one or more commercial sources.

When measured by GPC or SEC against polystyrene standards, the poly(lactide-co-glycolide) copolymers according to the present disclosure (prior to reaction with polyethylene glycol) exhibit a number average molecular weight as described herein above for hydrophobic components.

Non-limiting examples of commercial sources of copolymers or homopolymers comprising lactide and glycolide include Lakeshore polymers from Brookwood Pharmaceuticals (Birmingham, Ala.). A suitable product commercially available from Brookwood is a 50:50 poly(lactide-co-glycolide) known as 5050 DLG. This product has a mole percent composition of 50% lactide and 50% glycolide. Other suitable commercially available products are Lakeshore polymers 6535 DLG, 7525 DLG, 8515 DLG. Poly(lactide-co-glycolide) polymers are also commercially available from Boehringer Ingelheim (Germany) under its Resomer mark, e.g., PLGA 50:50 (RESOMER™ RG 502), and PLGA 75:25 (RESOMER™ RG 752). These copolymers are available in a wide range of molecular weights and ratios of lactide to glycolide.

The hydrophilic component of this embodiment comprises one or more polyalkyleneoxy or polyoxyalkylene units. The terms "polyalkyleneoxy" or "polyoxyalkylene" are used interchangeable throughout the specification and refer to block polymers or copolymers of polyalkylene glycols, for example, a block polymer of ethylene oxide is referred to herein as polyethyleneoxy or polyoxyethylene. The polyalkyleneoxy units can have a molecular weight of from about 500 Daltons to about 50,000 Daltons. Another aspect comprises polyalkyleneoxy units having a molecular weight of from about 1000 Daltons to about 10,000 Daltons. A further aspect comprises polyalkyleneoxy units having a molecular weight of from about 5000 Daltons to about 20,000 Daltons. A still further aspect comprises polyalkyleneoxy units having a molecular weight of from about 10,000 Daltons to about 20,000 Daltons. A still further aspect comprises polyalkyleneoxy units having a molecular weight of from about 500 Daltons to about 3,000 Daltons. Specific examples of polyalkyleneoxy units include PEG 500, PEG 1000, PEG 1500, PEG 2000, PEG 3000, PEG 3200, PEG 3500, and PEG 5000.

One embodiment of a polyalkylene block polymer relates to a polyethyleneoxy having an average molecular weight of 8,000 daltons (PEG 8000). Typically the molecular weights of polyethylene glycols are determined by GPC methods. One aspect of this embodiment, includes polyethyleneoxy units that can have an average molecular weight of from about 100 daltons to about 1,000 daltons. In a yet other embodiment, polyethyleneoxy units can have an average molecular weight of from about 1,000 daltons to about 10,000 daltons. In still a further embodiment, polyethyleneoxy units can have an average molecular weight of from about 1,000 daltons to 8,000 daltons, while in a yet further embodiment, polyethyleneoxy units can have an average molecular weight of from about 1,000 daltons to 6000 daltons. Another embodiment of polyalkyleneoxy units relates polypropylene glycols, for example, a polypropylene glycol having an average molecular weight of 8,000 daltons (PPG 8000).

One aspect of this embodiment includes polypropyleneoxy units having an average molecular weight of from about 100 daltons to about 1,000 daltons. In a yet other embodiment, polypropyleneoxy units can have an average molecular weight of from about 1,000 daltons to about 10,000 daltons. In still a further embodiment, polypropyleneoxy units can have an average molecular weight of from about 1,000 daltons to about 8,000 daltons, while in a yet further embodiment, polypropyleneoxy units can have an average molecular weight of from about 1,000 daltons to about 6000 daltons. Specific examples of polyalkyleneoxy units include PPG 500, PPG 1000, PPG 1500, PPG 2000, PPG 3000, PPG 3200, PPG 3500, and PPG 5000.

A further example of suitable polyalkylene glycols units includes mixed alkyleneoxy copolymers, for example, poloxamers having an average molecular weight of from about 1000 daltons to about 100,000 daltons. These starting materials are also well known by the trade name PLURONICS™. These compounds are commonly named with the word Poloxamer followed by a number to indicate the specific copolymer, for example POLOXAMER 407 having two PEG blocks of about 101 units ($n^1$ and $n^3$ each equal to 101) and a polypropylene block of about 56 units. This starting material is available from BASF under the trade name LUTROL™ F-17.

Lactide/Glycolide/Poly(Vinyl Pyrrolidone) Copolymers

Another embodiment of copolymers according to the disclosed processes relates to copolymers comprising one or more poly(lactide-co-glycolide) or a poly(lactide) hydrophobic component and a polyvinyl pyrrolidone hydrophilic component.

AB Copolymers

One embodiment of the processes disclosed herein are microparticles comprising copolymers having two units, AB, wherein A represents a hydrophobic unit and B represents a hydrophilic unit wherein A and B can be any ratio, for example, 60%:40% or as a number ratio, for example, 85:15, whichever is convenient for the formulator.

This embodiment represents microparticles formed from copolymers having the formula:

AB wherein a hydrophobic component and a hydrophilic component are grafted or reacted together to form an essentially linear polymer that is non-water soluble.

The final molecular weights of the copolymers of this embodiment, that can be by GPC, are from about 1,000 daltons to about 2,000,000 daltons.

In one embodiment, the molecular weights are from about 2,000 daltons to about 200,000 daltons. In a further embodiment, the molecular weights are from about 4,000 daltons to about 150,000 daltons. In another embodiment, the molecular weights are from about 4,000 daltons to about 100,000 daltons. In a yet further embodiment, the molecular weights are from about 10,000 daltons to about 200,000 daltons.

One example is a copolymer having an average molecular weight of about 1000 daltons and a ratio of lactide to glycolide of 50:50. The hydrophilic component comprises of a PEG having an average molecular weight of about 250 daltons. In a further example, an AB copolymer has an average molecular weight of about 3400 daltons and a ratio of lactide to glycolide of 85:15 and the hydrophilic component comprises a PEG having an average molecular weight of about 600 daltons. In a yet further example, the AB copolymer has a molecular weight of about 6,550 daltons and the ratio of lactide to glycolide is 100:0.

ABA Copolymers

Copolymers according to the present disclosure can also comprise three units, ABA, wherein A represents a hydrophobic unit and B represents a hydrophilic unit, the ABA polymers represented by the formula:

$[A]_{j'}-[B]_k-[A]_{j''}$ wherein the indices j' and j" represent the relative amount of the hydrophobic component and k represents the relative amount of the hydrophilic component that comprises the copolymer. The indices j'+j"=j. The indices j and k can be reported as ratios or percentages, for example, 60%:40% or as a number ratio, for example, 85:15, whichever is convenient for the formulator.

Lactide/Glycolide/Hydroxy Acid/Polyalkyleneoxy Copolymers

Another embodiment of the present disclosure relates to copolymers wherein the hydrophobic component comprises lactide, glycolide, and a hydroxy acid other than lactide or glycolide. One aspect of these hydrophobic copolymers includes copolymers comprising ω-hydroxy acids, for example, 5-hydroxypentanoic acid. Hydroxy acids of this type are conveniently incorporated in the copolymer backbone by reaction of the corresponding lactone, for example, caprolactone or valerolactone. Copolymers of this type are known as poly(lactide-co-glycolide-co-caprolactone), poly (lactide-co-glycolide-co-valerolactone), poly(lactide-co-caprolactone), and poly(lactide-co-valerolactone).

Any suitable hydroxy acid, for example, α-hydroxybutyric acid, α-hydroxy-valeric acid, α-hydroxyacetic acid, α-hydroxycaproic acid, α-hydroxyheptanoic acid, α-hydroxydecanoic acid, α-hydroxymyristic acid, α-hydroxyoctanoic acid, and α-hydroxystearic acid can be used to from these copolymers.

A first aspect of this embodiment relates to poly(lactide-co-glycolide-co-caprolactone) copolymers any individual component of the copolymer may range from about 0% to 99%. In one aspect, the ratio of caprolactone to lactide-co-glycolide is from 50:50 to 10:90 while the ratio of lactide to glycolide is from 50:50 to 100:0. In one example, a hydrophobic copolymer comprises a 50:50 ratio of caprolactone to lactide-co-glycolide wherein the ratio of lactide-co-glycolide portion has a lactide to glycolide ratio of 85:15. In another example, the hydrophobic copolymer comprises a caprolactone to lactide-co-glycolide ratio of 1:5 wherein the lactide-co-glycolide portion has a ratio of lactide to glycolide of 3:1. In a further example, the hydrophobic copolymer comprises a caprolactone to lactide-co-glycolide ratio of 1:1 and the lactide-co-glycolide portion has a ratio of lactide to glycolide of 85:15.

The above hydrophobic copolymers can then be combined with a hydrophilic portion, for example, a polyalkylene glycol or polyvinyl pyrrolidone as described herein. The ratio of the hydrophobic portion to the hydrophilic portion can be from 1:99 to about 99:1. In one aspect, the ratio of the hydrophobic portion to the hydrophilic portion is from about 90:10 to about 50:50. In another aspect, the ratio of the hydrophobic portion to the hydrophilic portion is from about 80:20 to about 50:50. In a further aspect, the ratio of the hydrophobic portion to the hydrophilic portion is from about 70:30 to about 50:50. In a still further aspect, the ratio of the hydrophobic portion to the hydrophilic portion is from about 70:30 to about 60:40. Specific examples include, copolymers wherein the ratio of the hydrophobic portion to the hydrophilic portion is from about 80:20 to about 50:50 and the copolymers have an average molecular weight of from about 1000 to about 2000 Daltons.

Another aspect relates to copolymers wherein the ratio of the hydrophobic portion to the hydrophilic portion is from about 99:1 to about 90:10. As such, the hydrophobic portion can comprise from about 50:50 lactide to glycolide to about 100:0 lactide to glycolide (i.e., a lactide polymer). In one aspect, the ratio of the hydrophobic portion to the hydrophilic portion is from about 97:3, wherein the hydrophobic portion can comprise a lactide-co-glycolide for from about 75:25 to about 55:45, and wherein the hydrophilic portion can be a polyalkylene glycol or a polyvinyl pyrrolidone having an average molecular weight of from about 1000 to about 10,000 Daltons. In one example the hydrophilic portion is a polyalkylene glycol having a molecular weight of about 1500 Daltons. In another example, the hydrophilic portion is a polyvinyl pyrrolidone having a molecular weight of from about 2500 to about 5000 Daltons, while in a further example the hydrophilic portion is a polyvinyl pyrrolidone having a molecular weight of from about 800 to about 12,000 Daltons.

In another aspect, the ratio of the hydrophobic portion to the hydrophilic portion is from about 94:6, wherein the hydrophobic portion can comprise a lactide-co-glycolide for from about 75:25 to about 55:45, and wherein the hydrophilic portion can be a polyalkylene glycol or a polyvinyl pyrrolidone having an average molecular weight of from about 1000 to about 10,000 Daltons. In one example the hydrophilic portion is a polyalkylene glycol having a molecular weight of about 1500 Daltons. In one example the hydrophilic portion is a polyalkylene glycol having a molecular weight of about 1500 Daltons. In another example, the hydrophilic portion is a polyvinyl pyrrolidone having a molecular weight of from about 2500 to about 5000 Daltons, while in a further example the hydrophilic portion is a polyvinyl pyrrolidone having a molecular weight of from about 800 to about 12,000 Daltons.

In addition, the microparticles formed by the disclosed processes can comprise ABA copolymers of lactide, glycolide and ω-hydroxy acids.

In addition to the AB and ABA water insoluble copolymers disclosed above, the microparticles can be random copolymers, for example, copolymers having the formula ABBAAABBA and the like. In addition, a third component C, which can be block homopolymer or copolymer variations of the A units, can be copolymerized to form for example, ABC, ABBC, ABACAB, and the like copolymers.

Polymer Excipient

Another aspect of the processes disclosed herein relates to microparticles comprising polymer excipient wherein the polymer excipient can comprise any of the following.

Biocompatible and/or biodegradable polymers that can be added to the polymer admixture of step (a) include, but are not limited to, a poly(lactide); a poly(glycolide); a poly(lactide-co-glycolide); a poly(lactic acid); a poly(glycolic acid); a poly(lactic acid-co-glycolic acid); a poly(caprolactone); a poly(lactide-co-caprolactone) or polyalkylene glycol as described herein above. In addition, a poly(orthoester); a polyanhydride; a poly(phosphazene); a polyhydroxyalkanoate; a poly(hydroxybutyrate); a poly(hydroxybutyrate) synthetically derived; a poly(hydroxybutyrate) biologically derived; a polyester synthetically derived; a polyester biologically derived; a polycarbonate; a tyrosine polycarbonate; a polyamide (including synthetic and natural polyamides, polypeptides, poly(amino acids) and the like); a polyesteramide; a polyester; a poly(dioxanone); a poly(alkylene alkylate); polyvinyl pyrrolidone (PVP); a polyurethane; a polyetherester; a polyacetal; a polycyanoacrylate; a polyacetal, a polyketal; a polyphosphate; a (phosphorous-containing) polymer; a polyphosphoester; a polyhydroxyvalerate; a polyalkylene oxalate; a polyalkylene succinate; a poly(maleic acid); biopolymers or modified biopolymers including chitin, chitosan, modified chitosan, among other biocompatible polysaccharides; or biocompatible copolymers (including block copolymers or random copolymers) herein; or combinations or mixtures or admixtures of any polymers herein.

Another aspect of the polymer excipient of step (a) of the disclosed processes can include a biocompatible, non-biodegradable polymer such as further described herein, for example, a polyacrylate; a polymer of ethylene-vinyl acetate; an acyl substituted cellulose acetate; a non-degradable polyurethane; a polystyrene; a polyvinyl chloride; a polyvinyl fluoride; a poly(vinyl imidazole); a chlorosulphonate polyolefin; a polyethylene oxide; or a blend or copolymer thereof.

In one aspect of the disclosed processes, polymers, homopolymers, copolymers, and combinations thereof can be admixed (or blended) with a variety of other medically and pharmaceutically relevant polymers in order to prepare an even larger variety of low residual solvent level microparticles using the low water volumes and wherein the microparticles exhibit improved injectability properties. These other medically and pharmaceutically relevant polymers are obviously useful for preparation of microparticle compositions having a wide range of physical and chemical attributes.

This embodiment of the present disclosure encompasses admixtures of one or more hydrophilic components, for example, a component chosen from:
  i) polyalkylene glycol;
  ii) polyvinyl pyrrolidone;
  iii) poly(lactide)-co-(polyalkylene oxide);
  iv) poly(lactide-co-glycolide)-co-(polyalkylene oxide);
  v) poly(lactide-co-caprolactone)-b-(polyalkylene oxide);
  vi) poly(lactide-co-glycolide-co-caprolactone)-b-(polyalkylene oxide);
  vii) poly(lactide)-co-(polyvinyl pyrrolidone);
  viii) poly(lactide-co-glycolide)-co-(polyvinyl pyrrolidone);
  ix) poly(lactide-co-caprolactone)-b-(polyvinyl pyrrolidone); or
  x) poly(lactide-co-glycolide-co-caprolactone)-b-(polyvinyl pyrrolidone)

and one or more hydrophobic components, for example, a component chosen from:
  i) poly(lactide);
  ii) poly(lactide-co-glycolide);
  iii) poly(lactide-co-caprolactone);
  iv) poly(lactide-co-glycolide-co-caprolactone);
  v) poly(glycolide-co-caprolactone); and
  vi) poly(caprolactone).

This polymer excipient comprises from about 99% by weight of one or more hydrophobic polymers and about 1% by weight of one or more hydrophilic polymers to about 10% by weight of one or more hydrophobic polymers and about 90% by weight of one or more hydrophilic polymers. Preferably, this polymer excipient comprises from about 99% by weight of one or more hydrophobic polymers and about 1% by weight of one or more hydrophilic polymers to about 25% by weight of one or more hydrophobic polymers and about 75% by weight of one or more hydrophilic polymers.

Therefore, the microparticles of the disclosed processes are formed by a step (a) comprising:
  a) providing a polymer excipient of:
    i) from about 10% to about 99% by weight of one or more hydrophobic polymers; and
    ii) from about 1% to about 90% by weight of one or more hydrophilic polymers;
  in one or more organic solvents to form an organic phase.

Therefore, the microparticles of the disclosed processes are formed by a step (a) comprising:
  a) providing a polymer excipient of:
    i) from about 25% to about 99% by weight of one or more hydrophobic polymers; and
    ii) from about 1% to about 75% by weight of one or more hydrophilic polymers;
  in one or more organic solvents to form an organic phase.

Processes

The processes of the present disclosure comprise the following non-limiting steps and aspects thereof.

Step (a)

Step (a) of the processes disclosed herein comprises:
  (a) providing a composition comprising a polymer excipient in a weight amount of an organic solvent, $W_{DP\,solvent}$, to form the dispersed phase.

As described herein, polymer excipients comprising the composition of Step (a) of the disclosed process may be an AB block copolymer, an ABA block copolymer, a BAB block copolymer where the A block represents the hydrophilic component (block) and the B block represents the hydrophobic component (block) of the composition.

In addition, the non-water soluble block copolymer excipient comprising the composition of Step (a) of the disclosed process may be a regular or a random configuration of two or more A blocks and two or more B blocks where the A block represents the hydrophilic component (block) and the B block represents the hydrophobic component (block) of the composition.

Any of the polymer excipients herein above can be used in the processes of the present disclosure to form the low residual solvent level microparticles. The following embodiments are illustrative of the copolymers suitable for use in the present processes and are not meant to be limiting in scope.

In a first aspect of this embodiment the non-water soluble matrix-forming polymer used to prepare the microparticle formulation is an AB-block copolymer comprising a hydrophobic block of poly(lactide-co-glycolide) (PLG) and a hydrophilic block of polyalkylene glycol such as polyethylene glycol (PEG) as described herein. In another example, the non-water soluble copolymer comprises a hydrophobic block of poly(lactide) (PL) and a hydrophilic block of PEG. In another example, the copolymer contains a hydrophobic block of poly(lactide-co-glycolide) and a hydrophilic block of polyvinyl pyrrolidone (PVP). In another example, the copolymer contains a hydrophobic block of poly(lactide) and a hydrophilic block of polyvinyl pyrrolidone (PVP). A non-limiting example of the polymers of this aspect include hydrophilic blocks of polyethylene glycol or polyvinyl pyrrolidone having molecular weights of from about 100 daltons to about 1,000 daltons, or from about 1,000 daltons to about 8,000 daltons, or from about 5,000 daltons to about 100,000 daltons; further, the copolymers may have overall final molecular weights of from about 1,000 daltons to about 2,000,000 daltons or, alternatively, the copolymers may have overall inherent viscosities of from about 0.05 to about 2.0 dL/g.

In one example, the copolymer comprises a hydrophobic block of poly(lactide-co-glycolide) or a poly(lactide) and a hydrophilic block a polyalkyleneoxide such as polyethylene glycol (PEG). A non-limiting example of the copolymers of this aspect includes a non-water soluble poly(lactide-co-glycolide)-co-ethyleneoxy having a final molecular weight of from about 2,000 daltons to about 200,000 daltons, or from about 4,000 daltons to about 150,000 daltons, or from about 4,000 daltons to about 100,000 daltons, or yet further from about 10,000 daltons to about 200,000 daltons. Another example is poly(lactide)-co-polyethyleneoxide.

In another aspect of this embodiment the microparticle forming material is an ABA copolymer comprising poly(lactide-co-glycolide)-co-polyalkyleneoxide-co-poly(lactide-co-glycolide) or a poly(lactide)-co-polyalkyleneoxide-co-poly(lactide) hydrophobic component and a polyalkyleneoxide hydrophilic component as described herein. In one example, the copolymer comprises a poly(lactide-co-glycolide)-co-alkyleneoxy-co-poly(lactide-co-glycolide) or a poly(lactide)-co-alkyleneoxy-co-poly(lactide). A non-limiting example of a copolymer according to this aspect is poly(lactide-co-glycolide)-co-ethyleneoxy-co-poly(lactide-co-glycolide). The molecular weight range of these non-water soluble copolymers is the same as described herein.

In a further aspect of this embodiment the microparticle forming material is a random copolymer comprising poly(lactide-co-glycolide) or a poly(lactic acid) hydrophobic component randomly copolymerized with a polyalkyleneoxy hydrophilic component as described herein.

Another embodiment of the microparticle forming material is an AB copolymer comprising a hydrophobic component that is the reaction product of lactide, glycolide and a lactone or hydroxy acid forming a copolymer comprising poly(lactide-co-glycolide-co-ω-hydroxycarboxylate). This copolymer is further reacted with a polyalkylene glycol to form poly(lactide-co-glycolide-co-ω-hydroxycarboxylate)-co-polyalkyleneoxy. A non-limiting example of this copolymer is the AB copolymer wherein the hydrophobic component is formed by the reaction of (D,L)-3,6-dimethyl-1,4-dioxane-2,5-dione, 1,4-dioxane-2,5-dione, and caprolactone thereby forming poly(D,L-lactide-co-glycolide-co-ω-hexanoate). Another example of this embodiment includes hydrophobic components formed from a source of lactide and a ω-hydroxycarboxylic acid. The hydrophobic copolymer component of this embodiment can be reacted with one or more polyalkylene glycols to form the final non-water soluble copolymer.

The solvents useful in the disclosed processes include "halogenated solvents" and "non-halogenated solvents." Non-limiting examples of non-halogenated solvents include: dimethylsulfoxide (DMSO), triacetin, N-methylpyrrolidone (NMP), 2-pyrrolidone, dimethylformamide (DMF), miglyol, isopropyl myristate, triethyl citrate, propylene glycol, ethyl carbonate, ethyl acetate, ethyl formate, methyl acetate, glacial acetic acid, polyethylene glycol (200), polyethylene glycol (400), acetone, methyl ethyl ketone, methanol, ethanol, n-propanol, iso-propanol, benzyl alcohol, glycerol, diethyl ether, tetrahydrofuran, glyme, diglyme, n-pentane, iso-pentane, hexane, heptane, isooctane, benzene, toluene, xylene (all isomers), and the like. Non-limiting examples of halogenated solvents include carbon tetrachloride, chloroform, methylene chloride, chloroethane, 1,1-dichloroethane, 1,1,1-trichloroethane, and 1,2-dichloroethane.

As detailed herein below, both methylene chloride and ethyl acetate are convenient solvents for use in the disclosed processes.

In some examples, the salts of one or more ionic salts, metal halide salts (metal halides), salts of alkali metals and halogens, or salts of alkaline earth metals and halogens can be added to the solvent. The halogens can be F, Cl, Br, or I. In a specific example, the salt is sodium chloride or potassium chloride. The salt can be present at from 0.1 to 20 weight %, 2-20 weight %, or 2-15 weight %, in the continuous process medium. In another aspect the salt is sodium chloride, and is in an amount of from 0.6 to 20 weight % or from 0.1 molar (M) to 3.4 M. This can help reduce the amount of organic solvent needed and improve the properties of the final product. As such, the processes can, in certain examples, involve forming an emulsion or double emulsion comprising a dispersed phase comprising an agent, a polymer, and a first solvent for the polymer, in a continuous process medium, wherein the continuous process medium comprises at least one salt and at least one second solvent, wherein the second solvent reduces the solubility of the first solvent in the continuous process medium; and extracting the first solvent from the dispersed phase to form the microparticles.

The solvent or solvents used for the present processes can be present either as a primary solvent, a co-solvent, or as a processing aide. Solvents such as dichloromethane and ethyl acetate have wide utility as primary solvents in that the copolymers, as well as agents can be either solublized or dispersed therein. However, in one embodiment of the present processes, water can be necessary to dissolve one or more active agents.

The amount of solvent used in the disclosed processes for the purposes of calculating the amount of water necessary, is the weight of solvent used, typically in grams. The mass of solvent used in step (a) of the disclosed processes is $W_{DP\ solvent}$; however, if no other step in the process comprises an organic solvent, then $W_{DP\ solvent}$ will be the same as the total mass of organic solvent, $W_{organic\ solvent,\ total}$.

Another embodiment of step (a) relates to processes for preparing microparticles that comprise one or more active agents. In this embodiment step (a) comprises:
  a) providing a composition comprising a polymer excipient and one or more bioactive agents in a weight amount, $W_{DP\ solvent}$, of an organic solvent to form a dispersed phase;

In certain aspects of the disclosed processes for preparing microparticles such as emulsion-based techniques or spray-based techniques, the polymer solution can be dispersed as droplets (typically an aqueous dispersed phase) into a second liquid phase (the continuous phase). In such instances, where a liquid-liquid dispersion or emulsion is formed, the continuous phase can be comprised of a single solvent or of an admixture of two or more solvents (a solvent system). Alternatively, the composition of the continuous phase solvent system can be changed over time by addition of one or more solvents by addition either in a single operation or in multiple, successive addition operations over time after the formation of the initial dispersion or emulsion and after formation of the microparticles themselves.

A further embodiment of step (a) relates to processes for preparing microparticles wherein the active agent and the polymer excipient are dissolved or dispersed separately.

In a yet further embodiment of the disclosed processes, the active agent can be dissolved or otherwise solubilized in water prior to combination with the polymer, for example, the process comprising:
  (a)(i) providing a composition comprising a polymer excipient in a weight amount, $W_{DP\ solvent}$, of an organic solvent to form an organic phase polymer solution;
  (a)(ii) providing one or more actives dissolved or dispersed in a weight amount of water, $W_{w(DP)}$, to form an aqueous phase;
  (a)(iii) combining the organic phase formed in (a)(i) and the aqueous phase formed in (a)(ii) to form a water-in-oil emulsion wherein the discontinuous phase is the aqueous phase and the continuous phase is the organic phase wherein the resulting water-in-oil emulsion is the dispersed phase.

Processes of this type, generally known as water/oil/water processes or as double-emulsion processes for forming microparticles, will include the weight of water is $W_{w(DP)}$ from step (a)(ii) in calculating the total weight of water necessary for the process.

The disclosed processes can include a Step (a) that comprises polymer excipients comprising:
  i) a hydrophilic, water soluble biocompatible polymer comprising polyvinyl pyrrolidone having a molecular weight of from about 100 daltons to about 100,000 daltons; and
  ii) a non-water soluble, biocompatible and/or biodegradable polymer comprising lactide, glycolide, caprolactone, hydroxybutyrate, or hydroxyvalerates (or combinations thereof), the biocompatible polymer having a molecular weight from about 500 daltons to about 2,000,000 daltons;
wherein, the polymer excipient contains from about 1% by weight up to less than about 20% by weight of the water soluble biocompatible polymer.

The disclosed processes can comprise a Step (a) that comprises polymer excipients comprising:
  i) one or more hydrophobic components or blocks of a biocompatible polymer; and
  ii) one or more hydrophilic components or blocks of a hydrophilic (water soluble) biocompatible polymer;
wherein the non-water soluble block copolymer has a molecular weight of from about 1,000 to about 2,000,000 daltons.

The disclosed processes can further comprise a Step (a) that comprises polymer excipients comprising:
  i) one or more hydrophobic components (blocks) comprising biocompatible and biodegradable polymer chemistries including polyesters, polyanhydrides, polyorthoesters, polyphosphazenes, polyphosphates, polyphosphoesters, polyphosphonates, polydioxanones, polyhydroxyalkanoates, polycarbonates, polyalkylcarbonates, polyorthocarbonates, polyesteramides, polyamides, polyamines, polypeptides, polyurethanes, polyetheresters, or combinations thereof, the hydrophobic component having a molecular weight from about 500 daltons to about 2,000,000 daltons; and
  ii) one or more hydrophilic components (blocks) comprising hydrophilic (water-soluble) materials including polyalkylene glycols, polyalkylene oxides, polypeptides, polysaccharides, polyvinyl pyrrolidones, proteins, or modified polysaccharides or combinations thereof, the hydrophilic component having a molecular weight of from about 100 daltons to about 100,000 daltons;
wherein the copolymer is non-water soluble and has a molecular weight of from about 1,000 daltons to about 2,000,000 daltons.

The disclosed processes can yet further comprise a Step (a) that comprises polymer excipients comprising:
  i) a hydrophobic component (block) comprising lactide, glycolide, caprolactone, hydroxybutyrate, or hydroxyvalerates (or combinations thereof), the hydrophobic component having a molecular weight from about 500 daltons to about 2,000,000 daltons; and
  ii) a hydrophilic component (block) comprising a polyethylene glycol having a molecular weight of from about 100 daltons to about 100,000 daltons;
wherein the copolymer is non-water soluble and has a molecular weight of from about 1,000 daltons to about 2,000,000 daltons.

The disclosed processes can still further comprise a Step (a) that comprises polymer excipients comprising:
  i) a hydrophobic component (block) comprising lactide, glycolide, caprolactone, hydroxybutyrate, or hydroxyvalerates (or combinations thereof), the hydrophobic component having a molecular weight from about 500 daltons to about 2,000,000 daltons; and
  ii) a hydrophilic component (block) comprising a polyvinyl pyrrolidone having a molecular weight of from about 100 daltons to about 100,000 daltons;
wherein the copolymer is non-water soluble and has a molecular weight of from about 1,000 daltons to about 2,000,000 daltons.

The disclosed processes can still yet further comprise a Step (a) that comprises polymer excipients comprising:
  i) a non-water soluble block copolymer of Claim 12 having a molecular weight from about 500 to 2,000,000 daltons; and
  ii) a biocompatible and/or biodegradable polymer having a molecular weight from about 500 to 2,000,000 daltons;
wherein the polymer excipient contains from about 10% by weight up to less than about 100% by weight of the non-water soluble block copolymer.

The disclosed processes can even yet still further comprise a Step (a) that comprises polymer excipients comprising:
  i) a non-water soluble block copolymer of Claim 13 having a molecular weight from about 500 daltons to about 2,000,000 daltons; and
  ii) a biocompatible or biodegradable polymer comprising polyesters, polyanhydrides, polyorthoesters, polyphosphazenes, polyphosphates, polyphosphoesters, polyphosphonates, polydioxanones, polyhydroxyalkanoates, polycarbonates, polyalkylcarbonates, polyorthocarbonates, polyesteramides, polyamides, polyamines, polypeptides, polyurethanes, polyetheresters, or combinations thereof, the hydrophobic component having a molecular weight from about 500 daltons to about 2,000,000 daltons; and
wherein the polymer excipient contains from about 10% by weight up to less than about 100% by weight of the non-water soluble block copolymer.

The disclosed processes in another embodiment can comprise a Step (a) that comprises polymer excipients comprising:
  i) a non-water soluble block copolymer having a molecular weight from about 500 daltons to about 2,000,000 daltons; and,
  ii) a biocompatible or biodegradable polymer comprising lactide, glycolide, caprolactone, hydroxybutyrate, or hydroxyvalerates (or combinations thereof); having a molecular weight from about 500 daltons to about 2,000,000 daltons;
wherein the polymer excipient contains from about 10% by weight up to less than about 100% by weight of the non-water soluble block copolymer.

The disclosed processes in another further embodiment can comprise a Step (a) that comprises polymer excipients comprising:
  i) a hydrophilic, water soluble biocompatible polymer having a molecular weight from about 100 daltons to about 100,000 daltons; and,
  ii) non-water soluble, biocompatible and/or biodegradable polymers having a molecular weight from about 500 to 2,000,000 daltons;
wherein the polymer excipient contains from about 1% by weight up to less than about 20% by weight of the water soluble biocompatible polymer.

The disclosed processes in a yet further embodiment can comprise a Step (a) that comprises polymer excipients comprising:
  i) a hydrophilic, water soluble biocompatible polymer comprising polyalkylene glycol, polyalkylene oxide, polypyrrolidone, water soluble peptides, water soluble polypeptides, water soluble polysaccharides, water soluble modified polysaccharides, water soluble carbohydrates, water soluble polysaccharides, water soluble proteins, or combinations thereof, having a molecular weight from about 100 daltons to about 100,000 daltons; and,
  ii) a non-water soluble, biocompatible and/or biodegradable polymer comprising a polyester, polyanhydride, polyorthoester, polyphosphazene, polyphosphate, polyphosphoester, polyphosphonate, polydioxanone, polyhydroxyalkanoate, polycarbonate, polyalkylcarbonate, polyorthocarbonate, polyesteramide, polyamide, polyamine, polypeptide, polyurethane, polyetherester, or combinations thereof, the biocompatible polymer having a molecular weight from about 500 daltons to about 2,000,000 daltons;

wherein, the polymer excipient from about 1% by weight up to less than about 20% by weight of the water soluble biocompatible polymer.

The microparticles formed by the disclosed processes can further comprise an excipient comprising at least one member of an adhesive, a pesticide, a fragrance, an antifoulant, a dye, a salt, an oil, an ink, a cosmetic, a catalyst, a detergent, a curing agent, a flavor, a fuel, a herbicide, a metal, a paint, a photographic agent, a biocide, a pigment, a plasticizer, a propellant, a stabilizer, or a polymer additive.

The following are non-limiting examples of bioactive agents that can be incorporated into microparticle systems herein include, but are not limited to, peptides, proteins such as hormones, enzymes, antibodies, monoclonal antibodies, antibody fragments, monoclonal antibody fragments, and the like, nucleic acids such as aptamers, siRNA, DNA, RNA, antisense nucleic acids or the like, antisense nucleic acid analogs or the like, low-molecular weight compounds, or high-molecular-weight compounds. Bioactive agents contemplated for use in the microparticle compositions include anabolic agents, antacids, anti-asthmatic agents, analeptic agents, anti-cholesterolemic and anti-lipid and antihyperlipidemic agents, anticholinergic agents, anti-coagulants, anti-convulsants, antidiabetic agents; anti-diarrheals, anti-edema agents; anti-emetics, antihelminthic agents; anti-infective agents including antibacterial and antimicrobial agents, anti-inflammatory agents, anti-manic agents, antimetabolite agents, anti-migrane agents; anti-nauseants, anti-neoplastic agents, anti-obesity agents and anorexic agents; antipruritic agents; anti-pyretic and analgesic agents, anti-smoking (smoking cessation) agents and anti-alcohol agents; antispasmodic agents, anti-thrombotic agents, antitubercular agents; anti-tussive agents, anti-uricemic agents, anti-anginal agents, antihistamines, anxiolytic agents; appetite suppressants and anorexic agents; attention deficit disorder and attention deficit hyperactivity disorder drugs; biologicals, cerebral dilators, coronary dilators, bronchiodilators, cytotoxic agents, decongestants, diuretics, diagnostic agents, erythropoietic agents, expectorants, gastrointestinal sedatives, central nervous system ("CNS") agents, CNS stimulants, antipsychotics, atypical antipsychotics, hyperglycemic agents, hypnotics, hypoglycemic agents, immunomodulating agents, dopamine agonists, iron chelators, immunosuppressive agents, muscle relaxants, nicotine, parasympatholytics; sialagogues, ion-exchange resins, laxatives, mineral supplements, mucolytic agents, neuromuscular drugs, vasodialators, peripheral vasodilators, beta-agonists; tocolytic agents; psychotropics, psychostimulants, sedatives, stimulants, thyroid and anti-thyroid agents, tissue growth agents, uterine relaxants, vitamins, or antigenic materials.

Other bioactive agents include carbonic anhydrase inhibitors, adrenergic receptor agonists, adrenergic receptor antagonists, androgen inhibitors, polysaccharides, growth factors, VEGF, anti-VEGF, bone morphogenetic proteins (BMPs), hormones, hormonolytics, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate morphine, mineral supplements, cholestryramine, N-acetylprocainamide, acetaminophen, aspirin, ibuprofen, phenyl propanolamine hydrochloride, caffeine, guaifenesin, aluminum hydroxide, magnesium hydroxide, peptides, polypeptides, proteins, amino acids, hormones, interferons, cytokines, protein kinase inhibitors, and vaccines.

Other classes of bioactive agents include those cited in Goodman & Gilman's The Pharmacological Basis of Therapeutics (McGraw Hill) as well as bioactive agents included in the Merck Index and The Physicians Desk Reference (Thompson Healthcare).

Representative drugs or bioactive agents that can be used in the microparticle composition of the present disclosure include, but are not limited to, peptide drugs, protein drugs, desensitizing materials, antigens, anti-infective agents such as antibiotics, antimicrobial agents, antiviral, antibacterial, antiparasitic, antifungal substances and combination thereof, antiallergenics, steroids, androgenic steroids, decongestants, hypnotics, steroidal anti-inflammatory agents, anti-cholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, nonsteroidal anti-inflammatory agents, antiparkinsonian agents, anti-alzheimers agents, antihypertensive agents, beta-adrenergic blocking agents, alpha-adrenergic blocking agents, nutritional agents, and the benzophenanthridine alkaloids. The bioactive agent can further be a substance capable of acting as a stimulant, a sedative, a hypnotic, an analgesic, an anticonvulsant, and the like.

The microparticle composition can contain one bioactive agent or it can contain combinations of two or more bioactive agents including a large number of bioactive agents. The bioactive agent can be naturally-occurring, produced from fermentation or bacterial sources, or synthetic in origin or it can be prepared from a combination therein. The bioactive agent can be a compound that has been covalently or non-covalently modified using other materials. Examples include salt counter-ions, targeting agents, solubility modifiers, permeability modifiers, hydrophobic agents, hydrophilic agents hydrophobic polymers, hydrophilic polymers, block copolymers, and the like.

Other bioactive agents include but are not limited to analgesics such as acetaminophen, acetylsalicylic acid, and the like; anesthetics such as lidocaine, xylocalne, and the like; anorexics such as dexadrine, phendimetrazine tartrate, and the like; antiarthritics such as methylprednisolone, ibuprofen, and the like; antiasthmatics such as terbutaline sulfate, theophylline, ephedrine, and the like; antibiotics such as sulfisoxazole, penicillin G, ampicillin, cephalosporins, amikacin, gentamicin, tetracyclines, chloramphenicol, erythromycin, clindamycin, isoniazid, rifampin, and the like; antifungals such as amphotericin B, nystatin, ketoconazole, and the like; antivirals such as acyclovir, amantadine, and the like; anti-cancer agents such as cyclophosphamide, methotrexate, etretinate, and the like; anticoagulants such as heparin, warfarin, and the like; anticonvulsants such as phenyloin sodium, diazepam, and the like; antidepressants such as isocarboxazid, amoxapine, and the like; antihistamines such as diphenhydramine HCl, chlorpheniramine maleate, and the like; hormones such as insulin, progestins, steroids, corticosteroids, prostaglandins, estrogens, corticoids, glucocorticoids, androgens, and the like; glucagon-like peptides including glucagon, GLP-1, GLP-2, IP-1, IP-2, and the like; tranquilizers such as thorazine, diazepam, chlorpromazine HCl, reserpine, chlordiazepoxide HCl, and the like; toxins such as botulinum toxin, and the like; antispasmodics such as belladonna alkaloids, dicyclomine hydrochloride, and the like; vitamins and minerals such as essential amino acids, calcium, iron, potassium, zinc, vitamin $B_{12}$, and the like; cardiovascular agents such as prazosin HCl, nitroglycerin, propranolol HCl, hydralazine HCl, pancrelipase, succinic acid dehydrogenase, and the like as well as calcium channel blockers; peptides and proteins such as LHRH, somatostatin, calcitonin, growth hormone, growth releasing factor, angiotensin, FSH, EGF, vasopressin, ACTH, human serum albumin, gamma globulin, and the like; prostaglandins; nucleic acids; carbohydrates; fats; narcotics such as morphine, codeine, and the like; narcotic antagonists; narcotic partial-agonists; psychotherapeutics; anti-malarials, L-dopa, diuretics such as furosemide, spironolactone, and the like; antiulcer drugs such as rantidine HCl, cimetidine HCl, and the like.

Immunological agents that can be used herein include, cytokines, interleukins, interferon, colony stimulating factor, granulocyte-colony stimulating factors, granulocyte macrophage colony-stimulating factors, tumor necrosis factor, and the like; allergens such as cat dander, birch pollen, house dust mite, grass pollen, and the like; antigens of cush bacterial organisms as *Streptococcus pneumoniae, Haemophilus influenzae, Staphylococcus aureus, Streptococcus pyrogenes, Corynebacterium diphteriae, Listeria monocytogenes, Bacillus anthracis, Clostridium tetani, Clostridium botulinum, Clostridium perfringens. Neisseria meningitides, Neisseria gonorrhoeae, Streptococcus mutans. Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptspirosis interrogans, Borrelia burgddorferi, Campylobacter jejuni*, and the like; antigens of such viruses as smallpox, influenza A and B, respiratory synctial, parainfluenza, measles, HIV, SARS, varicella-zoster, herpes simplex 1 and 2, cytomeglavirus, Epstein-Barr, rotavirus, rhinovirus, adenovirus, papillomavirus, poliovirus, mumps, rabies, rubella, coxsackieviruses, equine encephalitis, Japanese encephalitis, yellow fever, Rift Valley fever, lymphocytic choriomeningitis, hepatitis B, and the like; antigens of such fungal, protozoan, and parasitic organisms such as *Cryptococcuc neoformans, Histoplasma capsulatum, Candida albicans, Candida tropicalis, Nocardiai asteroids, Rickettsia rickettsii, Rickettsia typhi, Mycoplasma pneumoniae, Chlamyda psittaci, Chlamydia trachomatis, Plasmodium falciparum, Trypanasoma brucei, Entamoeba histolytica, Toxoplasma gondii, Trichomonas vaginalis, Schistosoma mansoni*, and the like. These antigens can be in the form of whole killed organisms, peptides, proteins, glycoproteins, carbohydrates, or combinations thereof.

Step (b)

In one embodiment of step (b), the Dispersed Phase comprising polymer excipient that is combined with a continuous phase continuous processing medium comprising a weight amount of water, $W_{w-1}$, and an emulsion is then formed wherein the emulsion comprises the Dispersed Phase that is discontinuous in the continuous phase solution. For example, step (b) in this embodiment comprises:

(a) providing a composition comprising a polymer excipient of the present invention in a weight amount of an organic solvent, $W_{DP\ solvent}$ to form the dispersed phase;

(b) combining the dispersed phase formed in steps (a) or (a)(iii) with an aqueous continuous phase processing medium comprising a weight of water, $W_{CP\ solvent}$, to form an emulsion, the emulsion having a discontinuous organic phase and an continuous aqueous phase.

In another embodiment of step (b) the organic phase from step (a) comprises one or more active agents. Step (b) of the present processes involves forming an emulsion, wherein the discontinuous phase is the organic phase and the continuous phase is the aqueous phase.

In one embodiment of the disclosed processes the water phase of step (b) is saturated with the one or more solvents that are used in step (a) to dissolve or disperse the polymers, copolymers, active agents, and agents; and/or the water phase of step (b) contains one or more processing aids or additives or agents (such as emulsifiers or emulsification agents). This embodiment of the disclosed processes comprises:

(a) providing a composition comprising a polymer excipient and one or more bioactive agents or additives or agents in a weight amount, $W_{DP\ solvent}$, of an organic solvent to form a dispersed phase;

(b) combining the dispersed phase formed in (a) with a continuous phase processing medium comprising a weight amount of water, $W_{CP\ solvent}$, wherein the water is saturated with a weight amount, $W_{CP\ organic\ solvent}$, of the organic solvent used to prepare the dispersed phase in step (a) and/or wherein the continuous phase further comprises one or more processing aids or additives or agents (such as emulsifiers or emulsification agents), to form an emulsion, the emulsion having a discontinuous organic phase and a continuous aqueous phase;

However, in another embodiment of the disclosed processes, the dispersed phase formed in overall step (a) can also be an emulsion, for example, an emulsion wherein the discontinuous phase is an aqueous phase having $W_{DP\ water}$ amount of water and the continuous phase is an organic phase. This embodiment is typical for providing microparticles comprising active agents that are water soluble. The following illustrates an aspect of this water-soluble active agent process wherein the aqueous phase of step (b) is further saturated with the solvent from step (a)(i) and may optionally also contain processing aids or additives or agents (such as emulsifiers or emulsification agents):

(a)(i) providing a composition comprising a polymer excipient a weight amount, $W_{DP\ solvent}$, of an organic solvent to form an organic phase polymer solution;

(a)(ii) providing one or more actives dissolved or dispersed in a weight amount of water, $W_{DP\ water}$, to form an aqueous phase;

(a)(iii) combining the organic phase formed in (a)(i) and the aqueous phase formed in (a)(ii) to form a water-in-oil emulsion wherein the discontinuous phase is the aqueous phase and the continuous phase is the organic phase wherein the resulting water-in-oil emulsion is the dispersed phase;

(b) combining the dispersed phase (water-in-oil emulsion) formed in (a)(iii) with a continuous phase processing medium comprising a weight amount of water, $W_w$, wherein the water is saturated with a weight amount, $W_{org}$, of the organic solvent that comprises organic phase polymer solution formed in (a)(i), and wherein the continuous phase further comprises one or more processing or emulsification aids, to form an emulsion whereby the organic dispersed phase from step (a)(iii) is discontinuous in the organic-saturated continuous phase;

One example of the disclosed methods includes preparing the liquid-liquid emulsion comprising the dispersed phase which is discontinuous in the continuous phase processing medium by any variety of appropriate methods. One example includes emulsification by static methods such as static mixers, diffuser plates, screen or membrane or diffuser gaskets, turbulent flow; another example includes emulsification using homogenizers, mixers, blenders, agitation, ultrasound or ultrasonic energy and the like; another example includes the use of nozzles or jets to create the emulsion comprising a discontinuous phase within the continuous phase liquid either alone or through the combined use of other techniques; further examples may include processes that employ one or more such steps or methods during preparation of the emulsion.

Step (c)

Step (c) of the disclosed processes comprises adding the emulsion formed in step (b) to an extraction phase solution that serves to extract solvent comprising the discontinuous phase of the emulsion of step (b). In this step the microparticles or the microparticles comprising one or more active agents are first formed. The present process utilizes low water volumes to achieve microparticles having less than or equal to about 3 wt % residual solvent, preferably less than or equal to about 2 wt % residual solvent.

Step (c) comprises:
(c) combining the emulsion formed in step (b) with an additional weight amount of an extraction phase solvent, $W_{EP\ solvent}$;

generally and step (c) comprises:
(c) combining the emulsion formed in step (b) with an additional weight amount of an aqueous extraction phase solution comprising a weight of water, $W_{w(EP)}$;

more specifically when preparing microparticle using an oil-in-water emulsion process. For the various embodiments disclosed herein, the different extraction phase calculations will take into account the total amounts of solvent (such as the organic solvent) and extraction phase solvent (such as water) used in the process steps. For example, in the first embodiment wherein unloaded microparticles are formed (microparticles comprising no active agents) using an oil-in-water emulsion process, the following formula for calculating the total amount of extraction phase water ($W_{w,\ total}$) during step (b) can be used:

$$W_{W,total} \leq 10\left[\frac{W_{ORG,total}}{S}\right]$$

wherein $W_{w,\ total}$ is the combined total amount of extraction phase solvent (water) present in the system during solvent-extraction; and wherein $W_{org,\ total}$ is the combined total amount of a particular dispersed phase organic solvent present during solvent-extraction (for example, the cumulative weight of organic solvent present from all preceding processing steps (a), (b), and (c)); and S is the saturation solubility (in g/g) of the dispersed phase organic solvent in the final composition of the aqueous-based extraction phase solution used during the solvent-extraction.

Step (c) may also encompass the solvent-extraction step whereby the extraction of the dispersed phase solvent from the droplets of the discontinuous phase out into the EP solution added during step (c) results in precipitation of that matrix-forming polymer, causing the discontinuous droplets of the dispersed phase to harden into polymer-rich microparticles. Extracting sufficient solvent from the dispersed phase droplets so that the resulting polymer microparticles contain low levels of residual solvent often requires considerable excess volumes of dispersed phase in order to create sufficient sink conditions for that solvent-extraction step.

Step (d)

Step (d) encompasses isolation of the formed microparticles. As such, any process that the formulator can choose for isolating the microparticles is encompassed within the disclosed processes. Without being limiting, the formulator may choose to collect and isolate the microparticles by physically filtering the microparticles or the microparticles may be isolated by other suitable methods including, for example, spray drying, tangential filtration, centrifugation, evaporation, freeze drying, lyophilization, or by using combinations of two or more suitable methods.

Moreover, the disclosed processes can be adapted to any of the standard or customary procedures known to the artisan. As such, the microparticle compositions, therefore, can be prepared by any variety of ways that are practiced in the field to of preparing microparticles and particles, generally. One example of the disclosed methods includes microparticles prepared by spray-drying; another aspect includes microparticles prepared by fluid-bed techniques; another example includes techniques that utilize spraying of solutions through nozzles (or jets) into either air or into liquids in order to prepare microparticles. In a related aspect, cryogenic spray techniques would also be included (U.S. Pat. No. 5,989,463, for example, incorporated herein by reference). In another aspect of the disclosure, microparticle compositions can be prepared by ultrasonic spraying through nozzles (or jets) without or with the presence of applied electrical potential (so-called electrostatic spraying) as described in U.S. Pat. No. 6,669,961, included herein by reference. Another aspect of the present disclosure includes supercritical fluid techniques for the preparation of microparticle compositions. Another aspect of the disclosed methods includes preparation of microparticle compositions by any of the general techniques involving polymer precipitation or phase separation or coacervation and any combinations therein. Additional aspects of the present disclosure include microparticles that are prepared by combinations of techniques described herein.

The processes of the present disclosure are not limited to the steps, aspects and embodiments put forth herein above. Any processing steps utilizing the Extraction Ratio, for example, $$ER = \frac{W_{w,total}}{W_{org,total}/S}$$

wherein $W_{w,\ total}$, $W_{org,\ total}$, and S are defined herein, to calculate the lower amount of water necessary in forming microparticles having a residual solvent volume less than or equal to 3 wt % that are compatible with the use of the Extraction Ratio, is included.

One aspect of the present disclosure includes preparation of the microparticle composition by any emulsion-based techniques practiced in the field. Examples include emulsion-solvent extraction methods (for example, U.S. Pat. Nos. 5,407,609 and 5,650,173 and 6,537,586 and 6,540,393 and 5,654,008, each of which are included herein by reference), emulsion-solvent evaporation methods (for example, U.S. Pat. No. 4,530,840, included herein by reference) along with combinations of extraction and evaporation techniques (for example, U.S. Pat. No. 6,440,493, included herein by reference). Further aspects of the present disclosure include preparation or manufacturing processes that are conducted in either a batch mode, a continuous mode, or in a combination therein.

Other adjunct materials, excipients, agents, or ingredients, including processing aids, therapeutic, bioactive, diagnostic, and/or prophylactic agents, cells or whole tissues, can be either included into the resultant microparticles or can be added to one or more steps of the disclosed processes described herein. These adjunct materials, excipients, or ingredients can be used, for example, for controlled release of a drug, to render the devices radio-opaque, stimulate tissue in-growth, promote tissue regeneration, prevent infection, or modify the porosity of the device.

Bioactive agents can become complexed or otherwise associated with other excipients contained in the microparticle composition that alter or enhance the biological effect, biological activity, stability, or release of the bioactive agent. An example includes a protein (for example, human growth hormone) that is complexed with a cation (for example the divalent cation of zinc ($Zn^{+2}$) to improve the stability of the protein. In another aspect of the disclosed processes, these agents can simply be incorporated into the microparticle composition along with the bioactive agent without otherwise forming a complex or association between the bioactive agent and the other agent. Bioactive agents in the form of prodrugs (including polymeric pro-drugs) can be incorporated into the microparticle compositions of the disclosed processes. Further aspects of the disclosed processes include the incorporation of bioactive agents that have been otherwise chemically modified (for example, for purposes of achieving biological targeting or for other means of affecting the pharmacokinetics or biodistribution of the native bioactive agent or any combinations of the above).

In addition to bioactive agents, the microparticles can comprise other excipients such as an adhesive, a pesticide, a fragrance, an antifoulant, a dye, a salt, an oil, an ink, a cosmetic, a catalyst, a detergent, a curing agent, a flavor, a fuel, a herbicide, a metal, a paint, a photographic agent, a biocide, a pigment, a plasticizer, a propellant, a stabilizer, a polymer additive, any combination thereof.

Further aspects of the disclosed processes include the incorporation into the microparticles other excipients that can be beneficial for other clinical, diagnostic, surgical, or medical purposes. Examples include agents that provide adjuvant properties, radio-opacity, radionuclides, contrast agents, imaging agents, magnetic agents, and the like. Applications where these types of devices might be useful include any variety of medical imaging and diagnostics applications including, for example, MRI-based imaging such as metal oxide particles or iron oxide particles (including, for example super paramagnetic iron oxide, or SPIO, particles) and gadolinium-containing agents, among others. The microparticle compositions of the disclosed processes can also be prepared containing any of a variety of other dyes, contrast agents, fluorescent markers, imaging agents, magnetic agents, and radiologic agents used in any variety of medical diagnostic and imaging technologies.

The microparticles of the present disclosure can contain other excipients or agents including any number of other medically or pharmaceutically acceptable agents such as preservatives, lipids, fatty acids, waxes, surfactants, plasticizers, porosigens, antioxidants, bulking agents, buffering agents, chelating agents, cosolvents, water-soluble agents, insoluble agents, metal cations, anions, salts, osmotic agents, synthetic polymers, biological polymers, hydrophilic polymers, polysaccharides, sugars, hydrophobic polymers, hydrophilic block copolymers, hydrophobic block copolymers, block copolymers containing hydrophilic and hydrophobic blocks, and the like. Such excipients could be used singly or in combinations of two or more excipients when preparing microparticle compositions. These excipients can be useful in order to alter or affect drug release, water uptake, polymer degradation, stability of the bioactive agent, among other reasons. In certain aspects of the disclosed processes, these excipients can be used during preparation of the polymer admixture. In other aspects, these excipients can be added separately into the polymer solution itself. In still further aspects, these excipients can be incorporated into a first solution consisting of the bioactive agent dissolved or dispersed into a first solvent. In still further aspects, the excipients can be added into the polymer solution before, during, or after the bioactive agent is added into the polymer solution. In one aspect, such excipients can be used in the preparation of microparticle compositions that contain no bioactive agent.

In another aspect, such excipients can be added directly into the polymer solution, alternatively, the excipients can first be dissolved or dispersed in a solvent which is then added into the polymer solution. Examples of water soluble and hydrophilic excipients include poly(vinyl pyrrolidone) or PVP and copolymers containing one or more blocks of PVP along with blocks of other biocompatible polymers (for example, poly(lactide) or poly(lactide-co-glycolide) or polycaprolactone); poly(ethylene glycol) or PEG and copolymers containing blocks of PEG along with blocks of other biocompatible polymers (for example, poly(lactide) or poly(lactide-co-glycolide) or polycaprolactone); poly(ethylene oxide) or PEO, and copolymers containing one or more blocks of PEO along with blocks of other biocompatible polymers (for example, poly(lactide) or poly(lactide-co-glycolide) or polycaprolactone) as well as block copolymers containing PEO and poly(propylene oxide) or PPO such as the triblock copolymers of PEO-PPO-PEO (such as POLOXAMERS™, PLURONICS™); and, modified copolymers of PPO and PEO containing ethylene diamine (POLOXAMINES™ and TETRONICS™). In other aspects, the microparticle composition can be prepared containing one or more bioactive agents or one or more excipients or combinations thereof.

Depending on the application for which the formulator is preparing microparticles by way of the disclosed process, the microparticles can contain bioactive agents or excipients or combinations thereof at concentration levels having a wide range. Again, depending upon the application, microparticles can contain agents at levels from about 0.0001 to about 99.9 weight percent (wt %) of the microparticles. For example, in one aspect of the disclosed processes, microparticles intended for the delivery of vaccine antigens are generally only required to deliver very small or trace quantities of the bioactive agent (in this case, the vaccine antigen). Loading levels of the antigen in such cases can be far less than about 1 wt % in the final composition in some instances or can, in many instances, be below about 0.1 wt %, and in some cases less than about 0.01 wt %. In other aspects, the loading of the excipients can be larger. For example, one aspect of the disclosed processes the incorporation of bioactive peptides into the microparticles. In these cases, the bioactive peptide can be present in the microparticle composition at levels of about 1-10 wt percent. In other examples, a bioactive peptide with all of its associated soluble salts can easily be present in the microparticle composition at loading levels of about 40 wt % or higher. In still further aspects of the disclosed processes, an excipient can be incorporated into the microparticle composition at higher loading levels; for example, in excess of about 50 wt % or about 60 wt %. In still further aspects of the disclosed processes, it is possible that a microparticle composition can be prepared that contains very little polymer. An example of such a situation can include an SPIO particle that is coated or encapsulated with small layer of a polymer composition of the disclosed processes using an emulsion process or a spray-nozzle process included herein. Another example would include a core particle that is simply coated with a layer or layers of polymers including the polymer composition of the disclosed processes by an appropriate coating technique (including, for example, an emulsion process or spray-coating or fluid-bed). In examples such as these, the microparticle composition can be largely comprised of either the SPIO particles or the core particle that has been encapsulated or coated with only a very small amount of polymer. In these and related applications, therefore, it is possible that the microparticle composition can contain greater than about 80% or about 90% or about 99% of the excipient and, correspondingly, will contain very little of the polymeric composition.

In summary, therefore, it should be clear that various aspects of the disclosed processes include microparticle compositions can be comprised of agents at composition levels that range from about 0 (zero) wt % (for example, the first embodiment of step (a) wherein only a polymer admixture or copolymer is dissolved or dispersed in one or more organic solvents) to very low loading levels (such as less than about 1 wt %) to intermediate loading levels (such as about 1-10 wt % and about 1-50 wt %) to very high loading levels (such as greater than about 90 wt % or greater than about 95% or greater than about 99%) depending on many factors including, but not limited to, the particular application, the choice and attributes of the excipient itself, and the size and structure of the microparticle composition.

The following examples are set forth below to illustrate the compositions, methods, and results according to the disclosed subject matter. These examples are not intended to be inclusive of all aspects of the subject matter disclosed herein, but rather to illustrate representative compositions, methods, and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, mixing speeds, pressures and other reaction ranges and conditions that can be used to optimize the product purity and yield obtained from the described process. Only reasonable and routine experimentation will be required to optimize such process conditions.

EXAMPLE 1

Emulsion-based Encapsulation Process Using Different Solvents

Microparticle formulations were prepared using an emulsion, solvent-extraction process as described below. A dispersed phase solution was prepared by dissolving a total of 2 grams of a biodegradable polymer in 8 grams of an organic solvent (either ethyl acetate or methylene chloride). The resulting polymer solution contained 20 wt. % polymer. Separately, a continuous phase solution was prepared by adding an amount of organic solvent (either 11.5 grams of ethyl acetate or 2.4 grams of methylene chloride) to 150 grams of an aqueous solution containing 2% poly(vinyl alcohol) (PVA) (available from Amresco; Solon, Ohio).

The dispersed phase solution was then emulsified into the continuous phase solution at room temperature using a SILVERSON™ L4R-TA probe mixer (fine screen) for 45 seconds. In this particular processing step, samples prepared from ethyl acetate dispersed phase solutions were processed using continuous phase solutions that contained ethyl acetate; similarly, samples prepared from methylene chloride dispersed phase solutions were processed using continuous phase solutions that contained methylene chloride. After this time, the resulting emulsion was then immediately added to a beaker containing a specific quantity of the extraction phase (extraction phase) solution (deionized water) that was being stirred with a overhead laboratory mixer at a stir speed of 600 rpm.

When preparing samples using ethyl acetate at Extraction Ratio levels of 3, 8, and 15, the amount of extraction phase solution used in this step was 700, 2000, 3750 grams, respectively. When preparing samples using methylene chloride at Extraction Ratio levels of 3, 8, and 15, the amount of extraction phase solution used in this step was 1750, 5000, and 9750 grams, respectively.

After about 90 minutes of extraction time, the resulting suspension was passed through two 8-inch diameter test sieves where the first sieve had a mesh size of 125 microns and the second sieve had a mesh size of 25 microns (RETSCH™ or FISHER™ test sieves). The microparticle product material that passed through the 125 micron sieve but that was collected on top of the 25 micron test sieve was then rinsed with 2 L of deionized water. This product was then dried by lyophilization by re-suspending the product from the 25 micron test sieve in about 1100 mL of deionized water and then freezing this suspension and lyophilizing for 48 hours to remove the bulk water. After drying, the microparticle product was transferred to a scintillation vial which was then securely closed and was stored desiccated and frozen until further analysis.

Therefore, a sample prepared using ethyl acetate wherein the target Extraction Ratio is 3, would involve the use of a total of about 19.5 grams of ethyl acetate (about 8 grams from the preparation of the dispersed phase solution and about 11.5 grams used to prepare the continuous phase solution) and about 847 grams of water (about 147 grams from the PVA solution and 700 grams of the extraction phase solution). Under these conditions the extraction ratio for this process is about 3.2 (assuming an aqueous solubility of ethyl acetate of about 0.075 g/g). Table 1 provides examples of various extraction ratios and the amounts of each phase used in the processes wherein ethyl acetate and methylene chloride are used as dispersed phase and continuous phase solvents. The calculations in Table 1 used aqueous solubilities of 0.075 g/g and 0.015 g/g, respectively, for ethyl acetate (EtOAc) and methylene chloride.

Table 1 depicts the amount of solvent and water used to form microparticles according to Example 1. The table provides the theoretical, as well as the actual extraction ratios obtained under the conditions of Example 1 using the volumes of solvent and water disclosed below. In the following tables and the examples provided therein, poly(DL-lactide-co-glycolide) polymers, for example, 65:35 PLG, are used as the control samples.

TABLE 1

|  | Ethyl Acetate | | | Methylene Chloride | | |
| --- | --- | --- | --- | --- | --- | --- |
| Solvent dispersed phase (g) | 8 | 8 | 8 | 8 | 8 | 8 |
| Solvent continuous phase (g) | 11.5 | 11.5 | 11.5 | 2.4 | 2.4 | 2.4 |
| Water continuous phase (g) | 147 | 147 | 147 | 147 | 147 | 147 |
| Water extraction phase (g) | 700 | 2000 | 3750 | 1750 | 5000 | 9750 |

TABLE 1-continued

|  | Ethyl Acetate | | | Methylene Chloride | | |
| --- | --- | --- | --- | --- | --- | --- |
| Total solvent (g) | 19.5 | 19.5 | 19.5 | 10.4 | 10.4 | 10.4 |
| Total water (g) | 847 | 2147 | 3897 | 1897 | 5147 | 9897 |
| Theoretical Extraction Ratio | 3 | 8 | 15 | 3 | 8 | 15 |
| Calculated Extraction Ratio | 3.2 | 8.2 | 15.0 | 2.7 | 7.4 | 14.3 |

Table 2 compares microparticles formed using a poly(DL-lactide-co-glycolide) copolymer and microparticles formed using a poly(DL-lactide-co-glycolide)-co-(PEG) according to the disclosed process using the conditions described in Example 1. In Table 2, 65:35 PLG refers to a 65:35 poly(DL-lactide-co-glycolide) copolymer (0.44 dL/g reported inherent viscosity or IV) (Lakeshore polymer 65:35 DL-PLG, 4.5A and 65:35 PLG-PEG(1500) refers to a 65:35 poly(DL-lactide-co-glycolide)-co-(polyethylene glycol MW=1500) copolymer according to the present disclosure. The inherent viscosity of the 65:35 PLG-PEG(1500) block copolymer is 0.44 dL/g as reported by the vendor (Brookwood Pharmaceuticals; Birmingham, Ala.). Microparticles of each polymer were prepared using both ethyl acetate and methylene chloride.

Microparticle formulations were analyzed for particle size and particle size distribution using a Coulter LS-13,320 laser diffraction particle size analyzer with micro-volume module. Briefly, approximately 100 mg of a test sample was accurately weighed into a test tube. Then 4 mL aliquot of a 0.1 wt % Tween-80 solution was added to the test tube which was then sonicated for approximately 15 seconds (Cole-Parmer sonicator batch Model 8893). After sonication, the sample was then mixed by vortex mixer (Vortex Genie; Fisher Scientific) at a setting of "high" for approximately 15 seconds. Portions of this sample were then added to the stirred sample cell of the particle size analyzer to get suitable signal. Size analysis was carried out using a Fraunhofer optical model and results were calculated using volume-average statistics. The reported results include the mean particle size (mean) and the particle size at the $90^{th}$-percentile of the particle size distribution, otherwise noted as either D(90) or $D_{90}$, which serves as an indicator of the size range on the upper end of the particle size distribution. Particle size results are included in Table 2 and demonstrate that mean particle sizes of the samples ranged from about 45 to 85 microns.

TABLE 2

| | Target | | | Particle size, μm | |
| --- | --- | --- | --- | --- | --- |
| Sample number | Organic solvent[1] | extraction ratio | Biodegradable polymer | Mean (μm) | D(90) (μm) |
| 1 | EtOAc | 3 | 65:35 PLG | 54.6 | 80.0 |
| 2 | EtOAc | 8 | 65:35 PLG | 47.6 | 67.0 |
| 3 | EtOAc | 15 | 65:35 PLG | 50.0 | 68.2 |
| 4 | EtOAc | 3 | 65:35 PLG-PEG(1500) | 82.6 | 183.3 |
| 5 | EtOAc | 8 | 65:35 PLG-PEG(1500) | 65.1 | 141.6 |
| 6 | EtOAc | 15 | 65:35 PLG-PEG(1500) | 68.3 | 138.3 |
| 7 | $CH_2Cl_2$ | 3 | 65:35 PLG | 85.8 | 115.2 |
| 8 | $CH_2Cl_2$ | 8 | 65:35 PLG | 82.4 | 113.8 |
| 9 | $CH_2Cl_2$ | 15 | 65:35 PLG | 83.3 | 115.7 |
| 10 | $CH_2Cl_2$ | 3 | 65:35 PLG-PEG(1500) | 75.2 | 103.9 |
| 11 | $CH_2Cl_2$ | 8 | 65:35 PLG-PEG(1500) | 78.9 | 104.3 |
| 12 | $CH_2Cl_2$ | 15 | 65:35 PLG-PEG(1500) | 70.5 | 98.9 |

Analysis of Microparticles

EXAMPLE 2

Total Volatiles Method

Thermogravimetric analysis (TGA) was utilized to determine the total volatiles content of a microparticle sample. Results of TGA testing, therefore, include both the amount of residual solvent in the sample and the amount of residual moisture remaining in the sample.

TGA analysis was conducted using a Thermogravimetric analyzer, Model 2950 from TA Instruments (Newcastle, Del.). The change in weight of a 10-30 mg sample was monitored over time by the TGA analyzer while heating the sample to 200° C. at a rate of 10° C./minute. The sample is then maintained at this temperature for 10 minutes. The total weight change at this time is determined and is then converted to a total percent volatiles based on the total weight change observed and the starting sample weight. Reported results are the mean of duplicate samples.

Water Content Method

Total residual moisture content of a microparticle sample was determined by coulometric Karl-Fischer titration (KF) using a Mitsubishi CA-100 titrator equipped with a VA-100 vaporizer oven. Aquamicron brand CXU (cathode) and AX (anode) solutions were used to perform the titrations ((Mitsubishi Corp.; Tokyo, Japan). Briefly, a 20-30 mg sample was placed added to the oven which was then heated to 150° C. A flow of nitrogen gas at about 70 mL/minute was utilized to transport any evolved residual moisture from the sample into the titration cell for quantitation. Titration is carried out until the residual moisture rate falls below a cut-off level of 0.1 micrograms/second.

The percent residual moisture in the sample is calculated based on the mass of moisture in the sample (as measured by titration) and the total mass of sample that was analyzed. Reported results are the mean of duplicate samples.

Calculated Residual Solvent Content

The TGA and KF results have been used to calculate residual solvent of the sample. The estimated residual solvent level is simply the difference between the total percent volatiles in the sample (by TGA) and the percent residual moisture content (by KF). In some cases, small negative numbers are obtained by this approach and this generally reflects instances where the sample contains relatively small levels of residual solvent. Estimating the amount of residual solvent in this manner (namely, by difference between the results of two analytical methods), it is possible to obtain a negative result. This is observed in one example in Table 3. This represents the inherent variability of the two methods employed and, generally, this may be observed when handling samples having relatively small residual solvent levels (as compared to the total amount of residual moisture in the sample). In these instances, the estimated residual solvent value will be rounded to zero for comparison purposes.

Figure 2:
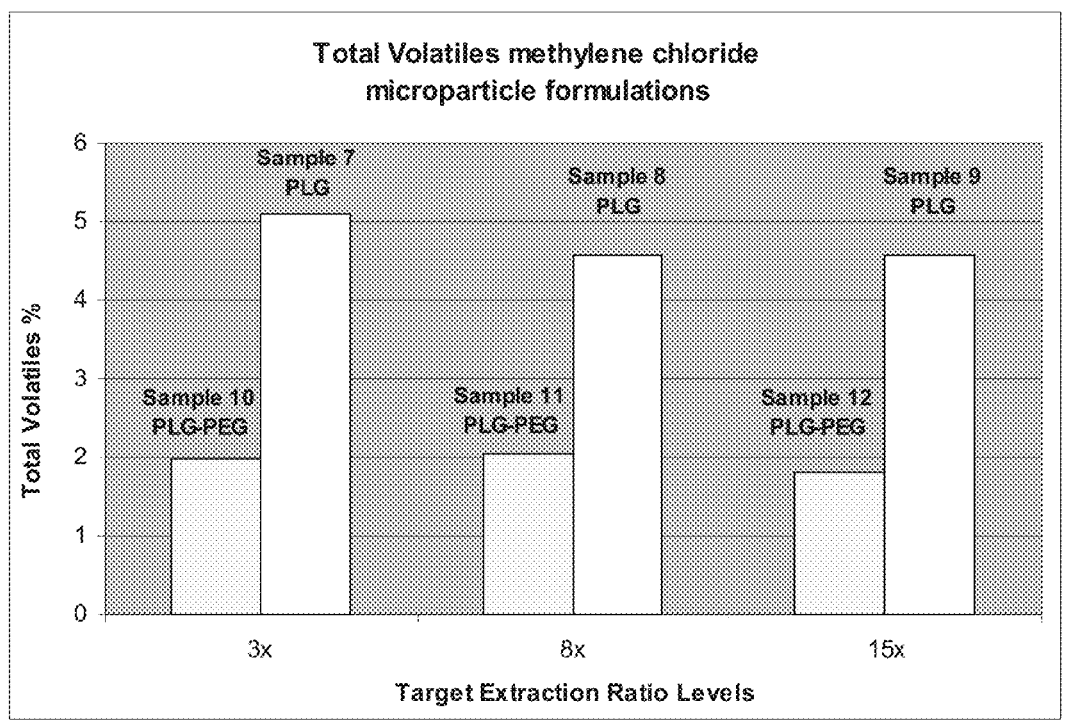
FIG. 2 depicts the results provided in Table 3 wherein methylene chloride is used as the solvent for the dispersed phase.

All samples have been analyzed for percent volatiles by TGA as an initial indicator of the residual solvent levels. In some instances, KF titration was performed to assess residual moisture levels and to allow the residual solvent content to be estimated by difference between these two results. Results of testing conducted on the samples from Example 1 are presented in Table 3. The results from Table 3 volatiles testing are depicted in FIGS. 1 and 2.

TABLE 3

| Sample number | Organic solvent[1] | Target ER | Biodegradable polymer | % volatiles (TGA) | % moisture (KF) | % residual solvent |
|---|---|---|---|---|---|---|
| 1 | EtOAc | 3 | 65:35 PLG | 4.1 | | |
| 2 | EtOAc | 8 | 65:35 PLG | 3.9 | 0.4 | 3.5 |
| 3 | EtOAc | 15 | 65:35 PLG | 3.7 | | |
| 4 | EtOAc | 3 | 65:35 PLG-PEG(1500) | 0.74 | | |
| 5 | EtOAc | 8 | 65:35 PLG-PEG(1500) | 0.65 | 1.3 | (0) |
| 6 | EtOAc | 15 | 65:35 PLG-PEG(1500) | 0.63 | | |
| 7 | $CH_2Cl_2$ | 3 | 65:35 PLG | 5.1 | | |
| 8 | $CH_2Cl_2$ | 8 | 65:35 PLG | 4.6 | 0.3 | 4.3 |
| 9 | $CH_2Cl_2$ | 15 | 65:35 PLG | 4.6 | | |
| 10 | $CH_2Cl_2$ | 3 | 65:35 PLG-PEG(1500) | 2.0 | 0.4 | 1.6 |
| 11 | $CH_2Cl_2$ | 8 | 65:35 PLG-PEG(1500) | 2.0 | | |
| 12 | $CH_2Cl_2$ | 15 | 65:35 PLG-PEG(1500) | 1.8 | | |

EXAMPLE 3

Table 4 shows a comparison of residual solvent levels obtained by different drying methods. The microparticles disclosed in Table 4 were prepared using an emulsion, solvent-extraction process similar to that of Example 1. The targeted Extraction Ratio for these solvents was equal to 3 using ethyl acetate as the processing solvent. A dispersed phase solution was prepared by dissolving 2 grams of the polymer in 8 grams of ethyl acetate (20% total polymer concentration, by weight). Separately, a continuous phase solution was prepared by adding about 11.5 grams of ethyl acetate to 150 grams of an aqueous solution containing 2% poly (vinyl alcohol) (PVA) (Amresco; Solon, Ohio). The dispersed phase solution was then emulsified into the continuous phase solution at room temperature using a SILVERSON™ L4R-TA probe mixer (fine screen) for 45 seconds. After this time, the resulting emulsion was immediately added to a beaker containing about 700 grams of an extraction phase (deionized water) that was stirred with a laboratory overhead mixer at 600 rpm. After about 90 minutes of extraction time, the suspension was passed across two 8-inch diameter test sieves of mesh size 125 μm and 25 μm. The microparticles collected between the 125 μm and 25 μm sieves were rinsed with 2 L of deionized water then dried either by air-drying or by lyophilization. Air-drying was conducted by placing the 25 micron sieve in a laminar flow hood for 48 hours to allow the product to dry by evaporation at room temperature. The microparticles dried by lyophilization were resuspended in 100 mL of deionized water and lyophilized for 48 hours to remove the bulk water. After drying, the microparticle product was transferred to a scintillation vial. Vialed samples were securely closed and stored desiccated and frozen until further analysis.

The polymers used in this example included a 65:35 PLG having a reported inherent viscosity of 0.48 dL/g (a 65:35 DL-PLG, 4.5A from Brookwood Pharmaceuticals (Birmingham, Ala.) and a 65:35 PLG-PEG(1500) block copolymer from Brookwood Pharmaceuticals (Birmingham, Ala.) having a reported inherent viscosity of 0.39 dL/g.

The samples and processing conditions examined in this Example are given in Table 4 along with results of the characterization of these formulations. The drying methodology is found to have only a minor effect on residual solvent level. In contrast, the use of water-insoluble, hydrophilic-block copolymers containing a hydrophilic block (the PLG-PEG block copolymer) was observed to have a dramatic effect on the residual solvent level of the final product regardless of the drying methodology employed.

TABLE 4

Testing of samples from Example 3 (comparison of sample drying method on the estimated residual solvent level)

| Sample number | Biodegradable polymer | Drying method | % volatiles (TGA) | % moisture (KF) | % residual solvent |
|---|---|---|---|---|---|
| 13 | 65:35 PLG | Lyophilize | 5.98 | 0.38 | 5.60 |
| 14 | 65:35 PLG-PEG(1500) | Lyophilize | 2.12 | 0.81 | 1.31 |
| 15 | 65:35 PLG | Air-dry | 4.72 | 0.45 | 4.27 |
| 16 | 65:35 PLG-PEG(1500) | Air-dry | 0.53 | 0.75 | (0) |

EXAMPLE 4

Poly(Lactide-Co-Glycolide)-Co(Polyethylene Glycol) Copolymer-Biocompatible and/or Biodegradable Polymer Blends The following relates to microparticles formed from an admixture comprising a poly(lactide-co-glycolide)-co(polyethylene glycol) copolymer and one or more biocompatible and/or biodegradable polymers. Table 5 provides examples of polymer admixtures that can form the disclosed microparticles.

TABLE 5

| Sample number | Biodegradable polymer | % volatiles (TGA) | % moisture (KF) | Estimated % residual solvent |
|---|---|---|---|---|
| 13 | 100% 65:35 PLG control | 5.98 | 0.38 | 5.60 |
| 14 | 100% 65:35 PLG-PEG(1500) | 2.12 | 0.81 | 1.31 |
| 17 | 90% 65:35 PLG 10% 65:35 PLG-PEG(1500) | 5.23 | 0.46 | 4.77 |
| 18 | 75% 65:35 PLG 25% 65:35 PLG-PEG(1500) | 4.43 | 0.40 | 4.03 |
| 19 | 25%65:35 PLG 75% 65:35 PLG-PEG(1500) | 1.37 | 0.65 | 0.72 |

The samples listed in Table 5 were prepared according to the procedure described in Example 3 using ethyl acetate as the solvent. The target Extraction Ratio for the preparation of these examples was 3. The polymers used to form admixtures 17-19 are 65:35 PLG having a reported inherent viscosity of 0.48 dL/g (a Lakeshore Biomaterials 65:35 DL-PLG, 4.5A and a 65:35 PLG-PEG(1500) block copolymer having a reported inherent viscosity of 0.39 dL/g. The disclosed microparticle formulations were prepared by dissolving the polymer or the specified blend of polymers in the organic processing solvent when forming the dispersed phase solution.

EXAMPLE 5

Table 6 below depicts the effect the extraction time on the microparticle residual solvent level. Samples 13 and 20-24 were prepared using the procedure of Example 4 using the indicated extraction times.

TABLE 6

| Sample number | Biodegradable polymer | Extraction time, minutes | % volatiles (TGA) | % moisture (KF) | % residual solvent |
|---|---|---|---|---|---|
| 13 | 100% 65:35 PLG control | 90 | 5.96 | 0.45 | 5.51 |
| 20 | 75% 65:35 PLG 25% 65:35 PLG-PEG(1500) | 90 | 4.24 | 0.62 | 3.62 |
| 21 | 100% 65:35 PLG | 180 | 4.65 | 0.47 | 4.18 |
| 22 | 75% 65:35 PLG 25% 65:35 PLG-PEG(1500) | 180 | 3.37 | 0.72 | 2.65 |
| 23 | 100% 65:35 PLG | 270 | 4.19 | 0.42 | 3.77 |
| 24 | 75% 65:35 PLG 25% 65:35 PLG-PEG(1500) | 270 | 2.85 | 0.68 | 2.17 |

EXAMPLE 6

Table 7 discloses examples of microparticles formed using admixtures of water-soluble, hydrophilic polymers and biocompatible and/or biodegradable polymers. The microparticles were prepared according to the prepared using the procedure disclosed in Example 3 using ethyl acetate as the dispersed phase solvent and a target Extraction Ratio of 3. Each sample was dried using lyophilization. The microparticles were formed using 65:35 Poly(lactide-co-glycolide) having an inherent viscosity of 0.48 dL/g available as 4.5A from Brookwood Pharmaceuticals (Birmingham, Ala.) and polyethylene glycol having an average molecular weight of about 1500 g/mol (PE 1500), available from Spectrum Chemicals, Gardena, Calif.

TABLE 7

| Sample number | Biodegradable polymer | % volatiles (TGA) | % moisture (KF) | % residual solvent |
|---|---|---|---|---|
| 13 | 100% 65:35 PLG | 5.98 | 0.38 | 5.60 |
| 25 | 97% 65:35 PLG 3% PEG(1500) | 3.39 | 0.51 | 2.88 |
| 26 | 94% 65:35 PLG 6 PEG(1500) | 0.35 | 0.13 | 0.22 |
| 27 | 88% 65:35 PLG 12% PEG(1500) | 0.38 | 0.47 | (0) |

EXAMPLE 7

A further example of polymers that can be blended with poly(lactide-co-glycolide) copolymers includes polyvinyl pyrrolidone, PVP. Table 8 provides examples of polyvinyl pyrrolidone admixtures with poly(DL-lactide-co-glycolide) copolymers. The polyvinyl pyrrolidones used in these examples are PVP K-12 available from Acros Chemicals (New Jersey) having a molecular weight of about 3,500 Daltons and PVP K-15 having a molecular weight of about 10,000 Daltons available from Sigma-Aldrich; St. Louis, Mo. The PVP's were blended into the microparticle formulations at levels of 3 wt % and 6 wt % as provided in Table 8. Samples were prepared by the method of Examples 2 and 3 using methylene chloride as the processing solvent and at a target Extraction Ratio level of 3. All samples were dried by lyophilization.

TABLE 8

| Sample number | Biodegradable polymer | % volatiles (TGA) | % moisture (KF) | % residual solvent |
|---|---|---|---|---|
| 28 | 100% 65:35 PLG | 5.85 | 0.42 | 5.43 |
| 29 | 97% 65:35 PLG 3% PVP K-12 | 4.3 | 0.52 | 3.78 |
| 30 | 94% 65:35 PLG 6% PVP K-12 | 3.95 | 0.49 | 3.46 |
| 31 | 97% 65:35 PLG 3% PVP K-15 | 4.2 | 0.37 | 3.83 |
| 32 | 94 5:35 PLG 6% PVP K-15 | 3.97 | 0.42 | 3.55 |

EXAMPLE 8

As described herein, the disclosed microparticles can be prepared from admixtures of poly(DL-lactide-co-glycolide) copolymers and poly(DL-lactide-co-glycolide)-co-(polyethylene glycol). The admixtures provided in Example 9 comprise the following components:

i) 65:35 PLG, 4.5A a Lakeshore Biomaterials polymer available from Brookwood Pharmaceuticals, Birmingham, Ala., having a reported inherent viscosity of 0.48 dL/g;

ii) poly(DL-lactide) available from Birmingham Polymers (Birmingham, Ala.) having an IV of approximately 0.37 dL/g;

iii) 50:50 poly(DL-lactide-co-glycolide)-co-(polyethylene glycol MW=1500) having an IV of approximately 0.37 dL/g;

iv) 50:50 poly(DL-lactide-co-glycolide)-co-(polyethylene glycol MW=6000) having an IV of approximately 0.35 dL/g; and v) 50:50 poly(DL-lactide)-co-(polyethylene glycol MW=1500) having an IV of approximately 0.62 dL/g.

The microparticles provided in Tables 9-11 were prepared by dissolving the polymer or the specified blend of polymers in the organic processing solvent when making the dispersed phase solution.

TABLE 9

| 50:50 PLG-PEG(1500) copolymers | | | | |
|---|---|---|---|---|
| Sample number | Polymer Blends | % volatiles (TGA) | % moisture (KF) | % residual solvent |
| 13 | 100% 65:35 PLG | 5.98 | 0.38 | 5.60 |
| 33 | 90% 65:35 PLG 10% 50:50 PLG-PEG(1500) | 5.23 | 0.45 | 4.78 |
| 34 | 75% 65:35 PLG 25% 50:50 PLG-PEG(1500) | 4.02 | 0.42 | 3.6 |
| 35 | 50% 65:35 PLG 50% 50:50 PLG-PEG(1500) | 3.63 | 0.43 | 3.2 |
| 36 | 100% 50:50 PLG-PEG(1500) | 1.37 | 0.56 | 0.81 |

TABLE 10

75:25 PLG-PEG(6000) copolymers

| Sample number | Polymer Blends | % volatiles (TGA) | % moisture (KF) | % residual solvent |
|---|---|---|---|---|
| 13 | 100% 65:35 PLG | 5.98 | 0.38 | 5.60 |
| 37 | 95% 65:35 PLG 5% 75:25 PLG-PEG(6000) | 5.0 | 0.45 | 4.55 |
| 38 | 90% 65:35 PLG 10% 75:25 PLG-PEG(6000) | 1.76 | 0.48 | 1.28 |

TABLE 11

PL-PEG(1500) copolymers

| Sample number | Polymer Blends | % volatiles (TGA) | % moisture (KF) | % residual solvent |
|---|---|---|---|---|
| 39 | 100% PL | 3.38 | 0.36 | 3.02 |
| 40 | 75% PL 25% PL-PEG(1500) | 2.33 | 0.32 | 2.01 |
| 41 | 100% PL-PEG (1500) | 1.99 | 0.5 | 1.49 |

EXAMPLE 9

A further example of polymers that can be blended with poly(lactide-co-glycolide) copolymers includes polycaprolactone, PCL. Table 12 provides examples of polycaprolactone admixtures with poly(DL-lactide-co-glycolide) copolymers. The polycaprolactone used in these examples are available from Sigma-Aldrich (St. Louis, Mo.) having an average molecular weight of about 65,000 Daltons. The samples were prepared by the method of Examples 2 and 3 using methylene chloride as the processing solvent and at a target Extraction Ratio level of 3. All samples were dried by lyophilization.

TABLE 12

| Sample number | Polymer Blends | % volatiles (TGA) | % moisture (KF) | % residual solvent |
|---|---|---|---|---|
| 42 | 100% 65:35 PLG | 5.85 | 0.42 | 5.43 |
| 43 | 90% PCL 10% 75:25 PLG-PEG(6000) | 0.37 | 0.45 | (0) |

EXAMPLE 10

As described herein, the disclosed microcapsules can be prepared using either a batch process or a continuous process. The Table 13 provides examples of microparticles formed by continuous and batch processes prepared using ethyl acetate and a target Extraction Ratio level of about 3. All samples were dried using lyophilization. For comparison purposes, microcapsules were prepared as described in Example 3 using the 65:35 PLG and the 65:35 PLG-PEG(1500) polymers.

The same polymers were also used to prepare 30-gram batches using a continuous-emulsion process as follows. A dispersed phase solution comprising 20 wt % polymer was prepared by dissolving 30 grams of the polymer in 120 g of ethyl acetate. Separately, a continuous phase solution was prepared by combining 77 g of ethyl acetate and 1000 g of an aqueous solution comprising 2 wt % poly(vinyl alcohol) PVA (Amresco, Solon, Ohio). A Silverson L4R-T mixer was configured with a laboratory in-line mixer head with a general-purpose disintegrating head (stator screen). The dispersed phase solution and the continuous phase solution were separately delivered into the inlet assembly of the in-line mixer head at flow rates of 20 g/min and 125 g/min, respectively. The effluent emulsion from the mixer was then immediately diluted with additional extraction-phase (extraction phase) solution (deionized water) which was delivered into the emulsion effluent stream in a continuous manner at a flow rate of about 900 g/min. The resulting effluent stream was continuously delivered into an 18-gallon tank until all the dispersed phase solution had been delivered into the mixer. The 18-gallon tank was stirred throughout at a stir speed of about 600-900 rpm. The in-line mixer was operated at a sufficient stir speed (approximately 1000-1200 rpm) to obtain product with a mean size of about 40-90 microns. After the dispersed phase solution was depleted, the flow of the continuous phase and extraction phase solutions was discontinued. The suspension in the tank was stirred for an additional 90 minutes in order to facilitate extraction of the solvent from the microparticle product. At this time, the microparticle suspension in the 18-gallon tank was pumped across a 125 micron test sieve and a 25 micron test sieve (Retsch brand or Fisher brand). The microparticle product material that passed through the 125 micron sieve but that was collected on top of the 25 micron test sieve was then rinsed with 4-L of clean, deionized water. After this washing step, the product was dried by resuspending the product into 200 mL of deionized water. This suspension was then frozen and the bulk water was removed by lyophilization for 48 hours. After drying the microparticle product was transferred to a scintillation vial. Vialed samples were securely closed and stored desiccated and frozen until further analysis.

In the above example, a total of 150 g of dispersed phase solution was prepared comprising 120 g of ethyl acetate. The run-time to process this amount of dispersed phase solution (at a flow rate of 20 g/min) was about 7.5 minutes. Approximately 940 grams of continuous phase solution was used during this process. This quantity of continuous phase solution contained about 77 g of ethyl acetate and about 863 g of a 2 wt % PVA solution (containing the equivalent of about 846 grams of water). At a flow rate of about 900 g/min, the extraction phase solution used in this process consisted of about 6750 grams of water. Using these numbers, then, the combined amount of organic solvent in this system was about 197 grams (120 grams from the dispersed phase solution and another 77 grams from the continuous phase solution) and the total amount of water in the process was about 7596 grams (846 grams from the continuous phase solution and another 6750 grams from the extraction phase solution). Using a value of 0.075 g/g as the aqueous solubility of ethyl acetate in water, the actual Extraction Ratio used to prepare the 30-g batches in this continuous-emulsion example was approximately 2.9.

TABLE 13

| Sample number | Polymer | Process | % volatiles (TGA) | % moisture (KF) | % residual solvent |
|---|---|---|---|---|---|
| 13 | 65:35 PLG | Batch | 5.98 | 0.38 | 5.60 |
| 14 | 65:35 PLG-PEG(1500) | Batch | 2.12 | 0.81 | 1.31 |
| 44 | 65:35 PLG | Continuous | 5.3 | 0.2 | 5.1 |
| 45 | 65:35 PLG-PEG(1500) | Continuous | 2.3 | 0.8 | 1.5 |

EXAMPLE 11

Microcapsules were prepared according to the disclosed process comprising nalmefene base. The process used to prepare these samples is similar to that from the previous example except that 3 grams of nalmefene base (approximate particle size of about 12 microns) was added to the polymer solution which was then stirred for 30 minutes in order to prepare the dispersed phase solution that was then used in the encapsulation process. In these examples, the 3 grams of nalmefene base along with the 30 grams of polymer resulted in a theoretical loading level of 9.1 wt % drug. Batches were made using ethyl acetate as a solvent using a target extraction ratio level of 3 and the product was dried by lyophilization. Results from Table 14 demonstrate that drug-loaded microparticle product prepared by the method of the present invention have low residual solvent levels.

TABLE 14

| Sample number | Polymer | % volatiles (TGA) | % moisture (KF) | % residual solvent |
| --- | --- | --- | --- | --- |
| 13 | 65:35 PLG (control) | 5.98 | 0.38 | 5.60 |
| 46 | 65:35 PLG (with Nalmefene) | 5.2 | 0.3 | 5.1 |
| 47 | 65:35 PLG-PEG(1500) (with Nalmefene) | 2.1 | 0.6 | 1.5 |

EXAMPLE 12

The level of residual solvent in the above examples was determined by taking the difference between results of TGA and KF measurements. Samples prepared were measured for their actual residual solvent levels by headspace gas chromatography (GC) using a Perkin-Elmer Clarus 500 GC/FID equipped with a Turbo Matrix head-space HS-40 unit. Briefly, a 60 mg sample was dissolved in 5 mL dimethylformamide (DMF). Headspace analysis was performed at a 5 mL/min GC flow rate (helium) through a Restek RTX-1301 (30 m×0.53 mm, 3-micron) column using ethyl acetate standards (in DMF) ranging in concentration of 0.1 to 1.8 mg/mL. Table 15 provides a comparison of solvent levels obtained by difference with solvent levels obtained by GC analysis.

TABLE 15

| Sample number | Polymer or polymer blends | % volatiles (TGA) | % moisture (KF) | % residual solvent | % residual solvent (GC) |
| --- | --- | --- | --- | --- | --- |
| 38 | 90% 65:35 PLG 10% 75:25 PLG-PEG(6000) | 1.76 | 0.48 | 1.28 | 1.03 |
| 44 | 65:35 DL-PLG | 3.76 | 0.27 | 3.49 | 3.41 |
| 45 | 65:35 PLG-PEG(1500) | 1.7 | 0.65 | 1.05 | 1.17 |

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A process for preparing low residual solvent level microparticles, comprising:
   (a) providing a dispersed phase comprising a polymer excipient in a weight amount of a dispersed phase solvent, $W_{DP\ solvent}$, wherein the polymer excipient comprises:
      i) a non-water soluble block copolymer comprising a polyethylene glycol (PEG) hydrophilic block or blocks and a hydrophobic block or blocks; or
      ii) an admixture of non-water soluble block copolymers comprising a PEG hydrophilic block or blocks and a hydrophobic block or blocks; or
      iii) an admixture of a PEG hydrophilic, water soluble biocompatible polymer; and a non-water soluble, biocompatible and/or biodegradable polymer;
   (b) combining the dispersed phase with a continuous phase processing medium to form an emulsion wherein the dispersed phase is a discontinuous phase in the continuous phase;
   (c) combining the emulsion formed in (b) with a weight amount of an extraction phase solvent, $W_{EP\ solvent}$, thereby forming microparticles; wherein the $W_{EP}$ solvent comprises water or a mixture of water and a fully water-miscible solvent, and
   (d) isolating the microparticles;
   wherein the amount of residual dispersed phase solvent present in the isolated microparticles is less than or equal to about 3 wt %, and is less than the amount of residual dispersed phase solvent present in microparticles produced by said process in the absence of PEG;
   the total amount of extraction phase solvent is $W_{EP\ solvent,\ total}$ defined by the formula:

$$W_{EP\,solvent,total} \le ER\left[\frac{W_{DP\,solvent,total}}{S}\right]$$

wherein $W_{DP\ solvent,\ total}$, is the combined total amount of a particular dispersed phase solvent used in the process;
   S is the solubility of the dispersed phase solvent in water; and
   ER is the Extraction Ratio, wherein ER is less than or equal to about 10.

2. The process according to claim 1, wherein the Extraction Ratio is less than or equal to about 9.

3. The process according to claim 1, wherein the Extraction Ratio is less than or equal to about 8.

4. The process according to claim 1, wherein the Extraction Ratio is less than or equal to about 7.

5. The process according to claim 1, wherein the Extraction Ratio is less than or equal to about 6.

6. The process according to claim 1, wherein the dispersed phase of Step (a) comprises a non-water soluble block copolymer comprising:
   i) one or more hydrophobic components or blocks of a biocompatible polymer; and
   ii) one or more PEG hydrophilic components or blocks of a hydrophilic (water soluble) biocompatible polymer;
   wherein the non-water soluble block copolymer has a molecular weight of from about 1,000 to about 2,000,000 daltons.

7. The process according to claim 1, wherein the dispersed phase of Step (a) comprises a block copolymer comprising:
   i) one or more hydrophobic components (blocks) comprising biocompatible and biodegradable polymer chemistries comprising polyesters, polyanhydrides, polyorthoesters, polyphosphazenes, polyphosphates, polyphosphoesters, polyphosphonates, polydioxanones, polyhydroxyalkanoates, polycarbonates, polyalkylcarbonates, polyorthocarbonates, polyesteramides, polyamides, polyamines, polypeptides, polyurethanes, polyetheresters, or combinations thereof; the hydrophobic component having a molecular weight from about 500 daltons to about 2,000,000 daltons; and ii) one or more hydrophilic components (blocks) comprising PEG; the hydrophilic component having a molecular weight of from about 100 daltons to about 100,000 daltons;

wherein the copolymer is non-water soluble and has a molecular weight of from about 1,000 daltons to about 2,000,000 daltons.

8. The process according to claim 1, wherein the dispersed phase of Step (a) comprises a block copolymer comprising:
   i) a hydrophobic component comprising lactide, glycolide, caprolactone, hydroxybutyrate, or hydroxyvalerate or a combination thereof, the hydrophobic component having a molecular weight from about 500 daltons to about 2,000,000 daltons; and
   ii) a hydrophilic component comprising a polyethylene glycol having a molecular weight of from about 100 daltons to about 100,000 daltons;

wherein the copolymer is non-water soluble and has a molecular weight of from about 1,000 daltons to about 2,000,000 daltons.

9. The process according to claim 1, wherein the polymer excipient of Step (a) comprises:
   iii) a non-water soluble block copolymer having a molecular weight from about 500 to 2,000,000 daltons; and
   iv) a biocompatible and/or biodegradable polymer having a molecular weight from about 500 to 2,000,000 daltons;

wherein the polymer excipient contains from about 10% by weight up to less than about 100% by weight of the non-water soluble block copolymer.

10. The process according to claim 1, wherein the polymer excipient of Step (a) comprises:
   i) a non-water soluble block copolymer having a molecular weight from about 500 daltons to about 2,000,000 daltons; and
   ii) a biocompatible or biodegradable polymer having a molecular weight from about 500 daltons to about 2,000,000 daltons, comprising a polyester, polyanhydride, polyorthoester, polyphosphazene, polyphosphate, polyphosphoester, polyphosphonate, polydioxanone, polyhydroxyalkanoate, polycarbonate, polyalkylcarbonate, polyorthocarbonate, polyesteramide, polyamide, polyamine, polypeptide, polyurethane, polyetherester, or a combination thereof; and wherein the polymer excipient contains from about 10% by weight up to less than about 100% by weight of the non-water soluble block copolymer.

11. The process according to claim 1, wherein the polymer excipient of Step (a) comprises:
   i) a non-water soluble block copolymer having a molecular weight from about 500 daltons to about 2,000,000 daltons; and,
   ii) a biocompatible or biodegradable polymer comprising lactide, glycolide, caprolactone, hydroxybutyrate, or hydroxyvalerate or a combination thereof; having a molecular weight from about 500 daltons to about 2,000,000 daltons;

wherein the polymer excipient contains from about 10% by weight up to less than about 100% by weight of the non-water soluble block copolymer.

12. The process according to claim 1, wherein the polymer excipient of Step (a) comprises comprising:
   iii) a PEG hydrophilic, water soluble biocompatible polymer having a Molecular weight from about 100 daltons to about 100,000 daltons; and,
   iv) a non-water soluble, biocompatible and/or biodegradable polymer having a molecular weight from about 500 to 2,000,000 daltons;

wherein the polymer excipient contains from about 1% by weight up to less than about 20% by weight of the water soluble biocompatible polymer.

13. The process according to claim 1, wherein the polymer excipient of Step (a) comprises comprising:
   iii) a hydrophilic, water soluble biocompatible polymer comprising a PEG having a molecular weight from about 100 daltons to about 100,000 daltons; and,
   iv) a non-water soluble, biocompatible and/or biodegradable polymer comprising a polyester, polyanhydride, polyorthoester, polyphosphazene, polyphosphate, polyphosphoester, polyphosphonate, polydioxanone, polyhydroxyalkanoate, polycarbonate, polyalkylcarbonate, polyorthocarbonate, polyesteramide, polyamide, polyamine, polypeptide, polyurethane, polyetherester, or a combination thereof; the biocompatible polymer having a molecular weight from about 500 daltons to about 2,000,000 daltons;

wherein, the polymer excipient from about 1% by weight up to less than about 20% by weight of the water soluble biocompatible polymer.

14. The process according to claim 1, wherein the polymer excipient of Step (a) comprises:
   i) a hydrophilic, water soluble biocompatible polymer comprising a polyethylene glycol having a molecular weight from about 100 daltons to about 100,000 daltons; and,
   ii) a non-water soluble, biocompatible and/or biodegradable polymer comprising lactide, glycolide, caprolactone, hydroxybutyrate, hydroxyvalerate, or a combination thereof, the biocompatible polymer having a molecular weight from about 500 daltons to about 2,000,000 daltons;

wherein, the polymer excipient contains from about 1% by weight up to less than about 20% by weight of the water soluble biocompatible polymer.

15. The process according to claim 1, wherein the polymer excipient of Step (a) comprises:
   i) a hydrophilic, water soluble biocompatible polymer comprising polyethylene glycol having a molecular weight of from about 100 daltons to about 100,000 daltons; and
   ii) a non-water soluble, biocompatible and/or biodegradable polymer comprising lactide, glycolide, caprolactone, hydroxybutyrate, hydroxyvalerate, or a combination thereof, the biocompatible polymer having a molecular weight from about 500 daltons to about 2,000,000 daltons;

wherein, the polymer excipient contains from about 1% by weight up to less than about 20% by weight of the water soluble biocompatible polymer.

16. The process according to claim 1, wherein the dispersed phase of Step (a) comprises a non-water soluble block copolymer that is an AB block copolymer, an ABA block copolymer, or a BAB block copolymer, wherein the A block represents the hydrophilic component and the B block represents the hydrophobic component of the composition.

17. The process according to claim 1, wherein the dispersed phase of Step (a) comprises a non-water soluble block copolymer that is a regular or a random configuration of two or more A blocks and two or more B blocks, wherein the A block represents the hydrophilic component and the B block represents the hydrophobic component of the composition.

18. The process according to claim 1, wherein the dispersed phase solvent of Step (a) is a non-halogenated solvent.

19. The process according to claim 1, wherein the dispersed phase solvent of Step (a) is a non-halogenated solvent comprising acetone, methyl ethyl ketone, methanol, ethanol, n-propanol, iso-propanol, benzyl alcohol, glycerol, diethyl ether, tetrahydrofuran, glyme, diglyme, methyl acetate, ethyl acetate, n-pentane, iso-pentane, hexane, heptane, isooctane, benzene, toluene, or xylene.

20. The process according to claim 1, wherein the dispersed phase solvent of Step (a) is ethyl acetate.

21. The process according to claim 1, wherein the dispersed phase solvent of Step (a) is a halogenated solvent comprising carbon tetrachloride, chloroform, methylene chloride, chloroethane, 1,1-dichloroethane, 1,1,1-trichloroethane, or 1,2-dichloroethane.

22. The process according to claim 1, wherein the dispersed phase solvent of Step (a) is methylene chloride.

23. The process according to claim 1, wherein the microparticles are nanoparticles, microspheres, nanospheres, microcapsules, or nanocapsules having a size from about 10 nanometers to 2 millimeters.

24. The process according to claim 1, wherein the residual solvent level is less than or equal to 1.75%.

25. The process according to claim 1, wherein the residual solvent level is less than or equal to 1.5%.

26. The process according to claim 1, wherein the residual solvent level is less than or equal to 1.25%.

27. The process according to claim 1, wherein the residual solvent level is less than or equal to 1%.

28. The process according to claim 1, wherein further the residual moisture level is less than of equal to 1.75%.

29. The process according to claim 1, wherein the residual moisture level is less than or equal to 1.5%.

30. The process according to claim 1, wherein the residual moisture level is less than or equal to 1.25%.

31. The process according to claim 1, wherein the residual moisture level is less than or equal to 1%.

32. The process according to claim 1, wherein the continuous processing medium comprises one or more processing aids.

33. The process according to claim 32, wherein the processing aid comprises poly(vinyl alcohol).

34. The process according to claim 1, wherein the dispersed phase of Step (a) further comprises one or more agents.

35. The process according to claim 1, wherein the dispersed phase of Step (a) further comprises a bioactive agent, the bioactive agent comprising at least one member of peptides, proteins, antibodies, antibody fragments, monoclonal antibodies, monoclonal antibody fragments, nucleic acids, antisense nucleic acids, anabolic agents, antacids, anti-asthmatic agents, analeptic agents, anti-cholesterolemic, anti-lipid and antihyperlipidemic agents, anticholinergic agents, anti-coagulants, anti-convulsants, antidiabetic agents; anti-diarrheals, anti-edema agents; anti-emetics, antihelminthic agents; anti-infective agents, antibacterial agents, antimicrobial agents, anti-inflammatory agents, anti-manic agents, antimetabolite agents, anti-migrane agents; anti-nauseants, anti-neoplastic agents, anti-obesity agents, anorexic agents; antipruritic agents; anti-pyretic agents, analgesic agents, anti-smoking agents, anti-alcohol agents; anti-spasmodic agents, anti-thrombotic agents, antitubercular agents; anti-tussive agents, anti-uricemic agents, anti-anginal agents, antihistamines, anxiolytic agents; appetite suppressants, attention deficit disorder agents, attention deficit hyperactivity disorder drugs, biologicals, cerebral dilators, coronary dilators, bronchiodilators, cytotoxic agents, decongestants, diuretics, diagnostic agents, erythropoietic agents, expectorants, gastrointestinal sedatives, central nervous system agents, central nervous system stimulants, antipsychotics, atypical antipsychotics, dopamine agonists, iron chelators, hyperglycemic agents, hypnotics, hypoglycemic agents, immunomodulating agents, immunosuppressive agents, muscle relaxants, nicotine, parasympatholytics, sialagogues, ion-exchange resins, laxatives, mineral supplements, mucolytic agents, neuromuscular drugs, vasodialators, peripheral vasodilators, beta-agonists; tocolytic agents; psychotropics, psychostimulants, sedatives, stimulants, thyroid and anti-thyroid agents, tissue growth agents, uterine relaxants, vitamins, or antigenic agents.

36. The process according to claim 1, wherein the dispersed phase of Step (a) further comprises a bioactive agent, the bioactive agent comprising at least one member of hormones, enzymes, antibodies, aptamers, siRNA's, DNA's, RNA's, or antisense nucleic acids.

37. The process according to claim 1, wherein the dispersed phase of Step (a) further comprises an inhibitor, the inhibitor comprising at least one member of polysaccharide, growth factor, VEGF, anti-VEGF, bone morphogenetic proteins (BMPs), hormone, hormonolytic, anti-angiogenesis factor, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate morphine, mineral supplements, cholestryramine, N-acetylprocainamide, acetaminophen, aspirin, ibuprofen, phenyl propanolamine hydrochloride, caffeine, guaifenesin, aluminum hydroxide, magnesium hydroxide, peptide, polypeptide, protein, amino acid, hormone, interferon, cytokines, carbonic anhydrase inhibitors, adrenergic receptor agonists, adrenergic receptor antagonists, protein kinase inhibitors, or vaccines.

38. The process according to claim 1, wherein the dispersed phase of Step (a) further comprises an antibiotic, the antibiotic comprising at least one member of an antimicrobial agent, antiviral, antibacterial, antiparasitic, antifungal substance and combination thereof, antiallergenic, steroid, androgenic steroid, decongestant, hypnotic, steroidal anti-inflammatory agent, anti-cholinergic, sympathomimetic, sedative, miotic, psychic energizer, tranquilizer, vaccine, estrogen, progestational agent, humoral agent, prostaglandin, analgesic, antispasmodic, antimalarial, antihistamine, cardioactive agent, nonsteroidal anti-inflammatory agent, anti-parkinsonian agent, anti-alzheimers agent, antihypertensive agent, beta-adrenergic blocking agent, alpha-adrenergic blocking agent, nutritional agent, or the benzophenanthridine alkaloid.

39. The process according to claim 1, wherein the dispersed phase of Step (a) further comprises at least one member of a compound capable of acting as a stimulant, a compound capable of acting as a sedative, a compound capable of acting as a hypnotic, a compound capable of acting as an analgesic, or a compound capable of acting as an anticonvulsant.

40. The process according to claim 1, wherein the dispersed phase of Step (a) further comprises an agent, the agent comprising at least one member of anorexic, antiarthritic, antiasthmatic, antibiotic, antifungal, antiviral, anticancer agent, anticoagulant, anticonvulsant, antidepressant, antihistamine, hormone, tranquilizer, antispasmodic, vitamins and mineral, cardiovascular agent, calcium channel blocker, peptides and protein, prostaglandin, nucleic acid, carbohydrate, fat, narcotic, narcotic antagonist, narcotic partial-agonists psychotherapeutic, anti-malarial, L-dopa, diuretic, or antiulcer drugs.

41. The process according to claim 1, wherein the dispersed phase of Step (a) further comprises an agent, the agent comprising at least one member of lidocaine, xylocaine, dexadrine, phendimetrazine tartrate, methylprednisolone, ibuprofen, terbutaline sulfate, theophylline, ephedrine, sulfisoxazole, penicillin G, ampicillin, cephalosporin, amikacin, gentamicin, tetracycline, chloramphenicol, erythromycin, clindamycin, isoniazid, rifampin, amphotericin B, nystatin, ketoconazole, acyclovir, amantadine, cyclophosphamide, methotrexate, etretinate, heparin, warfarin, phenytoin sodium, diazepam, isocarboxazid, amoxapine, diphenhydramine HCl, chlorpheniramine maleate, insulin, progestin, estrogen, corticoid, glucocorticoid, androgen, steroids, corticosteroids, prostaglandins, thorazine, diazepam, chlorpromazine HCl, reserpine, chlordiazepoxide HCl, belladonna alkaloid, dicyclomine hydrochloride, essential amino acid, calcium, iron, potassium, zinc, vitamin $B_{12}$, prazosin HCl, nitroglycerin, propranolol HCl, hydralazine HCl, pancrelipase, succinic acid dehydrogenase, LHRH, somatostatin, calcitonin, growth hormone, glucagon-like peptides including glucagon, GLP-1, GLP-2, IP-1, IP-2; growth releasing factor, angiotensin, FSH, EGF, vasopressin, ACTH, human serum albumin, gamma globulin, toxins including botulinum toxin; morphine, codeine, furosemide, spironolactone, rantidine HCl, or cimetidine HCl.

42. The process according to claim 1, wherein the dispersed phase of Step (a) further comprises an agent, the agent comprising at least one member of an immunological agent, an allergen, or an antigen of a fungus, protozoa, or parasite.

43. The process according to claim 1, wherein the dispersed phase of Step (a) further comprises an agent, the agent comprising at least one member of cytokines, interleukins, interferon, colony stimulating factor, granulocyte-colony stimulating factors, granulocyte macrophage colony-stimulating factors, tumor necrosis factor, cat dander, birch pollen, house dust mite, or grass pollen.

44. The process according to claim 1, wherein the dispersed phase of Step (a) further comprises an agent, the agent comprising at least one member of antigens to cush bacterial organisms chosen from *Streptococcus pneumoniae, Haemophilus influenzae, Staphylococcus aureus, Streptococcus pyrogenes, Corynebacterium diphteriae, Listeria monocytogenes, Bacillus anthracis, Clostridium tetani, Clostridium botulinum, Clostridium perfringens, Neisseria meningitides, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptspirosis interrogans, Borrelia burgdorferi*, or *Campylobacter jejun*.

45. The process according to claim 1, wherein the dispersed phase of Step (a) further comprises an agent, wherein the agent is an antigen of a virus comprising at least one member of smallpox, influenza A, influenza B, respiratory synctial, parainfluenza, measles, HIV, SARS, varicella-zoster, herpes simplex 1 and 2, cytomeglavirus, Epstein-Barr, rotavirus, rhinovirus, adenovirus, papillomavirus, poliovirus, mumps, rabies, rubella, coxsackieviruses, equine encephalitis, Japanese encephalitis, yellow fever, Rift Valley fever, lymphocytic choriomeningitis, or hepatitis B.

46. The process according to claim 1, wherein the dispersed phase of Step (a) further comprises an agent, wherein the agent is an antigen of a fungus, protozoa, or parasite comprising at least one member of *Cryptococcuc neoformans, Histoplasma capsulatum, Candida albicans, Candida tropicalis, Nocardia asteroids, Rickettsia ricketsii, Rickettsia typhi, Mycoplasma pneumoniae, Chlamyda psittaci, Chlamydia trachomatis, Plasmodium falciparum, Trypanasoma brucei, Entamoeba histolytica, Toxoplasma gondii, Trichomonas Vaginalis*, or *Schistosoma manson*.

47. The process according to claim 1, wherein the microparticles further comprise an excipient comprising at least one member of an adhesive, a pesticide, a fragrance, an antifoulant, a dye, a salt, an oil, an ink, a cosmetic, a catalyst, a detergent, a curing agent, a flavor, a fuel, a herbicide, a metal, a paint, a photographic agent, a biocide, a pigment, a plasticizer, a propellant, a stabilizer, or a polymer additive.

48. The process according to claim 1, wherein the microparticles further comprise a pharmaceutically acceptable agent comprising at least one member of preservatives, lipids, fatty acids, waxes, surfactants, plasticizers, porosigens, antioxidants, bulking agents, buffering agents, chelating agents, cosolvents, water-soluble agents, insoluble agents, metal cations, anions, salts, osmotic agents, synthetic polymers, biological polymers, hydrophilic polymers, polysaccharides, sugars, hydrophobic polymers, hydrophilic block copolymers, hydrophobic block copolymers, block copolymers containing hydrophilic or hydrophobic blocks.

49. The process according to claim 1, wherein the composition of step (a) further comprises at least one member of a poly(vinyl pyrrolidone), a copolymer containing one or more blocks of poly(vinyl pyrrolidone) or one or more biocompatible polymers.

* * * * *